United States Patent
Musthakahmed et al.

(10) Patent No.: US 11,420,910 B2
(45) Date of Patent: Aug. 23, 2022

(54) METHODS FOR LOW TEMPERATURE FLUORINE-18 RADIOLABELING OF BIOMOLECULES

(71) Applicant: KATHOLIEKE UNIVERSITEIT LEUVEN, Leuven (BE)

(72) Inventors: Ahamed Muneer Syed Musthakahmed, Leuven (BE); Emilie Billaud, Leuven (BE); Guy Bormans, Rotselaar (BE); Frederik Cleeren, Oud-Heverlee (BE); Joan Lecina, Leuven (BE); Alfons Verbruggen, Wilsele (BE)

(73) Assignee: KATHOLIEKE UNIVERSITET LEUVEN, Leuven (BE)

( * ) Notice: Subject to any disclaimer, the term of this patent is extended or adjusted under 35 U.S.C. 154(b) by 170 days.

(21) Appl. No.: 15/522,859

(22) PCT Filed: Oct. 29, 2015

(86) PCT No.: PCT/BE2015/000063
§ 371 (c)(1),
(2) Date: Apr. 28, 2017

(87) PCT Pub. No.: WO2016/065435
PCT Pub. Date: May 6, 2016

(65) Prior Publication Data
US 2018/0273441 A1    Sep. 27, 2018

Related U.S. Application Data

(60) Provisional application No. 62/072,827, filed on Oct. 30, 2014.

(51) Int. Cl.
*A61K 51/00* (2006.01)
*A61M 36/14* (2006.01)
(Continued)

(52) U.S. Cl.
CPC ........ *C07B 59/008* (2013.01); *A61K 51/0482* (2013.01); *A61K 51/088* (2013.01);
(Continued)

(58) Field of Classification Search
CPC . C07B 59/008; C07B 2200/05; C07C 259/06; C07C 229/14; C07C 229/16; C07C 229/38; C07C 229/42; C07C 331/28; C07D 243/08; C07D 213/38; C07D 255/02; C07K 1/13; G01N 33/534; A61K 2123/00
USPC ..................................................... 424/1.89
See application file for complete search history.

(56) References Cited

U.S. PATENT DOCUMENTS 5,089,663 A    2/1992 Mease et al.
5,292,938 A    3/1994 Mease et al.
(Continued)

FOREIGN PATENT DOCUMENTS

| WO | 94/17029 A1 | 8/1994 | |
| WO | WO-0056743 A1 * | 9/2000 | ........... A61K 31/555 |
| WO | 2008088648 A2 | 7/2008 | |
| WO | 2010147666 A1 | 12/2010 | |
| WO | 2012082618 A2 | 6/2012 | |
| WO | WO-2013110615 A1 * | 8/2013 | |

OTHER PUBLICATIONS

PCT International Search Report and Written Opinion dated May 20, 2016 for PCT International Patent Application No. PCT/BE2015/000063, 18 pages.
(Continued)

*Primary Examiner* — Michael G. Hartley
*Assistant Examiner* — Sean R Donohue
(74) *Attorney, Agent, or Firm* — Amster, Rothstein & Ebenstein LLP

(57) ABSTRACT

New chelators such as $H_3L1$, $H_3L2$, $H_3L3$, $H_3L26$ and derivatives were synthesized for the complexation of $\{Al^{18}F\}^{2+}$. These new chelators are able to complex $\{Al^{18}F\}^{2+}$ with good radiochemical yields using a labeling temperature of 37° C. The stability of the new $Al^{18}F$-complexes was tested in phosphate buffered saline (PBS) at pH 7 and in rat serum. $Al^{18}F$-L3 and $Al^{18}F$-L26 showed a stability comparable to that of the previously reported $Al^{18}F$-NODA. Moreover, the biodistribution of $Al^{18}F$-L3 and $Al^{18}F$-L26 showed absence of in vivo demetallation since only very limited bone uptake was observed, whereas the major fraction of activity 60 min p.i. was observed in liver and intestine due to hepatobiliary clearance of the radiolabeled ligand. The chelators $H_3L3$ and $Al^{18}F$-L26 demonstrated to be a good lead candidates for the labeling of heat sensitive biomolecules with $^{18}F$-fluorine and derivatives have been synthesized. We have explored the complexation of $\{Al^{18}F\}^{2+}$ with new chelators and obtained very favourable radiochemical yields (>85%) using a labeling temperature of 37° C. The stability of the new $Al^{18}F$-complexes was tested in phosphate buffered saline (PBS) at pH 7 and in rat serum at 37° C., where $Al^{18}F$-L3 and $Al^{18}F$-L26 showed a stability comparable to that of the previously reported $Al^{18}F$-NODA. Moreover, the biodistribution of $Al^{18}F$-L3 and $Al^{18}F$-L26 showed high stability, since only very limited bone uptake—which would be an indication of release of fluorine-18 in the form of fluoride—was observed, whereas the major fraction of activity 60 min p.i. was observed in liver and intestines due to hepatobiliary clearance of the radiolabeled ligand. The chelators $H_3L3$ and $H_3L26$ demonstrated to be good lead candidates for the labeling of heat sensitive biomolecules with $^{18}F$-fluorine and several derivatives have been synthesized.

4 Claims, 43 Drawing Sheets

(51) Int. Cl.

| | | |
|---|---|---|
| *C07B 59/00* | (2006.01) | |
| *C07C 259/06* | (2006.01) | |
| *C07D 243/08* | (2006.01) | |
| *C07C 229/14* | (2006.01) | |
| *C07C 229/16* | (2006.01) | |
| *C07C 229/38* | (2006.01) | |
| *C07C 229/42* | (2006.01) | |
| *C07C 331/28* | (2006.01) | |
| *C07D 255/02* | (2006.01) | |
| *C07D 213/38* | (2006.01) | |
| *C07C 215/50* | (2006.01) | |
| *A61K 51/04* | (2006.01) | |
| *A61K 51/08* | (2006.01) | |
| *A61K 51/10* | (2006.01) | |
| *C07K 1/13* | (2006.01) | |
| *G01N 33/534* | (2006.01) | |

(52) U.S. Cl.
CPC ........ *A61K 51/1093* (2013.01); *C07C 215/50* (2013.01); *C07C 229/14* (2013.01); *C07C 229/16* (2013.01); *C07C 229/38* (2013.01); *C07C 229/42* (2013.01); *C07C 259/06* (2013.01); *C07C 331/28* (2013.01); *C07D 213/38* (2013.01); *C07D 243/08* (2013.01); *C07D 255/02* (2013.01); *C07K 1/13* (2013.01); *G01N 33/534* (2013.01); *A61K 2123/00* (2013.01); *C07B 2200/05* (2013.01); *C07B 2200/07* (2013.01); *C07C 2601/08* (2017.05); *C07C 2601/14* (2017.05)

(56) References Cited

U.S. PATENT DOCUMENTS

| | | |
|---|---|---|
| 5,635,157 A | 6/1997 | Mease et al. |
| 5,733,522 A | 3/1998 | Schmitt-Willich et al. |
| 5,840,859 A | 11/1998 | Lambert et al. |
| 2009/0155166 A1* | 6/2009 | McBride .............. A61K 51/109 424/1.49 |
| 2009/0299033 A1* | 12/2009 | McBride ............ A61K 51/0406 530/317 |

OTHER PUBLICATIONS

D'Souza C A et al: "High-Yielding Aqueous 18 F-Labeling of Peptides via Al 18 F Chelation", Bioconjugate Chemistry, vol. 22, No. 9, Sep. 21, 2011 (Sep. 21, 2011), 24 pages, pp. 1793-1803.

Shetty D et al: "Stable aluminium fluoride chelates with triazacyclononane derivatives proved by X-ray crystallography and 18F-labeling study", Chemical Communications, vol. 47, No. 34, Jan. 1, 2011 (Jan. 1, 2011), p. 9732-9734.

Mcbride W J et al: "Radiofluorination using aluminum-fluoride (Al18F)", Ejnmmi Research, vol. 3, No. 1, Jan. 1, 2013 (Jan. 1, 2013), 11 pages.

Witiak D T et al: "Study of trans-cyclopropylbis (diketopiperazine) and chelating agents related to ICRF 159. Cytotoxicity, mutagenicity, and effects on scheduled and unscheduled DNA synthesis", Journal of Medicinal Chemistry, vol. 20, No. 5, May 1, 1977 (May 1, 1977), pp. 630-635.

* cited by examiner

Scheme 3.
Scheme 4.

Scheme 5.

Scheme 8.
Scheme 9.

Scheme 10.
Scheme 11.
Scheme 12.

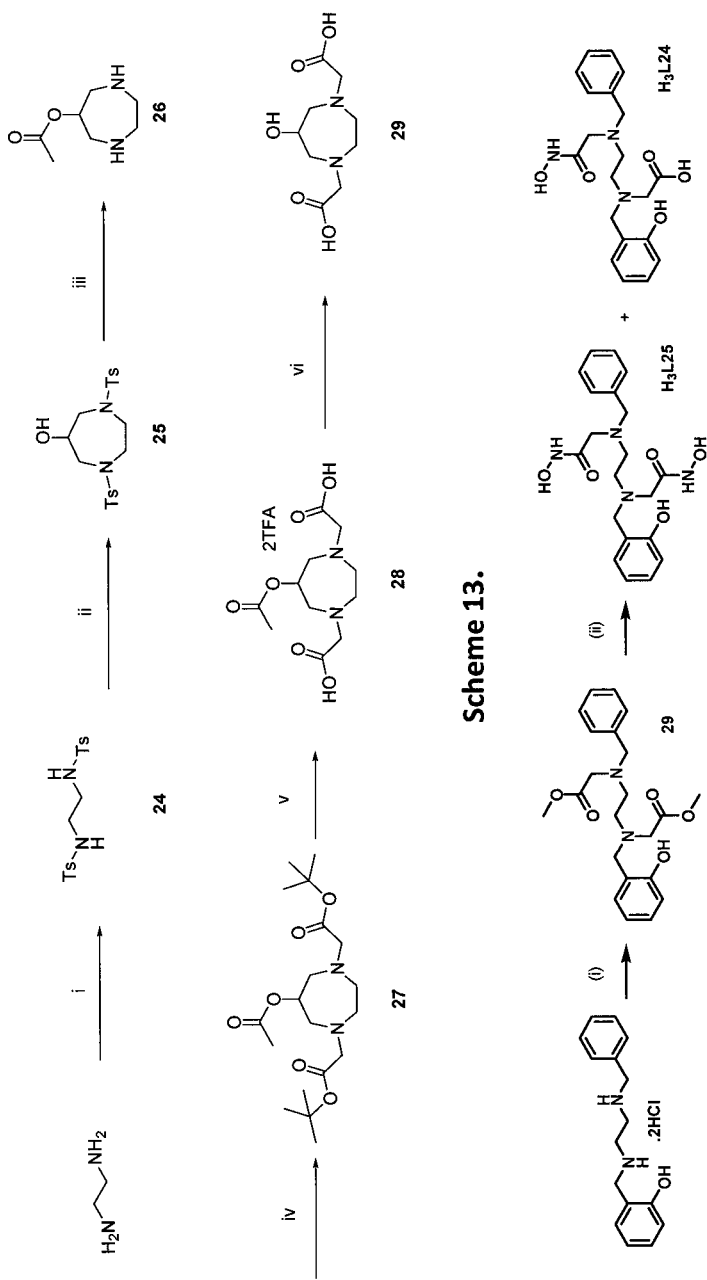

Scheme 15.

Scheme 19.

Scheme 22.

Scheme 23.

METHODS FOR LOW TEMPERATURE FLUORINE-18 RADIOLABELING OF BIOMOLECULES

CROSS-REFERENCE TO RELATED APPLICATIONS

This application is a U.S. national stage entry under 35 U.S.C. § 371 of PCT International Patent Application No. PCT/BE2015/000063, filed Oct. 29, 2015, which claims the benefit of U.S. Provisional Patent Application No. 62/072,827, filed Oct. 30, 2014, the contents of which are incorporated herein by reference in their entirety.

SUMMARY AND BACKGROUND

Summary of the Invention

Radiolabeling of biomolecules such as peptides or proteins with fluorine-18 using the aluminum fluoride ($\{Al^{18}F\}^{2+}$) approach and the chelators 1,4,7-triazacyclononane-1,4,7-triacetic acid (NOTA) and 1,4,7-triazacyclononane-1,4-diacetic acid (NODA) was the first example of radiofluorination in aqueous media.

However, the high temperature required for radiolabeling (>100° C.) is still the main shortcoming that limits widespread application for radiolabeling of biomolecules for PET. Thus, there is a need in the art for such radiolabeling at low temperatures, which is particularly useful for temperature sensitive compounds such as biomolecules. Present invention provides such solution.

We have explored the complexation of $\{Al^{18}F\}^{2+}$ with new chelators and obtained very favourable radiochemical yields (>85%) using a labeling temperature of 37° C. The stability of the new $Al^{18}F$-complexes was tested in phosphate buffered saline (PBS) at pH 7 and in rat serum at 37° C., where $Al^{18}F$-L3 and $Al^{18}F$-L26 showed a stability comparable to that of the previously reported $Al^{18}F$-NODA. Moreover, the biodistribution of $Al^{18}F$-L3 and $Al^{18}F$-L26 showed high stability, since only very limited bone uptake-which would be an indication of release of fluorine-18 in the form of fluoride—was observed, whereas the major fraction of activity 60 min p.i. was observed in liver and intestines due to hepatobiliary clearance of the radiolabeled ligand. The chelators $H_3L3$ and $H_3L26$ demonstrated to be good lead candidates for the labeling of heat sensitive biomolecules with $^{18}F$-fluorine and several derivatives have been synthesized.

FIELD OF THE INVENTION

The present invention relates generally to a process for radiolabeling of temperature-sensitive biomolecules (such as peptides or proteins) at a temperature not exceeding 40° C. using chelation of aluminum fluoride ($\{Al^{18}F\}^{2+}$) with new chelators and, more particularly to a system and method with a chelator represented by the following formulae:

formula (I):

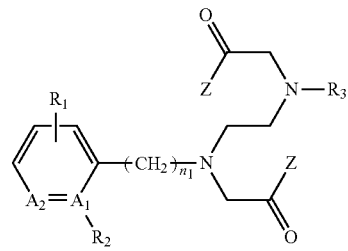

in which
$R_1$ represents an hydrogen atom, a halogen, $NO_2$, OMe, OH, or an amide group,
$A_1$ represents a carbon atom or a nitrogen atom,
$A_2$ represents a carbon atom or a nitrogen atom,
$R_2$ is defined only when $A_1$ is a carbon atom, and then $R_2$ represents a hydrogen atom, OH, SH, a phosphonate group or a phosphinate group,
$n_1$ is an integer varying from 0 to 3,
Z represents OH, NH—OH, or NMe-OH,
$R_3$ represents an aromatic, aliphatic, cyclic or non-cyclic group,
and their pharmaceutically acceptable salts.
or formula (II):

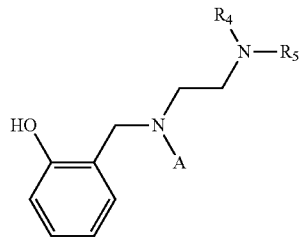

in which
A represents a hydrogen atom, a ($C_1$-$C_6$)alkyl group or a —$CH_2$—Ar group
with Ar being an aromatic ring
$R_4$ represents a —$CH_2$—COOH or a —$CH_2$-Ph-R' group
with R' in ortho, meta or para position, being a hydrogen atom, OH, —COOH, —$NH_2$, —N=C=S, —SH, an activated ester or a group bearing a maleimide,
$R_5$ represents —$CH_2$—COOH, —$(CH_2)_2NH_2$ or —$(CH_2)_2$—NH—$CH_2$-Ph-R"
with R" in ortho, meta or para position, being a hydrogen atom, a halogen, $NO_2$, OMe, OH, or an amide group,
and their pharmaceutically acceptable salts.
or formula (III):

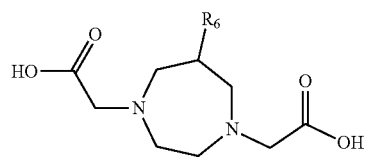

in which
R$_6$ represents OH, or a nitrogen atom substituted by (C$_1$-C$_6$)alkyl group(s) and/or —CH$_2$—Ar group(s) with Ar being an aromatic ring
and their pharmaceutically acceptable salts.

According to a fourth aspect a subject-matter of the present invention relates to a compound of formula (IV):

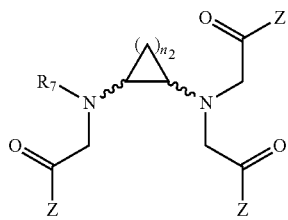

in which n$_2$ is an integer varying from 1 to 7, in the case of n$_2$=4, the 6-membered ring is cyclic without substituents, or is di-substituted by hydroxyl groups, or includes a double bond, or is an heterocycle with an oxygen as heteroatom, or is aromatic with or without heteroatom.

Z represents SH, OH, NH—OH, or NMe-OH

R$_7$ represents an aromatic, aliphatic, cyclic or non-cyclic group, the asymmetric carbon atoms are in (R) or (S) configuration, and their pharmaceutically acceptable salts.

According to a particular embodiment, the present invention is directed to a compound of formula (IV) as defined above, wherein n$_2$ is an integer varying from 1 to 4.

According to said particular embodiment, when n$_2$=4, the 6-membered ring is cyclic without substituents, or includes a double bond.

According to another particular embodiment, the present invention is directed to a compound of formula (IV) as defined above, wherein R$_7$ represents a (C$_1$-C$_6$)alkyl group or a —CH$_2$-Ph-R' group
with R' in ortho, meta or para position, being an hydrogen atom, —COOH, —NH$_2$, —N=C=S, —SH, or any functional group suitable for conjugation such as an activated ester or a group bearing a maleimide.

The following R' group: —COOH, —NH$_2$, —N=C=S, —SH, an activated ester or a group bearing a maleimide are used for coupling with compounds bearing a suitable chemical function.

According to said particular embodiment, the present invention is more particularly directed to the compounds of formula (IV), wherein R$_7$ is a methyl group or a —CH$_2$-Ph-R' group
with R' in para position, being an hydrogen atom, —COOH, —NH$_2$, —N=C=S, —SH, an activated ester or a group bearing a maleimide.

The following R' group: —COOH, —NH$_2$, —N=C=S, —SH, an activated ester or a group bearing a maleimide are used for coupling with compounds bearing a suitable chemical function. Several documents are cited throughout the text of this specification. Each of the documents herein (including any manufacturer's specifications, instructions etc.) are hereby incorporated by reference; however, there is no admission that any document cited is indeed prior art of the present invention.

DESCRIPTION OF THE RELATED ART

Radiolabeling of biomolecules such as peptides or proteins using the aluminum fluoride ($\{Al^{18}F\}^{2+}$) approach and the chelators 1,4,7-triazacyclononane-1,4,7-triacetic acid (NOTA) and 1,4,7-triazacyclononane-1,4-diacetic acid (NODA) were the first examples of radiofluorination in aqueous media.

However, the high temperatures required for radiolabeling (>100° C.) are still the main shortcoming that limits widespread application for radiolabeling of biomolecules with fluorine-18 for PET.

Thus, there is a need in the art for radiolabeling biomolecules at temperatures not exceeding 40° C. This is particularly useful for temperature sensitive compounds such as biomolecules. Present invention provides such solution.

BACKGROUND OF THE INVENTION

Positron Emission Tomography (PET) is a non-invasive technology of nuclear medicine that provides useful information related with functional processes in the body.[1,2,3] PET requires specific probes radiolabeled with a usually short-lived positron emitting radionuclide, which can be quantified in vivo by detection of the gamma rays formed as a result of annihilation of the positrons.[4,5] PET offers picomolar sensitivity, good spatial resolution and is a fully translational technique.[6,7] Among the positron-emitting radioisotopes (e.g. $^{11}$C, $^{64}$Cu, $^{18}$F, $^{13}$N, $^{15}$O, $^{68}$Ga, $^{89}$Zr, $^{124}$I), fluorine-18 has several advantages such as suitable decay properties ($t_{1/2}$=109.8 min, ~97% $\beta^+$-emission, Emax 635 keV), short $\beta^+$-trajectory in water (<2 mm), and moreover, it is readily produced in large quantities (>400 GBq/batch) with a cyclotron. For radiolabeling of peptides and proteins generator-produced metallic PET radioisotopes, such as $^{64}$Cu and $^{68}$Ga, have been proven to be quite suitable.[8] Nevertheless, the growing availability of fluorine-18, and its almost ideal properties make its use in labeling biomolecules attractive.

However, the incorporation of fluorine-18 into heat sensitive and complex biomolecules creates substantial challenges for radiochemists. The main problem to overcome in radiolabeling by carbon-fluorine bond formation is the low nucleophilicity of fluoride ions in the presence of water. Therefore several time-consuming drying steps, (multi-step) reactions in organic solvents and high temperatures need to be applied, conditions that are not compatible with sensitive biomolecules.[9]

During the last years several groups explored a new straightforward approach for radiolabeling peptides with fluorine-18[10-14] exploiting the strong bond between fluorine and Al$^3$. The aluminum-fluoride bond is stronger than other metal-fluoride bonds, with a bond-energy of 670 kJ/mol. At low fluoride concentration, Al$^{3+}$ forms an AlF$^{2+}$ monofluoride moiety which can be chelated by a suitable chelator. The preferred coordination number of aluminum is 6, producing octahedral complexes. However, to form chelates with AlF$^{2+}$ one of the coordination sites must remain available to be occupied by the fluorine atom, so ideally a pentadentate ligand is used.[10]

Metal ions are Lewis acids (electron pair acceptors; electrophiles) that have incomplete valence electron shells. Moreover, aluminum is the hardest trivalent metal ion (hard Lewis acid) with an effective ionic radius around 50 pm. As a consequence, $Al^{3+}$ prefers to coordinate with hard Lewis bases such as $OH^-$, $F^-$, $PO_4^{3-}$; $SO_4^{2-}$; $RCOO^-$, ROH, $RO^-$ and $RNH_2$, which donate electrons to its vacant electron orbitals. It is demonstrated that the most stable aluminum complexes are multidentate ligands with negative oxygen donors.[15] The challenge with the $Al^{18}F$-chelation method is to find a suitable ligand that quickly and efficiently chelates $\{Al^{18}F\}^{2+}$ providing a complex that is stable for several hours in vitro and in vivo.

McBride and colleagues published the first study using a chelator for $\{Al^{18}F\}^{2+}$ labeling in 2009. The most promising chelators tested until now are 1,4,7-triazacyclononane-1,4,7-triacetic acid (NOTA)[10,11] and 1,4,7-triazacyclononane-1,4-diacetic acid (NODA)[10,11,16] (FIG. 1). Although these macrocyclic chelators showed a lot of promise for radiolabeling peptides, there are still some shortcomings that prevent their widespread use. In the chelation process of the $\{Al^{18}F\}^{2+}$ species with NOTA or NODA, the reaction requires heating to 100-120° C. This is problematic when the chelator-$[Al^{18}F]^{2+}$-complex is coupled to heat sensitive biomolecules.[17] Therefore it would be desirable to have an alternative chelator, with lower activation energy for chelation of the aluminum-fluoride complex and consequently allowing to avoid the heating step. This could result in a kit-based, room-temperature radiolabeling condition in aqueous media.

Kit preparation of fluorine-18 labeled PET tracers has the generic potential to substitute current technetium-99m labeled tracers in view of the better performance of PET vs. SPECT as an imaging technology and recent problems with availability of technetium-99m generators.

Present invention provides a solution of carrying out the chelation of the $\{AlF\}^{2+}$ moiety at moderate temperatures (<40° C.) by using polydentate ligands (FIG. 2). It was found that open variants are likely to chelate $\{Al^{18}F\}^{2+}$ faster and at lower temperatures than macrocyclic chelators. These novel derivatives have been evaluated as such (i.e. without being conjugated to biomolecules) to fully assess the $\{Al^{18}F\}^{2+}$-fragment chelation efficiency and the in vivo and in vitro stability of the corresponding chelates.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description. It is to be understood that both the foregoing general description and the following detailed description are exemplary and explanatory only and are not restrictive of the invention, as claimed.

DETAILED DESCRIPTION

Detailed Description of Embodiments of the Invention

The following detailed description of the invention refers to the accompanying figures. The same reference numbers in different drawings identify the same or similar elements. Also, the following detailed description does not limit the invention. Instead, the scope of the invention is defined by the appended claims and equivalents thereof.

Several documents are cited throughout the text of this specification. Each of the documents herein (including any manufacturer's specifications, instructions etc.) are hereby incorporated by reference; however, there is no admission that any document cited is indeed prior art of the present invention.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn to scale for illustrative purposes. The dimensions and the relative dimensions do not correspond to actual reductions to practice of the invention.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to the devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may be. Furthermore, the particular features, structures or characteristics may be combined in any suitable manner, as would be apparent to someone of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Other embodiments of the invention will be apparent to those skilled in the art from consideration of the specification and practice of the invention disclosed herein.

It is intended that the specification and examples be considered as exemplary only.

Each and every claim is incorporated into the specification as an embodiment of the present invention. Thus, the claims are part of the description and are a further description and are in addition to the preferred embodiments of the present invention.

Each of the claims set out a particular embodiment of the invention.

An example of a phosphonate group is a C—PO(OR)2 group, wherein R=alkyl or R=aryl. The following terms are provided solely to aid in the understanding of the invention. Phosphonites are organophosphorus compounds with the formula P(OR)2R. An example of a phosphonate group is a C—P(OR)2R group, wherein R=alkyl or R=aryl.

According to a first aspect, a subject-matter of the present invention relates to a compound of formula (I):

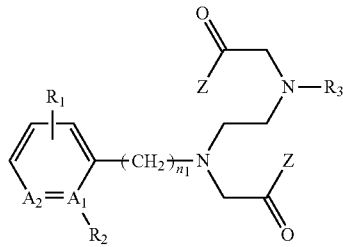

in which
$R_1$ represents a hydrogen atom, a halogen, $NO_2$, OMe, OH, or an amide group,
$A_1$ represents a carbon atom or a nitrogen atom,
$A_2$ represents a carbon atom or a nitrogen atom,
$R_2$ is defined only when $A_1$ is a carbon atom, and $R_2$ then represents a hydrogen atom, OH, SH, a phosphonate group or a phosphinate group,
$n_1$ is an integer varying from 0 to 3,
Z represents OH, NH—OH, or NMe-OH,
$R_3$ represents an aromatic, aliphatic, cyclic or non-cyclic group,
and their pharmaceutically acceptable salts.

According to a particular embodiment, the present invention is directed to a compound of formula (I) as defined above, wherein $n_1$ is an integer varying from 0 to 1.

According to another particular embodiment, the present invention is directed to a compound of formula (I) as defined above, wherein $R_3$ represents a —$CH_2$—COOH group or a —$CH_2$-Ph-R' group
with R' in ortho, meta or para position, being a hydrogen atom, —OH, —COOH, —$NH_2$, —N=C=S, —SH, any group that can be used for conjugation such as activated ester or a group bearing a maleimide.

The following R' groups: —COOH, —$NH_2$, —N=C=S, —SH, an activated ester or a group bearing a maleimide are used for coupling with compounds bearing a suitable chemical function.

According to another particular embodiment, the present invention is directed to a compound of formula (Ia)

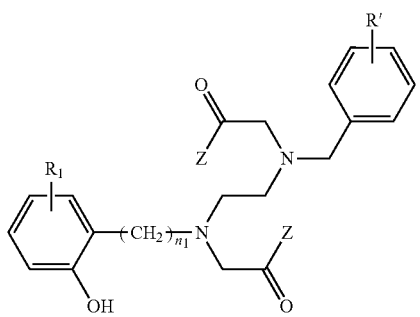

in which
$R_1$ represents a hydrogen atom, a halogen, $NO_2$, OMe, OH, or an amide group,
$n_1$ is an integer varying from 0 to 1,
Z represents OH, NH—OH, or NMe-OH,
R' represents a hydrogen atom, —OH, —COOH, —$NH_2$, —N=C=S, —SH, an activated ester or a group bearing a maleimide.

The following R' groups: —COOH, —$NH_2$, —N=C=S, —SH, an activated ester or a group bearing a maleimide are used for coupling with compounds bearing a suitable chemical function,
and their pharmaceutically acceptable salts.

According to said particular embodiment, the present invention is more particularly directed to the compounds of formula (Ia), wherein $R_1$ represents a hydrogen atom, a fluorine atom, $NO_2$, OMe or OH.

According to said same particular embodiment, the present invention is more particularly directed to the compounds of formula (Ia), wherein R' is in ortho or para position and represents a hydrogen atom, —OH, —COOH, —$NH_2$, —N=C=S or an activated ester, and more particularly R' is in para position and represents a hydrogen atom, —COOH, —$NH_2$, —N=C=S or an activated ester.

According to another particular embodiment, the present invention is directed to a compound of formula (Ib)

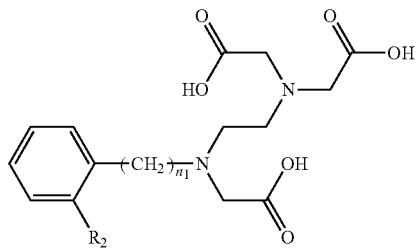

in which
R$_2$ represents a hydrogen atom or OH,
n$_1$ is an integer varying from 0 to 1,
and their pharmaceutically acceptable salts.

According to said particular embodiment, the present invention is more particularly directed to the compounds of formula (Ib), wherein R$_2$ is an hydrogen atom.

According to said same particular embodiment, the present invention is more particularly directed to the compounds of formula (Ib), wherein n$_1$ is 1.

According to another particular embodiment, the present invention is directed to a compound of formula (Ic)

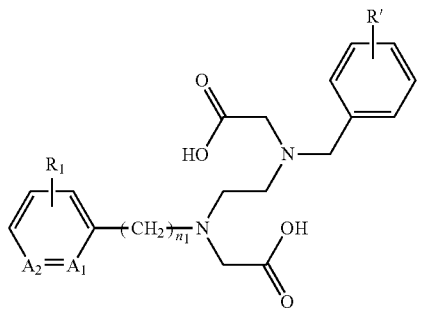

in which
R$_1$ represents a hydrogen atom, a halogen, NO$_2$, OMe, OH, or an amide group,
A$_1$ represents a carbon atom or a nitrogen atom,
A$_2$ represents a carbon atom or a nitrogen atom,
n$_1$ is an integer varying from 0 to 1,
R' represents a hydrogen atom, —OH, —COOH, —NH$_2$, —N=C=S, —SH, an activated ester or a group bearing a maleimide,
and their pharmaceutically acceptable salts.

According to said particular embodiment, the present invention is more particularly directed to the compounds of formula (Ic), wherein R$_1$ is a hydrogen atom or OH.

According to said same particular embodiment, the present invention is more particularly directed to the compounds of formula (Ic), wherein n$_1$ is 1.

According to a second aspect a subject-matter of the present invention relates to a compound of formula (II):

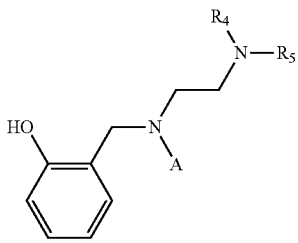

in which
A represents a hydrogen atom, a (C$_1$-C$_6$)alkyl group or a —CH$_2$—Ar group
with Ar being an aromatic ring
R$_4$ represents a —CH$_2$—COOH or a —CH$_2$-Ph-R' group
with R' in ortho, meta or para position, being a hydrogen atom, OH, —COOH, —NH$_2$, —N=C=S, —SH, an activated ester or a group bearing a maleimide,
R$_5$ represents —CH$_2$—COOH, a —(CH$_2$)$_2$NH$_2$ or —(CH$_2$)$_2$—NH—CH$_2$-Ph-R"

with R" in ortho, meta or para position, being a hydrogen atom, an halogen, NO$_2$, OMe, OH, or an amide group,
and their pharmaceutically acceptable salts.

According to a particular embodiment, the present invention is directed to a compound of formula (II) as defined above, wherein A is a hydrogen atom, a methyl group or a —CH$_2$-Ph group.

According to another particular embodiment, the present invention is directed to a compound of formula (II) as defined above, wherein R' is in ortho position and is a hydrogen atom or OH.

According to another particular embodiment, the present invention is directed to a compound of formula (II) as defined above, wherein R" is in ortho position and is OH.

According to a third aspect a subject-matter of the present invention relates to a compound of formula (III):

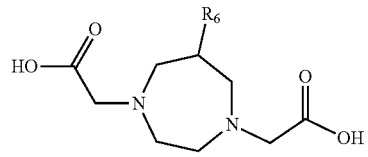

in which
R$_6$ represents OH, or a nitrogen atom substituted by (C$_1$-C$_6$)alkyl group(s) and/or —CH$_2$—Ar group(s)
with Ar being an aromatic ring
and their pharmaceutically acceptable salts.

According to a particular embodiment, the present invention is directed to a compound of formula (III) as defined above, wherein R$_6$ represents OH, or a nitrogen atom di-substituted by two ethyl groups.

According to a fourth aspect a subject-matter of the present invention relates to a compound of formula (IV):

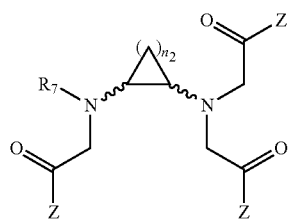

in which
n$_2$ is an integer varying from 1 to 7,
in the case of n$_2$=4, the 6-membered ring is cyclic without substituents, or is di-substituted by hydroxyl groups, or includes a double bond, or is an heterocycle with an oxygen as heteroatom, or is aromatic with or without a heteroatom.
Z represents SH, OH, NH—OH, or NMe-OH
R$_7$ represents an aromatic, aliphatic, cyclic or non-cyclic group,
the asymmetric carbon atoms are in (R) or (S) configuration,
and their pharmaceutically acceptable salts.

According to a particular embodiment, the present invention is directed to a compound of formula (IV) as defined above, wherein n$_2$ is an integer varying from 1 to 4.

According to said particular embodiment, when n$_2$=4, the 6-membered ring is cyclic without substituents, or includes a double bond.

According to another particular embodiment, the present invention is directed to a compound of formula (IV) as defined above, wherein $R_7$ represents a $(C_1-C_6)$alkyl group or a —$CH_2$-Ph-R' group
with R' in ortho, meta or para position, being an hydrogen atom, —COOH, —$NH_2$, —N=C=S, —SH, an activated ester or a group bearing a maleimide.

The following R' group: —COOH, —$NH_2$, —N=C=S, —SH, an activated ester or a group bearing a maleimide are used for coupling with compounds bearing a suitable chemical function.

According to said particular embodiment, the present invention is more particularly directed to the compounds of formula (IV), wherein $R_7$ is a methyl group or a —$CH_2$-Ph-R' group
with R' in para position, being an hydrogen atom, —COOH, —$NH_2$, —N=C=S, —SH, an activated ester or a group bearing a maleimide.

The following R' group: —COOH, —$NH_2$, —N=C=S, —SH, an activated ester or a group bearing a maleimide are used for coupling with compounds bearing a suitable chemical function.

According to said particular embodiment, the present invention is more particularly directed to the compounds of formula (IV), wherein $R_7$ is a methyl group or a —$CH_2$-Ph-R' group
with R' in para position, being an hydrogen atom, —COOH, —$NH_2$, —N=C=S, —SH, an activated ester or a group bearing a maleimide.

The following R' group: —COOH, —$NH_2$, —N=C=S, —SH, an activated ester or a group bearing a maleimide are used for coupling with compounds bearing a suitable chemical function.

According to another aspect, the invention is directed to radiolabeled compounds containing ligands of formula (I), (Ia), (Ib), (Ic), (II), (III) or (IV) wherein said radiolabeling occurs by means of chelation. This chelation can be the one of a metal fluoride ($\{M^{18}F\}^{2+}$), with a metal from group 13 of the periodic table, among aluminum, gallium, indium, lutetium and thallium.

In the context of the present invention, the term:
"Ph" means a phenyl group,
"Me" means a methyl group,
"$(C_1-C_6)$alkyl" as used herein refers to $C_1-C_6$ normal, secondary, or tertiary saturated hydrocarbon. Examples are, but are not limited to, methyl, ethyl, 1-propyl, 2-propyl, 1-butyl, 2-methyl-1-propyl (i-Bu), 2-butyl (s-Bu), 2-methyl-2-propyl (t-Bu).

Within the meaning of the present invention, the term "radionuclide" is understood to mean a radioisotope of natural or artificial origin which demonstrates radioactive properties. The radionuclide can be fluorine-18.

Moreover, the term "labeled" as used herein means "radiolabeled" and is more precisely directed to a compound comprising at least one radionuclide, i.e. a radioactive nuclide.

According to a preferred embodiment of the present invention, the compound is chosen from:
2,2'-((2-(benzyl(carboxymethyl)amino)ethyl)azanediyl)diacetic acid ($H_3L1$)
2,2'-(ethane-1,2-diylbis((2-hydroxybenzyl)azanediyl))diacetic acid ($H_3L2$),
2-(benzyl(2-((carboxymethyl)(2-hydroxybenzyl)amino)ethyl)amino)acetic acid ($H_3L3$),
2-(benzyl(2-((carboxymethyl)(5-fluoro-2-hydroxybenzyl)amino)ethyl)amino)acetic acid ($H_3L4$),
2-(benzyl(2-((carboxymethyl)(2-hydroxy-5-nitrobenzyl)amino)ethyl)amino)acetic acid ($H_3L5$),
4-(((carboxymethyl)(2-((carboxymethyl)(2-hydroxybenzyl)amino)ethyl)amino)methyl)benzoic acid ($H_3L6$),
2-(benzyl(2-((carboxymethyl)(pyridin-2-ylmethyl)amino)ethyl)amino)acetic acid ($H_2L7$),
2-((2-(benzyl(2-hydroxybenzyl)amino)ethyl)(2-hydroxybenzyl)amino)acetic acid ($H_3L8$)
2,2'-((2-(benzyl(2-hydroxybenzyl)amino)ethyl)azanediyl)diacetic acid ($H_3L9$)
2-(((2-aminoethyl)(2-(benzyl(2-hydroxybenzyl)amino)ethyl)amino)methyl)phenol ($H_2L10$)
2-(benzyl(2-((carboxymethyl)(pyridin-3-ylmethyl)amino)ethyl)amino)acetic acid ($H_2L11$),
2,2'-(((((benzylazanediyl)bis(ethane-2,1-diyl))bis(azanediyl))bis(methylene))diphenol ($H_2L12$),
2,2'-(6-hydroxy-1,4-diazepane-1,4-diyl)diacetic acid ($H_3L13$),
2-((4-aminobenzyl)(2-((carboxymethyl)(2-hydroxybenzyl)amino)ethyl)amino)acetic acid ($H_3L14$),
2-((2-((carboxymethyl)(2-hydroxybenzyl)amino)ethyl)(4-isothiocyanatobenzyl)amino)acetic acid ($H_3L15$),
2-(benzyl(2-((carboxymethyl)(2-hydroxy-4-nitrobenzyl)amino)ethyl)amino)acetic acid ($H_3L16$),
2-(benzyl(2-((carboxymethyl)(2-hydroxy-5-methoxybenzyl)amino)ethyl)amino)acetic acid ($H_3L17$),
2-(benzyl(2-((carboxymethyl)(3-hydroxybenzyl)amino)ethyl)amino)acetic acid ($H_3L18$),
2-((2-hydroxybenzyl)(2-((2-hydroxybenzyl)(methyl)amino)ethyl)amino)acetic acid ($H_3L19$),
2-(benzyl(2-((carboxymethyl)(2-hydroxyphenyl)amino)ethyl)amino)acetic acid ($H_3L20$),
2,2'-(6-(benzyl(methyl)amino)-1,4-diazepane-1,4-diyl)diacetic acid ($H_2L21$),
2-(benzyl(2-((carboxymethyl)(2,6-dihydroxybenzyl)amino)ethyl)amino)acetic acid ($H_3L22$),
2-(benzyl(2-((2-(hydroxy(methyl)amino)-2-oxoethyl)(2-hydroxybenzyl)amino)ethyl)amino)-N-hydroxy-N-methylacetamide ($H_3L23$)
2-((2-(benzyl(2-(hydroxyamino)-2-oxoethyl)amino)ethyl)(2-hydroxybenzyl)amino)acetic acid ($H_3L24$),
2-(benzyl(2-((2-(hydroxyamino)-2-oxoethyl)(2-hydroxybenzyl)amino)ethyl)amino)-N-hydroxyacetamide ($H_3L25$),
2-[4-({[(±)-trans-2-{bis[2-(tert-butoxy)-2-oxoethyl]amino}cyclohexyl][2-(tert-butoxy)-2-oxoethyl]amino}methyl)phenyl]acetic acid ($H_3L26$),
2-{[(±)-trans-2-[benzyl(carboxymethyl)amino]cyclohexyl](carboxymethyl)amino}acetic acid ($H_3L27$),
2,2'-(((1R,2R)-2-((carboxymethyl)(4-(2-oxo-2-(2,3,5,6-tetrafluorophenoxy)ethyl)benzyl)amino)cyclohexyl)azanediyl)diacetic acid ($H_3L28$),
2-{[cis-2-[benzyl(carboxymethyl)amino]cyclohexyl](carboxymethyl)amino}acetic acid $H_3L29$),
(2,2'-(((1R,6R)-6-(benzyl(carboxymethyl)amino)cyclohex-3-en-1-yl)azanediyl)diacetic acid $H_3L30$),
2,2'-(((1R,2R)-2-(benzyl(carboxymethyl)amino)cyclopentyl)azanediyl)diacetic acid ($H_3L31$),
and their pharmaceutically acceptable salts.
2,2'-((2-(benzyl(carboxymethyl)amino)phenyl)azanediyl) diacetic acid ($H_3L32$)

The compounds of formulae (I), (Ia), (Ib), (Ic), (II) and (III) can comprise one or more asymmetric carbon atoms. They can thus exist in the form of enantiomers or of diastereoisomers. These enantiomers, diastereoisomers and their mixtures, including the racemic mixtures, form part of the invention.

The pharmaceutically acceptable salts of the compounds of formulae (I), (Ia), (Ib), (Ic), (II) and (III) include the addition salts with pharmaceutically acceptable acids, such as inorganic acids, for example hydrochloric, hydrobromic, phosphoric or sulphuric acid and organic acids, such as acetic, trifluoroacetic, propionic, oxalic, succinic, fumaric, malic, tartaric, citric, ascorbic, maleic, glutamic, benzoic, toluenesulphonic, methanesulphonic, stearic and lactic acid.

The compounds of formulae (I), (Ia), (Ib), (Ic), (II) and (III) or their salts can form solvates (namely hydrates); the invention includes such solvates.

A further aspect of the invention pertains to a radiolabeled compound comprising a ligand of formula (I), (Ia), (Ib), (Ic), (II) and (Ill) as described above, wherein said radiolabeling occurs by means of chelation. This chelation can be the one of a metal fluoride ($\{M^{18}F\}^{2+}$) with a metal chosen such as aluminum, gallium, indium, lutetium, and thallium, and more particularly aluminum.

The following examples illustrate the invention.

The reagents and solvents used were all purchased at Sigma-Aldrich (Bornem, Belgium), Fluka (Bornem, Belgium), Fisher (Doornik, Belgium) and Acros Organics (Geel, Belgium). Fluorine-18 was delivered on site from a cyclotron by irradiation of $H_2^{18}O$ by protons, accelerated to 18 MeV in a cyclotron (IBA Cyclone 18/9). Radioactivity was measured using an ionization chamber based activity meter (Capintec Radioisotope Calibrator® CRC-721, Ramsey, N.J., USA).

Identification of the mass of various compounds was achieved by a Dionex Ultimate 3000 LC System coupled in series to an ultra-high resolution time-of-flight mass spectrometry (TOF-HRMS) (maXis impact, Bruker, Bremen, Germany), equipped with orthogonal electrospray ionization (ESI) interface. Acquisition and processing of data were conducted using HyStar and Compass DataAnalysis (version 3.2, Bruker), respectively. Calculated monoisotopic mass values were obtained using MarvinSketch (version 6.1.0, ChemAxon).

Thin layer chromatography (TLC) was often used for rapid identification and developing separation systems. The TLC plates were silica-based (Silica gel 60 plates, Merck, Darmstadt, Germany).

Preparative High Pressure Liquid Chromatography (prep-HPLC) was carried out with a Merck-Hitachi L-6200 pump (Merck, Darmstadt, Germany) on a Waters XTerra preparative C18 10 µm 10 mm×250 mm column. The mobile phase, which consisted of gradient mixtures of water and acetonitrile, eluted the different compounds at a flow rate of 5 mL/min. The eluate was analyzed for its UV absorbance (Merck Hitachi L-4200 UV-VIS detector) at 254 nm.

Chemical structure elucidation was performed using proton-nuclear magnetic resonance ($^1$H-NMR) spectrometry at 400 MHz, carbon-nuclear magnetic resonance ($^{13}$C-NMR)[19] spectrometry at 101 MHz and fluorine-nuclear magnetic resonance ($^{19}$F{$^1$H}-NMR) spectrometry at 376 MHz on a Bruker AVANCE 400 MHz spectrometer (5 mm probe, Bruker AG, Fällanden, Switzerland).

ITLC-SG papers (Varian, Diegem, Belgium) were developed in an elution chamber using a mixture of 75% acetonitrile and 25% water. Autoradiography was performed using phosphor storage screens (super-resolution screen, Perkin Elmer). Screens were read in a Cyclone Plus system (Perkin Elmer) and analysed using Optiquant software.

Example 1: Synthesis of Ligand $H_3L1$ (FIG. 2 and Scheme 1)

Step 1: Synthesis of Compound 1 (diethyl 2,2'-((2-(benzyl(2-ethoxy-2-oxoethyl)amino)ethyl)azanediyl) diacetate)

To a solution of N-benzylethylenediamine (0.7 g, 4.66 mmol) in tetrahydrofuran (4 mL), potassium carbonate (1.9 g, 13.7 mmol) and ethyl bromoacetate (3.0 mL, 27.1 mmol) were successively added. The mixture was stirred for 6 h at room temperature (RT). The solvent was evaporated and ethyl acetate (20 mL) was added. The organic phase was washed with water (3×10 mL), dried over magnesium sulfate and the solvent was evaporated under reduced pressure. Flash column chromatography on silica gel (ethyl acetate/heptane, 1:5) afforded pure product, 1 (3.1 g, 80) %. HRMS (ESI): Calcd. for $C_{21}H_{32}N_2O_6$ [M+H$^+$] 408.2261; found 408.2286. $^1$H NMR (400 MHz, CDCl$_3$) δ 7.39-7.19 (m, 5H), 4.14 (q, J=7.1 Hz, 6H), 3.80 (s, 2H), 3.57 (s, 4H), 3.37 (s, 2H), 2.86 (tt, J=7.3, 3.7 Hz, 4H), 1.27 (s, 9H). $^{13}$C NMR (101 MHz, CDCl$_3$) δ 171.5, 171.3 (2C), 138.8, 129.0 (2C), 128.3 (2C), 127.1, 60.4 (2C), 60.2, 58.5, 55.3 (2C), 54.2, 52.1, 52.0, 14.3, 14.2 (2C).

Step 2: Synthesis of Compound Na$_3$L1 (sodium 2,2'-((2-(benzyl(carboxylatomethyl)amino)ethyl) azanediyl)diacetate)

Compound 1 (0.10 g, 0.25 mmol) was stirred in a mixture comprising an aqueous solution of sodium hydroxide (1 M) and methanol (1:3, 3 mL) for 12 h at RT. Then, the solvent was removed by evaporation. The residue was washed with absolute ethanol and dry diethyl ether, affording Na$_3$L1 as a yellow pale solid (61 mg, 63%). HRMS (ESI): Calcd. For $C_{15}H_{20}N_2O_6$ [M+H$^+$], Exact Mass: 325.1321, Mol. Wt.: 325.1391. $^1$H NMR (400 MHz, D$_2$O) δ 7.46-7.29 (m, 5H), 3.67 (s, 2H), 3.05 (s, 2H), 3.02 (s, 4H), 2.62 (s, 4H). $^{13}$C NMR (101 MHz, D$_2$O) δ 180.2 (2C), 179.9, 138.0, 130.8 (2C), 129.1 (2C), 128.2, 59.2 (2C), 58.5, 58.1, 51.9, 51.2.

Example 2: Synthesis of Ligand $H_3L2$ (FIG. 2 and Scheme 2)

Step 1: Synthesis of Compound 2 (2,2'-((ethane-1, 2-diylbis(azanediyl))bis(methylene))diphenol)[18]

To a solution of ethylenediamine (0.835 mL, 12.5 mmol) in methanol (3 mL), salicylaldehyde (2.36 mL, 25 mmol) was added. A yellow precipitate was formed. The reaction mixture was heated at 80° C. for 1 h. The mixture was then cooled on an ice bath to 0° C. Next, sodium borohydride (0.88 g, 12.5 mmol) was gradually added to the mixture and the mixture was allowed to reach RT. A white precipitate was formed after stirring for 6 h. The solid was filtered and recrystallized in methanol affording 2 (2.5 g, 73%). HRMS (ESI): Calcd. for $C_{16}H_{20}N_2O_2$ [M+H$^+$] 273.1598; found 273.1602. $^1$H NMR (400 MHz, CDCl$_3$) δ 7.23-7.14 (m, 2H), 6.98 (d, J=7.1 Hz, 2H), 6.91-6.71 (m, 4H), 3.98 (s, 4H), 2.83 (s, 4H).

Step 2: Synthesis of Compound 3 (di-tert-butyl 2,2'-(ethane-1,2-diylbis((2-hydroxybenzyl) azanediyl))diacetate)

Compound 2 (0.052 g, 0.19 mmol) was dissolved in tetrahydrofuran (2 mL). To this solution disodium phosphate (0.080 g, 0.56 mmol) was added. The mixture was stirred at 0° C. and tert-butylbromoacetate (0.057 mL, 0.39 mmol) was slowly added to the mixture over 30 min. The reaction mixture was stirred at RT overnight. Next, the solvent was evaporated and an aqueous solution (10 mL, pH 8.5) was added. The product was extracted three times using equal volumes of dichloromethane. The combined organic layers were then dried with sodium sulfate and evaporated under reduced pressure. The yellow oil obtained was purified by flash chromatography on silica gel (ethyl acetate/heptane, 1:2) affording 3 (66 mg, 70%). HRMS (ESI): Calcd. for $C_{28}H_{40}N_2O_6$ [M+H$^+$] 501.2959; found 501.2979. $^1$H NMR (400 MHz, CDCl$_3$) ⌀ 7.17 (t, J=7.6 HZ, 2H), 6.87 (dd, J=20.1, 7.7 Hz, 4H), 6.76 (t, J=7.3 Hz, 2H), 3.72 (s, 4H), 3.17 (s, 4H), 2.69 (s, 4H), 1.46 (s, 18H)$^{13}$C NMR (101 MHz, CDCl$_3$) ⌀ 170.2 (2C), 157.6 (2C), 129.4 (2C), 129.3 (2C), 121.8 (2C), 119.3 (2C), 116.6 (2C), 82.2 (2C), 58.1 (2C), 55.6 (2C), 50.3 (2C), 28.3 (6C).

Step 3: Synthesis of Ligand H$_3$L2.2TFA (2,2'-(ethane-1,2-diylbis((2-hydroxybenzyl)azanediyl))diacetic Acid 2,2,2-trifluoroacetate Salt)

Compound 3 (0.066 g, 0.13 mmol) was stirred in trifluoroacetic acid (1 mL) at RT for 12 h and the deprotection was monitored using LC-MS. Afterwards the solvent was evaporated under reduced pressure and the crude product was purified using preparative HPLC (isocratic mode, 2% ACN in water) affording H$_3$L2.2TFA (20 mg, 39%). HRMS (ESI): Calcd. for $C_{20}H_{24}N_2O_6$ [M+H$^+$]389.1707; found 389.1710. $^1$H NMR (400 MHz, D$_2$O) ⌀ 7.35 (t, J=7.8 Hz, 2H), 7.29 (d, J=7.5 Hz, 2H), 7.00-6.92 (m, 4H), 4.33 (s, 4H), 3.70 (s, 4H), 3.54 (s, 4H). $^{13}$C NMR (101 MHz, D$_2$O) ⌀ 171.0, 156.1, 133.3, 132.8, 132.8, 121.4, 116.6, 116.2, 56.5, 55.5, 50.1.

Example 3: Synthesis of Ligand H$_3$L3 (FIG. 2 and Scheme 3)

Step 1: Synthesis of Compound 4 (2-(((2-(Benzylamino)ethyl)amino)methyl)phenol)[19]

A mixture of 2-hydroxybenzaldehyde (0.58 g, 4.8 mmol) and N-benzylethylenediamine (0.72 g, 4.8 mmol) in methanol (7 mL) was heated at 50° C. for 30 min. The solvent was then evaporated under reduced pressure, and the residue was suspended in ethanol (10 mL). Then, sodium borohydride (95 mg, 2.5 mmol) was added. The reaction mixture was stirred at RT for 1 h and the solvent was evaporated. Water (7 mL) was added and concentrated hydrochloric acid was used to acidify the solution to pH 1. The crystalline dihydrochloride salt was collected by filtration, washed with cold absolute ethanol and vacuum-dried to yield 4 (0.84 g, 70%). HRMS (ESI): Calcd. for $C_{16}H_{20}N_2O$ [M+H$^+$] 257.1648; found 257.1658. $^1$H NMR (400 MHz, D$_2$O) δ 7.56-7.44 (m, 5H), 7.42-7.30 (m, 2H), 7.03-6.95 (m, 2H), 4.30 (s, 4H), 3.61-3.35 (m, 4H). $^{13}$C NMR (101 MHz, D$_2$O) ⌀ 158.5, 140.4, 128.8, 128.6, 128.4, 128.2, 127.2, 122.7, 119.0, 116.5, 53.9, 52.6, 48.2, 48.1.

Step 2: Synthesis of Compound 5 (tert-butyl 2-(benzyl(2-((2-(tert-butoxy)-2-oxoethyl)(2-hydroxybenzyl)amino)ethyl)amino)acetate)

To a solution of compound 4 (0.174 g, 0.53 mmol) in tetrahydrofuran (3 mL) DIPEA (390 ⌀ L, 2.12 mmol) and tert-butyl bromoacetate (0.228 g, 1.06 mmol) were successively and slowly added at 0° C. The mixture was then stirred at RT for 12 h. The solution was filtered and the solvent removed under vacuum. The obtained oil was purified using flash chromatography on silica gel (ethyl acetate/heptane, 1:3) affording pure product 5 (0.144 g, 56%). HRMS (ESI): Calcd. for $C_{28}H_{40}N_2O_5$ [M+H$^+$] 485.3010; found 485.3028. $^1$H NMR (400 MHz, CDCl$_3$) ⌀⌀ 7.36-7.22 (m, 5H), 7.22-7.14 (m, 1H), 6.97 (m, 3H), 3.80 (s, 2H), 3.79 (s, 2H), 3.27 (s, 2H), 3.23 (s, 2H), 2.84 (t, J=6.2 Hz, 2H), 2.76 (t, J=6.1 Hz, 2H), 1.48-1.44 (m, 17H)$^{13}$C NMR (101 MHz, CDCl$_3$) ⌀ 170.7, 170.2, 157.9, 138.8, 129.3, 129.3, 128.4, 127.3, 122.1, 119.1, 116.5, 81.8, 81.1, 57.4, 55.0, 51.0, 50.9, 28.3, 28.2.

Step 3: Synthesis of Ligand H$_3$L3.2TFA (2-(benzyl (2-((carboxymethyl)(2-hydroxybenzyl)amino)ethyl) amino)acetic acid 2,2,2-trifluoroacetate Salt)

Compound 5 (0.108 g, 0.22 mmol) was stirred in trifluoroacetic acid (2 mL) at RT for 12 h. The deprotection was monitored using LC-MS. Afterwards, the solvent was evaporated under reduced pressure affording compound H$_3$L3.2TFA (0.113 g, 90% yield). HRMS (ESI): Calcd. for $C_{20}H_{24}N_2O_5$ [M+H$^+$] 373.1758; found 373.1762. $^1$H NMR (400 MHz, D$_2$O) ⌀ 7.35 (t, J=7.8 Hz, 2H), 7.29 (d, J=7.5 Hz, 2H) 7.00-6.91 (m, 5H), 4.33 (s, 4H), 3.70 (s, 4H), 3.54 (s, 4H). $^{13}$C NMR (101 MHz, D$_2$O) ⌀ 171.0, 156.1, 133.3, 132.8, 121.4, 116.6, 116.2, 56.5, 55.5, 50.1.

Example 4: Synthesis of Ligand HsL4 (FIG. 2 and Scheme 4)

Step 1: Synthesis of Compound 6 (2-(((2-(benzylamino)ethyl)amino)methyl)-4-fluorophenol)

A mixture of 5-fluoro-2-hydroxybenzaldehyde (0.093 g, 0.67 mmol) and N-benzylethylenediamine (0.100 g, 0.67 mmol) was heated in methanol (2 mL) at 50° C. for 60 min. The solvent was then evaporated under reduced pressure, and the residue was suspended in ethanol (2 mL). Then, sodium borohydride (26 mg, 0.67 mmol) was added. The reaction mixture was stirred at RT for 12 h and the solvent was evaporated. Water (2 mL) was added and concentrated hydrochloric acid was used to acidify the solution to pH 1. The crystalline dihydrochloride salt was collected by filtration, washed with cold absolute ethanol and vacuum-dried to yield 6 (0.150 g, 65%). HRMS (ESI): Calcd. for $C_{16}H_{19}FN_2O$ [M+H$^+$]275.1554; found 275.1564. $^1$H NMR (400 MHz, D$_2$O) δ 7.59-7.43 (m, 5H), 7.19-7.06 (m, 2H), 7.01-6.90 (m, 1H), 4.29 (s, 2H), 4.26 (s, 2H), 3.54-3.38 (m, 4H). $^{13}$C NMR (101 MHz, D$_2$O) ⌀158.5, 140.4, 128.8, 128.6, 128.4, 128.2, 127.2, 122.7, 119.0, 116.5, 53.9, 52.6, 48.2, 48.1. $^{19}$F NMR (376 MHz, D$_2$O) 6-124.29.

Step 2: Synthesis of Compound 7 (tert-butyl 2-(benzyl(2-((2-(tert-butoxy)-2-oxoethyl)(5-fluoro-2-hydroxybenzyl)amino)ethyl)amino)acetate)

To a solution of compound 6 (0.100 g, 0.28 mmol) in tetrahydrofuran (2 mL), N,N-diisopropylethylamine (195 ⌀ L, 1.12 mmol) and tert-butyl bromoacetate (0.114 g, 0.578 mmol) were successively and slowly added at 0° C. The mixture was then stirred at RT for 12 h. The solution was filtered and the solvent removed under vacuum. The obtained oil was purified using flash chromatography on silica gel (ethyl acetate/heptane, 1:3) affording pure product 7 (68 mg, 49%). HRMS (ESI): Calcd. for $C_{28}H_{39}FN_2O_5$ [M+H$^+$] 503.2916; found 503.2935. $^1$H NMR (400 MHz, CDCl$_3$) δ 7.35-7.20 (m, 5H), 6.90-6.82 (m, 1H), 6.77 (dd, J=8.9, 4.8 Hz, 1H), 6.64 (dd, J=8.6, 2.8 Hz, 1H), 3.78 (s, 2H), 3.74 (s, 2H), 3.26 (s, 2H), 3.22 (s, 2H), 2.82 (t, J=6.2 Hz, 2H), 2.74 (t, J=6.3 Hz, 2H), 1.45 (s, J=1.2 Hz, 18H). $^{13}$C NMR (101 MHz, CDCl$_3$) δ 170.6, 170.1, 157.2, 154.9, 153.8, 138.6, 129.3, 128.4, 127.4, 123.1, 123.0, 117.2, 117.1, 115.7, 115.4, 115.3, 115.1, 81.9, 81.1, 58.6, 56.7, 55.3, 55.0, 50.8, 50.7, 28.3, 28.2. $^{19}$F NMR (376 MHz, CDCl$_3$) δ −126.20.

Step 3: Synthesis of Ligand H$_3$L4.2TFA (2-(benzyl (2-((carboxymethyl)(5-fluoro-2-hydroxybenzyl) amino)ethyl)amino)acetic acid 2,2,2-trifluoroacetate salt)

Compound 7 (0.108 g, 0.22 mmol) was stirred in trifluoroacetic acid (2 mL) at RT for 12 h. The deprotection was monitored using LC-MS. Afterwards the solvent was evaporated under reduced pressure affording compound H$_3$L4.2TFA (0.113 g, 90%). HRMS (ESI): Calcd. for C$_{20}$H$_{23}$FN$_2$O$_5$[M+H$^+$] 391.1634; found 391.1677. $^1$H NMR (400 MHz, D$_2$O) δ 7.57-7.46 (m, 5H), 7.19-7.10 (m, 2H), 6.95 (dd, J=8.8, 4.5 Hz, 1H), 4.43 (s, 2H), 4.37 (s, 2H), 3.91 (s, 2H), 3.87 (s, 2H), 3.69-3.62 (m, 2H), 3.57-3.49 (m, 2H). $^{13}$C NMR (101 MHz, D$_2$O) δ 170.4, 170.2, 155.6, 152.5, 131.7, 131.1, 130.2, 129.4, 120.2, 119.3, 119.2, 119.1, 118.4, 117.8, 117.7, 117.3, 117.2, 67.0, 60.4, 55.5, 55.4, 55.1, 50.1. $^{19}$F NMR (376 MHz, D$_2$O) δ-75.61, −123.82.

Example 5: Synthesis of Ligand H$_3$L5 (FIG. 2 and Scheme 5)

Step 1: Synthesis of Compound 8 (2-(((2-(benzylamino)ethyl)amino)methyl)-4-nitrophenol)

A mixture of 2-hydroxy-5-nitrobenzaldehyde (0.112 g, 0.67 mmol) and N-benzylethylenediamine (0.100 g, 0.67 mmol) in methanol (2 mL) was heated at 50° C. for 60 min. The solvent was then evaporated under reduced pressure, and the residue was suspended in ethanol (2 mL). Then, sodium borohydride (0.026 g, 0.67 mmol) was added. The reaction mixture was stirred at RT for 12 h and the solvent was evaporated. Water (2 mL) was added and concentrated hydrochloric acid was used to acidify the solution to pH 2. The crystalline dihydrochloride salt was collected by filtration, washed with cold absolute ethanol and vacuum-dried to yield 8 (0.156 g, 62%). HRMS (ESI): Calcd. for C$_{16}$H$_{19}$N$_3$O$_3$ [M+H$^+$]302.1499; found 302.1498. $^1$H NMR (400 MHz, D$_2$O) δ 8.33-8.23 (m, 2H), 7.55-7.44 (m, 5H), 7.15-7.05 (m, 1H), 4.39 (s, 2H), 4.34 (s, 2H), 3.58-3.47 (m, 4H). $^{13}$C NMR (101 MHz, D$_2$O) δ 162.52, 140.85, 130.64, 130.48, 130.05, 128.78, 128.62, 118.20, 116.48, 52.27, 47.43, 43.33, 42.98.

Step 2: Synthesis of Compound 9 (tert-butyl 2-(benzyl(2-((2-(tert-butoxy)-2-oxoethyl)(2-hydroxy-5-nitrobenzyl)amino)ethyl)amino)acetate)

To a solution of compound 8 (0.104 g, 0.28 mmol) in tetrahydrofuran (2 mL), N,N-diisopropylethylamine (195 μL, 1.11 mmol) and tert-butyl bromoacetate (0.114 g, 0.58 mmol) were successively and slowly added at 0° C. The mixture was then stirred at RT for 12 h. The solution was filtered and the solvent removed in vacuum. The obtained oil was purified using flash chromatography on silica gel (ethylacetate/heptane, 1:3) affording pure product 9 (0.056 g, 38%). HRMS (ESI): Calcd. for C$_{28}$H$_{39}$N$_3$O$_7$ [M+H$^+$] 530.2861; found 530.2881. $^1$H NMR (400 MHz, CDCl$_3$) δ 8.02 (dd, J=8.9, 2.4 Hz, 1H), 7.81 (d, J=2.4 Hz, 1H), 7.28-7.14 (m, 5H), 6.81 (d, J=8.9 Hz, 1H), 3.74 (s, 2H), 3.71 (s, 2H), 3.21 (s, 2H), 3.16 (s, 2H), 2.76 (t, J=6.0 Hz, 2H), 2.67 (t, J=6.0 Hz, 2H), 1.39 (s, 9H), 1.38 (s, 9H). $^{13}$C NMR (101 MHz, CDCl$_3$) δ 170.4, 169.9, 164.3, 140.1, 138.2, 129.4, 128.5, 127.5, 125.6, 125.5, 122.4, 116.9, 82.3, 81.3, 58.6, 56.1, 55.4, 55.0, 50.7, 50.4, 28.3, 28.2.

Step 3: Synthesis of Ligand H$_3$L5.2TFA (2-(benzyl (2-((carboxymethyl)(2-hydroxy-5-nitrobenzyl) amino)ethyl)amino)acetic acid 2,2,2-trifluoroacetate salt)

Compound 9 (0.056 g, 0.11 mmol) was stirred in trifluoroacetic acid (2 mL) at RT. The deprotection was monitored using LC-MS. After 12 hours, the solvent was evaporated affording compound H$_3$L5.2TFA (31 mg, 72%). HRMS (ESI): Calcd. for C$_{20}$H$_{23}$N$_3$O$_7$ [M+H$^+$]418.1609; found 418.1618. $^1$H NMR (400 MHz, D$_2$O) δ 8.32-8.26 (m, 1H), 7.60-7.51 (m, 5H), 7.27-7.13 (m, 2H), 4.51 (s, 2H), 4.37 (s, 2H), 4.10 (s, 2H), 3.92 (s, 2H), 3.76-3.68 (m, 4H). $^{13}$C NMR (101 MHz, D$_2$O) δ 171.16, 169.89, 141.22, 131.76, 131.30, 130.34, 129.39, 128.63, 124.67, 118.65, 117.68, 117.17, 61.56, 60.62, 56.50, 50.47, 50.25, 48.85.

Example 6: Synthesis of Ligand H$_1$L6 (FIG. 2 and Scheme 6)

Step 1: Synthesis of Compound 10 (tert-butyl (2-((2-hydroxybenzyl)amino)ethyl)carbamate)

To a solution of N-Boc-ethylenediamine (988 μL, 6.24 mmol) in methanol (5.0 mL) was slowly added salicylaldehyde (732 μL, 6.87 mmol). The mixture was heated at 65° C. for 1 h, and then cooled to 0° C. Sodium borohydride (236 mg, 6.24 mmol) was added portionwise and the mixture was stirred at RT for 4 h. The solvent was then evaporated under reduced pressure. The residue was taken up in dichloromethane and an aqueous solution of sodium hydroxide (1N) was added. After five extractions with dichloromethane, the combined organic phases were dried over magnesium sulfate, filtered and evaporated under reduced pressure to give compound 10 (1.627 g, 98%) as yellow crystals. Rf (silica; dichloromethane/ethanol 95:5) 0.57; HRMS (ESI) calculated for C$_{14}$H$_{22}$N$_2$O$_3$ [M+H$^+$] 267.1703, found 267.1652); 1H NMR (400 MHz, CDCl$_3$) δ 17.15 (t, 1H, J=7.7 Hz), 6.97 (d, 1H, J=7.3 Hz), 6.73-6.84 (m, 2H), 4.89 (s, 1H), 3.98 (s, 2H), 3.26 (d, 2H, J=5.5 Hz), 2.76 (t, 2H, J=5.7 Hz), 1.43 (s, 9H); $^{13}$C NMR (101 MHz, CDCl$_3$) δ 158.1, 156.3, 128.8, 128.5, 122.4, 119.2, 116.4, 79.6, 52.4, 48.4, 40.1, 28.4 (3C).

Step 2: Synthesis of 11 (2-(((2-aminoethyl)amino) methyl)phenol (hydrochloride salt))

A solution of 10 (600 mg; 2.25 mmol) in hydrochloric acid (1 M, 10 mL) was stirred at RT overnight. The mixture was then evaporated under reduced pressure. Twice, the residue was taken up in absolute ethanol (15 mL) and evaporated under reduced pressure to give compound 11 (455 mg; 99%) as a white solid. HRMS (ESI) calculated for C$_9$H$_{14}$N$_2$O [M+H$^+$]167.1179, found 167.1190; $^1$H NMR (400 MHz, D$_2$O) δ 7.23-7.34 (m, 2H), 6.86-6.97 (m, 2H), 4.25 (s, 2H), 3.31-3.43 (m, 4H); 13C NMR (101 MHz, D$_2$O) δ 155.7, 132.5, 132.4, 121.3, 117.4, 116.3, 48.1, 44.1, 36.1.

Step 3: Synthesis of 12 (4-(((2-((2-hydroxybenzyl) amino)ethyl)amino)methyl)benzoic acid)

To a solution of 11 (370 mg; 1.83 mmol) in methanol (5.0 mL) were successively added N,N-diisopropylethylamine (318 µL; 1.83 mmol) and 4-carboxybenzaldehyde (302 mg; 2.01 mmol) portionwise. The mixture was heated at 70° C. for 1 h, and then cooled to 0° C. Sodium borohydride (69 mg; 1.83 mmol) was added portionwise and the mixture was stirred at RT for 4 h. The solvent was then evaporated under reduced pressure to give 12 as a pink oil, which was used without further purification. HRMS (ESI) calculated for $C_{17}H_{20}N_2O_3$ [M+H$^+$] 301.1547, found 301.1554; $^1$H NMR (400 MHz, MeOD-d$_4$) ☒ 7.89 (d, 2H, J=8.0 Hz), 7.34 (d, 2H, J=8.0 Hz), 7.22-7.25 (m, 2H), 6.83-6.89 (m, 2H), 4.10 (s, 2H), 3.85 (s, 2H), 3.02 (t, 2H, J=5.8 Hz), 2.91 (t, 2H, J=5.9 Hz); 13C NMR (101 MHz, MeOD-d$_4$) ☒ 174.8, 45.8, 47.1, 53.6, 55.9, 116.5, 120.5, 121.0, 129.2 (2C), 130.8 (2C), 131.9, 132.3, 138.1, 141.9, 157.7.

Step 4: Synthesis of 13 (4-(((2-(tert-butoxy)-2-oxoethyl)(2-((2-(tert-butoxy)-2-oxoethyl)(2-hydroxybenzyl)amino)ethyl)amino)methyl)benzoic Acid)

To a solution of 12 (490 mg; 1.63 mmol) in methanol (5 mL) were successively added N,N-diisopropylethylamine (853 µL; 4.89 mmol) and tert-butyl bromoacetate (482 µL; 3.26 mmol), at 0° C. The mixture was stirred at RT overnight. The solvent was then evaporated under reduced pressure. The residue was taken up in dichloromethane and an aqueous solution of sodium hydroxide (1 M) was added. After three extractions, the pH of the aqueous layer was lowered to 7 with hydrochloric acid (3 M). The aqueous layer was then evaporated under reduced pressure. The residue was taken up in methanol and the mixture stirred at RT for 1 h.

After filtration, the filtrate was evaporated under reduced pressure to give 13 as a pale-orange solid (579 mg; 68%). HRMS (ESI) calculated for $C_{29}H_{40}N_2O_7$ [M+H$^+$] 529.2908, found 529.2948; $^1$H NMR (400 MHz, MeOD-d$_4$) ☒ 7.91 (d, 2H, J=8.0 Hz), 7.27 (d, 2H, J=7.7 Hz), 7.14 (t, 1H, J=7.7 Hz), 7.04 (d, 1H, J=7.4 Hz), 6.83 (d, 1H, J=8.0 Hz), 6.76 (t, 1H, J=7.3 Hz), 3.68 (s, 2H), 3.66 (s, 2H), 3.25 (s, 2H), 3.16 (s, 2H), 2.67 (s, 4H), 1.44 (s, 18H); $^{13}$C NMR (101 MHz, MeOD-d$_4$) ☒ 175.3, 173.2 (2C), 158.8, 140.8, 138.3, 132.0, 130.4 (2C), 130.1 (2C), 127.1, 124.2, 120.1, 117.4, 83.0, 82.8, 59.4, 58.1, 57.4, 56.5, 52.6, 52.3, 28.3 (6C).

Example 7: Synthesis of Ligand H$_2$L7 (FIG. 2 and Scheme 7)

Step 1: Synthesis of 14 (N$^1$-benzyl-N$^2$-(pyridin-2-ylmethyl)ethane-1,2-diamine)

According to Dalton Trans., 2008, 7012.

To a solution of N-benzylethylenediamine (200 µL; 1.33 mmol) in methanol (5.0 mL) was slowly added 2-pyridinecarboxaldehyde (127 µL; 1.33 mmol). The mixture was then stirred at RT for 24 h. Sodium borohydride (76 mg; 2.00 mmol) was added portionwise and the mixture was stirred at RT overnight. The solvent was then evaporated under reduced pressure. The residue was taken up in dichloromethane and an aqueous solution of sodium hydroxide (0.1 M) was added. After three extractions with dichloromethane, the combined organic phases were dried over magnesium sulfate, filtered and evaporated under reduced pressure to give compound 14 (308 mg; 96%) as a yellow oil. HRMS (ESI) calculated for $C_{15}H_{19}N_3$[M+H$^+$]242.1652, found 242.1667; $^1$H NMR (400 MHz, CDCl$_3$) ☒ 8.54 (d, 1H, J=4.3 Hz), 7.62 (t, 1H, J=7.6 Hz), 7.21-7.32 (m, 6H), 7.14 (m, 1H), 3.90 (s, 2H), 3.78 (s, 2H), 2.78 (s, 4H), 2.03 (bs, 2H); $^{13}$C NMR (101 MHz, CDCl$_3$) ☒ 160.0, 149.3, 140.5, 136.5, 128.4 (2C), 128.2 (2C), 126.9, 122.3, 122.0, 55.2, 54.0, 49.1, 48.9.

Step 2: Synthesis of 15 (tert-butyl 2-(benzyl(2-((2-(tert-butoxy)-2-oxoethyl)(pyridin-2-ylmeth yl)amino)ethyl)amino)acetate)

To a solution of 14 (127 mg; 0.53 mmol) in methanol (5 mL) were successively added N,N-diisopropylethylamine (183 µL; 1.05 mmol) and tert-butyl bromoacetate (155 µL; 1.05 mmol), at 0° C. The mixture was stirred at RT overnight. The solvent was then evaporated under reduced pressure. The residue was taken up in dichloromethane and an aqueous solution of sodium hydroxide (0.1 M) was added. After three extractions with dichloromethane, the combined organic phases were dried over magnesium sulfate, filtered and evaporated under reduced pressure. The residue was purified by column chromatography (silica, DCM/EtOH 96:4) to give 15 (149 mg; 61%) as a yellow oil. Rf (silica, DCM/EtOH 95:5) 0.73; HRMS (ESI) calculated for $C_{27}H_{39}N_3O_4$ [M+H$^+$] 470.3013, found 470.3040; $^1$H NMR (400 MHz, CDCl$_3$) ☒ 8.51 (d, 1H, J=4.1 Hz), 7.61 (td, 1H, J=7.7 Hz, J=1.4 Hz), 7.50 (d, 1H, J=7.8 Hz), 7.22-7.31 (m, 5H), 7.13 (t, 1H, J=6.6 Hz), 3.92 (s, 2H), 3.77 (s, 2H), 3.34 (s, 2H), 3.23 (s, 2H), 2.82 (s, 4H), 1.45 (s, 9H), 1.44 (s, 9H); $^{13}$C NMR (101 MHz, CDCl$_3$) ☒ 171.1, 171.0, 160.1, 149.1, 139.3, 136.5, 129.1 (2C), 128.3 (2C), 127.1, 123.1, 122.0, 81.0, 80.8, 60.7, 58.5, 56.3, 55.3, 52.2, 52.0, 28.3 (6C).

Step 3: Synthesis of H$_2$L7.3TFA (2-(benzyl(2-((carboxymethyl)(pyridin-2-ylmethyl)amino)ethyl) amino)acetic acid, 2,2,2-trifluoroacetate salt)

A solution of 15 (53 mg; 0.11 mmol) in trifluoroacetic acid (5 mL) was stirred at RT overnight.

The solvent was then evaporated under reduced pressure. The residue was taken up in water (5 mL) and the solvent was evaporated under reduced pressure. The residue was then dried under vacuum to give H$_2$L7.3TFA (65 mg; 82%) as a brown oil. HRMS (ESI) calculated for $C_{19}H_{23}N_3O_4$ [M+H$^+$] 358.1761, found 358.1772; $^1$H NMR (400 MHz, D$_2$O) ☒ 8.64 (d, 1H, J=5.9 Hz), 8.48 (t, 1H, J=7.9 Hz), 7.93 (t, 1H, J=6.9 Hz), 7.83 (d, 1H, J=8.0 Hz), 7.39-7.49 (m, 5H), 4.46 (s, 2H), 4.12 (s, 2H), 4.08 (s, 2H), 3.45 (t, 2H, J=5.8 Hz), 3.41 (s, 2H), 3.13 (t, 2H, J=5.2 Hz); $^{13}$C NMR (101 MHz, D$_2$O) ☒ 175.2, 169.3, 153.1, 148.0, 141.8, 132.0 (2C), 131.2, 130.1 (2C), 128.8, 127.3, 126.9, 60.1, 55.3, 54.9, 54.4, 52.3, 50.0.

Example 8: Synthesis of Ligand H$_3$L8 (FIG. 2 and Scheme 8)

Step 1: Synthesis of 16 (tert-butyl (2-(benzyl(2-hydroxybenzyl)amino)ethyl)carbamate)

To a solution of 10 (200 mg; 0.75 mmol) in tetrahydrofuran (4 mL) were successively added potassium carbonate (104 mg; 0.75 mmol) and benzyl bromide (98 µL; 0.83 mmol) at 0° C. The mixture was stirred at RT for 7 d. After filtration and evaporation under reduced pressure, the residue was purified by column chromatography (silica, DCM/EtOH 98:2) to give 16 (192 mg; 72%) as a yellow oil. Rf (silica; dichloromethane) 0.25; HRMS (ESI) calculated for $C_{21}H_{28}N_2O_3$ [M+H$^+$] 357.2173, found 357.2183; $^1$H NMR (400 MHz, CDCl$_3$) ▒ 7.28-7.36 (m, 5H), 7.16 (td, 1H, J=7.3 Hz, J=1.3 Hz), 6.98 (d, 1H, J=7.0 Hz), 6.83 (d, 1H, J=8.0 Hz), 6.78 (t, 1H, J=7.4 Hz), 4.69 (bs, 1H), 3.78 (s, 2H), 3.68 (s, 2H), 3.30 (d, 2H, J=5.8 Hz), 2.63 (t, 2H, J=6.2 Hz), 1.41 (s, 9H); $^{13}$C NMR (101 MHz, CDCl$_3$) ▒ 158.2, 156.6, 137.3, 130.3 (2C), 129.6, 129.5, 129.4 (2C), 128.5, 122.6, 120.0, 116.9, 80.0, 59.1, 58.3, 54.2, 38.5, 29.1 (3C).

Step 2: Synthesis of 17 (2-(((2-aminoethyl)(benzyl)amino)methyl)phenol hydrochloride)

A solution of 16 (175 mg; 0.49 mmol) in hydrochloric acid (1 M, 10 mL) was stirred at RT overnight. The solvent was then evaporated under reduced pressure. The residue was twice taken up in absolute ethanol (15 mL) and the mixture evaporated under reduced pressure to give compound 17 (140 mg; 99%) as a pale-pink solid. HRMS (ESI) calculated for $C_{16}H_{20}N_2O$ [M+H$^+$] 257.1648, found 257.1663; $^1$H NMR (400 MHz, MeOD-d$_4$) ▒ 7.65 (m, 2H), 7.49 (m, 3H), 7.39 (d, 1H, J=7.5 Hz), 7.32 (t, 1H, J=8.2 Hz), 6.96 (d, 1H, J=8.1 Hz), 6.91 (t, 1H, J=7.5 Hz), 4.52 (s, 2H), 4.42 (s, 2H), 3.52 (s, 4H); 13C NMR (101 MHz, MeOD-d$_4$) ▒ 157.9, 134.1, 133.1, 132.6 (2C), 131.3, 130.4 (2C), 130.3, 121.3, 116.7, 116.6, 59.5, 54.2, 50.7, 35.4.

Step 3: Synthesis of 18 (2-((benzyl(2-((2-hydroxybenzyl)amino)ethyl)amino)methyl)phenol)

To a solution of 17 (150 mg; 0.51 mmol) in methanol (8 mL) were successively added N,N-diisopropylethylamine (178 μL; 1.02 mmol) and salicylaldehyde (60 μL; 0.56 mmol). The mixture was then heated at 70° C. for 1 h, and cooled to 0° C. Sodium borohydride (20 mg; 0.51 mmol) was added portionwise and the mixture was stirred at RT for 4 h. The solvent was then evaporated under reduced pressure. The residue was taken up in dichloromethane and an aqueous solution of sodium hydroxide (1 M) was added. After three extractions with dichloromethane, the combined organic phases were dried over magnesium sulfate, filtered and evaporated under reduced pressure to give compound 18 (163 mg; 88%) as a yellow oil. HRMS (ESI) calculated for $C_{23}H_{26}N_2O_2$ [M+H$^+$] 363.2067, found 363.2084; $^1$H NMR (400 MHz, CDCl$_3$) ▒ 7.27-7.37 (m, 5H), 7.12-7.20 (m, 2H), 6.98 (d, 1H, J=6.5 Hz), 6.72-6.86 (m, 5H), 3.78 (s, 2H), 3.76 (s, 2H), 3.63 (s, 2H), 2.79 (t, 2H, J=6.3 Hz), 2.66 (t, 2H, J=6.3 Hz); $^{13}$C NMR (101 MHz, CDCl$_3$) ▒ 158.7, 158.1, 137.1, 130.3 (2C), 129.8, 129.5, 129.5 (2C), 129.5, 129.2, 128.7, 122.8, 122.5, 120.2, 119.8, 117.1, 116.9, 59.6, 58.8, 53.2, 52.8, 46.0.

Step 4: Synthesis of H$_3$L8 (2-((2-(benzyl(2-hydroxybenzyl)amino)ethyl)(2-hydroxybenzyl)amino)acetic acid)

According to a slightly modified procedure from Baffert et al., Dalton Trans., 2003, 1765-1772.
To a solution of 18 (123 mg; 0.34 mmol) in absolute ethanol (5 mL) were successively added N,N-diisopropylethylamine (59 μL; 0.34 mmol) and bromoacetic acid (47 mg; 0.34 mmol). The solution was refluxed overnight under N$_2$. The solvent was then evaporated under reduced pressure. The residue was taken up in dichloromethane and an aqueous solution of sodium hydroxide (1 M) was added. After extractions, the pH of the aqueous layer was lowered to 6 with hydrochloric acid (1 M). The aqueous layer was then evaporated under reduced pressure. The residue was taken up in absolute ethanol. After removal of undissolved sodium chloride by filtration, the filtrate was evaporated to dryness under vacuum to give H$_3$L8 (96 mg; 68%) as a white solid. HRMS (ESI) calculated for $C_{25}H_{28}N_2O_4$ [M+H$^+$] 421.2122, found 421.2124; $^1$H NMR (400 MHz, MeOD-d$_4$) ▒ 7.13-7.39 (m, 8H), 6.79-6.86 (m, 5H), 3.98 (s, 2H), 3.77 (s, 2H), 3.73 (s, 2H), 3.19 (m, 4H), 2.89 (t, 2H, J=5.7 Hz); $^{13}$C NMR (101 MHz, MeOD-d$_4$) ▒ 157.2, 156.8, 136.6, 132.6, 132.1, 131.3, 129.9, 130.4 (2C), 129.1 (2C), 128.4, 122.1, 120.2, 120.1, 118.5, 116.0, 115.8, 58.5, 55.8, 54.2, 53.2, 51.0, 48.3.

Example 9: Synthesis of H$_3$L9 (FIG. 2 and Scheme 9)

Step 1: Synthesis of 19 (di-tert-butyl 2,2'-((2-(benzyl(2-hydroxybenzyl)amino)ethyl)azanediyl)diacetate)

To a solution of 17 (222 mg; 0.76 mmol) in methanol (5 mL) were successively added N,N-diisopropylethylamine (396 μL; 2.28 mmol) and tert-butyl bromoacetate (224 μL; 1.52 mmol), at 0° C. The mixture was stirred at RT for 24 h. The solvent was then evaporated under reduced pressure. The residue was taken up in dichloromethane and an aqueous solution of sodium hydroxide (0.1 M) was added. After three extractions with dichloromethane, the combined organic phases were dried over magnesium sulfate, filtered and evaporated under reduced pressure. The residue was purified by column chromatography (silica, DCM/EtOH 100:0→98/2) to give 19 (147 mg; 40%) as a colorless oil. Rf (silica, DCM/EtOH 98:2) 0.45; HRMS (ESI) calculated for $C_{28}H_{40}N_2O_5$ [M+H$^+$] 485.3010, found 485.3037; $^1$H NMR (400 MHz, CDCl$_3$) ▒ 7.21-7.34 (m, 5H), 7.15 (t, 1H, J=7.1 Hz), 7.00 (d, 1H, J=7.1 Hz), 6.84 (d, 1H, J=8.0 Hz), 6.76 (t, 1H, J=7.3 Hz), 3.80 (s, 2H), 3.62 (s, 2H), 3.32 (s, 4H), 2.96 (t, 2H, J=6.8 Hz), 2.61 (t, 2H, J=6.8 Hz), 1.41 (s, 18H); $^{13}$C NMR (101 MHz, CDCl$_3$) ▒ 170.3 (2C), 157.7, 137.2, 129.7 (2C), 129.2, 128.8, 128.6 (2C), 127.6, 122.5, 119.1, 116.3, 81.1 (2C), 58.5, 57.0, 55.8 (2C), 50.8, 50.5, 28.2 (6C).

Step 2: Synthesis of H$_3$L9.2TFA (2,2'-((2-(benzyl(2-hydroxybenzyl)amino)ethyl)azanediyl)diacetic Acid, 2,2,2-trifluoroacetate Salt)

A solution of 19 (111 mg; 0.23 mmol) in trifluoroacetic acid (5 mL) was stirred at RT overnight. The solvent was then evaporated under reduced pressure. The sample was taken up in water (5 mL) and the solvent was evaporated under reduced pressure. The residue was then dried under vacuum to give HsL9.2TFA (90 mg; 70%) as a pale-pink gum. HRMS (ESI) calculated for $C_{20}H_{24}N_2O_5$ [M+H$^+$] 373.1758, found 373.1780; $^1$H NMR (400 MHz, D$_2$O) ▒ 7.38 (s, 5H), 7.26 (t, 1H, J=7.7 Hz), 7.15 (d, 1H, J=7.4 Hz), 6.83-6.88 (m, 2H), 4.29 (s, 2H), 4.16 (s, 2H), 3.26 (s, 4H), 3.22 (t, 2H, J=5.6 Hz), 3.02 (t, 2H, J=5.5 Hz); $^{13}$C NMR (101 MHz, D$_2$O) ▒ 174.0 (2C), 155.9, 133.1, 132.7, 131.7 (2C), 130.8, 129.9 (2C), 129.4, 121.3, 116.6, 116.3, 59.0, 54.9, 54.4 (2C), 50.3, 49.2.

Example 10: Synthesis of Ligand H$_2$L10 (FIG. 2 and Scheme 10)

Step 1: Synthesis of 20 (tert-butyl (2-((2-(benzyl(2-hydroxybenzyl)amino)ethyl)(2-hydroxybenzyl)amino)ethyl)carbamate)

To a solution of 18 (151 mg; 0.42 mmol) in dry tetrahydrofuran (5 mL) were successively added N,N-diisopropylethylamine (218 μL; 1.25 mmol) and 2-(Boc-amino)ethyl bromide (103 mg; 0.46 mmol) at 0° C. The mixture was stirred at RT for 5 d, then at 50° C. for 8 d. Then 2 more equivalents of N,N-diisopropylethylamine were added and the mixture was stirred at 50° C. for 7 d. The solvent was evaporated under reduced pressure. The residue was taken up in dichloromethane and an aqueous solution of sodium hydroxide (0.1 M) was added. After three extractions with dichloromethane, the combined organic phases were dried over magnesium sulfate, filtered and evaporated under reduced pressure. The residue was purified by column chromatography (silica, n-heptane/ethyl acetate 75:25) to give 20 (31 mg; 15%) as a pale-yellow oil. Rf (silica, n-heptane/ethyl acetate 75:25) 0.25; HRMS (ESI) calculated for $C_{30}H_{39}N_3O_4$ [M+H$^+$] 506.3013, found 506.3028; $^1$H NMR (400 MHz, CDCl$_3$) ⏃ 7.13-7.35 (m, 8H, H—Ar), 6.74-6.96 (m, 5H, H—Ar), 3.73 (s, 2H), 3.65 (s, 2H), 3.58 (s, 2H), 3.18 (m, 2H), 2.71 (s, 4H), 2.51 (t, 2H, J=5.5 Hz), 1.41 (s, 9H); $^{13}$C NMR (101 MHz, CDCl$_3$) ⏃ 157.5, 157.4, 156.1, 136.1, 129.8 (2C), 129.2, 129.2, 129.0, 128.9, 128.8 (2C), 128.0, 121.7, 121.6, 119.6, 119.6, 116.4, 116.3, 79.6, 58.5, 58.1, 53.8 (2C), 51.0, 50.1, 38.0, 28.5 (3C).

Step 2: Synthesis of H$_2$L10.3HCl (2-(((2-amino-ethyl)(2-(benzyl(2-hydroxybenzyl)amino)ethyl) amino)methyl)phenol hydrochloride)

A solution of 20 (31 mg; 61 μmol) in hydrochloric acid (1 M, 5 mL) was stirred at RT overnight.
The solvent was then evaporated under reduced pressure. The sample was taken up in absolute ethanol (2×15 mL) and evaporated under reduced pressure to give compound H$_2$L10.3HCl (27 mg; 99%) as a pale-pink oil. HRMS (ESI) calculated for $C_{25}H_{31}N_3O_2$ [M+H$^+$]406.2489, found 406.2494; $^1$H NMR (400 MHz, MeOD-d$_4$) ⏃ 7.63 (m, 2H), 7.48 (m, 3H), 7.30-7.39 (m, 4H), 6.88-6.97 (m, 4H), 4.54 (s, 2H), 4.44 (s, 2H), 4.41 (s, 2H), 3.84 (s, 4H), 3.67 (m, 2H), 3.55 (m, 2H); $^{13}$C NMR (101 MHz, MeOD-d$_4$) ⏃ 157.9, 157.7, 134.2, 134.0, 133.5, 133.2, 132.6 (2C), 131.4, 130.5 (2C), 130.2, 121.5, 121.4, 116.9, 116.7, 116.6, 115.9, 59.9, 55.0, 54.5, 52.1, 49.9, 49.4, 35.4.

Example 11: Synthesis of Ligand H$_2$L11 (FIG. 2 and Scheme 11)

Step 1: Synthesis of 21 (N$^1$-benzyl-N$^2$-(pyridin-3-ylmethyl)ethane-1,2-diamine)

To a solution of N-benzylethylenediamine (200 μL; 1.33 mmol) in methanol (5.0 mL) was slowly added 3-pyridinecarboxaldehyde (127 μL; 1.33 mmol). The mixture was then stirred at RT for 24 h. Sodium borohydride (76 mg; 2.00 mmol) was added portionwise and the mixture was stirred at RT overnight. The solvent was then evaporated under reduced pressure. The residue was taken up in dichloromethane and an aqueous solution of sodium hydroxide (0.1 M) was added. After three extractions with dichloromethane, the combined organic phases were dried over magnesium sulfate, filtered and evaporated under reduced pressure to give compound 21 (314 mg; 98%) as a yellow oil. HRMS (ESI) calculated for $C_{15}H_{19}N_3$[M+H$^+$]242.1652, found 242.1672; $^1$H NMR (400 MHz, CDCl$_3$) ⏃ 8.53 (s, 1H), 8.47 (d, 1H, J=4.6 Hz), 7.64 (d, 1H, J=7.7 Hz), 7.29 (m, 4H), 7.20-7.23 (m, 2H), 3.76 (s, 2H), 3.75 (s, 2H)), 2.74 (s, 4H), 1.76 (bs, 2H); $^{13}$C NMR (101 MHz, CDCl$_3$) ⏃ 149.6, 148.3, 140.4, 135.7, 135.7, 128.3 (2C), 128.0 (2C), 126.9, 123.3, 53.8, 51.1, 48.7, 48.6.

Step 2: Synthesis of 22 (tert-butyl 2-(benzyl(2-((2-(tert-butoxy)-2-oxoethyl)(pyridin-3-ylmethyl)amino) ethyl)amino)acetate)

To a solution of 21 (147 mg; 0.61 mmol) in methanol (5 mL) were successively added N,N-diisopropylethylamine (212 μL; 1.22 mmol) and tert-butyl bromoacetate (180 μL; 1.22 mmol), at 0° C. The mixture was stirred at RT overnight. The solvent was then evaporated under reduced pressure. The residue was taken up in dichloromethane and an aqueous solution of sodium hydroxide (0.1 M) was added. After three extractions with dichloromethane, the combined organic phases were dried over magnesium sulfate, filtered and evaporated under reduced pressure. The residue was purified by column chromatography (silica, DCM/EtOH 96:4) to give 22 (154 mg; 54%) as a yellow oil. Rf (silica, DCM/EtOH 96:4) 0.39; HRMS (ESI) calculated for $C_{27}H_{39}N_3O_4$ [M+H$^+$] 470.3013, found 470.3058; $^1$H NMR (400 MHz, CDCl$_3$) ⏃ 8.48-8.51 (m, 2H), 7.69 (d, 1H, J=7.8 Hz), 7.21-7.30 (m, 6H), 3.79 (s, 2H), 3.77 (s, 2H), 3.25 (s, 2H), 3.24 (s, 2H), 2.79 (s, 4H), 1.45 (s, 18H, (CH$_3$)$_3$); $^{13}$C NMR (101 MHz, CDCl$_3$) ⏃ 170.9, 170.7, 150.2, 148.6, 139.1, 136.8, 134.8, 129.0 (2C), 128.3 (2C), 127.1, 123.4, 81.0, 80.8, 58.5, 55.7, 55.3, 55.2, 51.7, 51.7, 28.3 (3C), 28.3 (3C).

Step 3: Synthesis of H$_2$L11.3TFA (2-(benzyl(2-((carboxymethyl)(pyridin-3-ylmethyl)amino)ethyl) amino)acetic acid, 2,2,2-trifluoroacetate salt)

A solution of 22 (60 mg; 0.13 mmol) in trifluoroacetic acid (5 mL) was stirred at RT overnight.
The solvent was then evaporated under reduced pressure. The sample was then taken up in water (5 mL) and the solvent was evaporated under reduced pressure. The residue was then dried under vacuum to give H$_2$L11.3TFA (89 mg; 99%) as a yellow oil. HRMS (ESI) calculated for $C_{19}H_{23}N_3O_4$ [M+H$^+$] 358.1761, found 358.1786; $^1$H NMR (400 MHz, D$_2$O) ⏃ 8.56 (d, 1H, J=5.7 Hz), 8.41 (s, 1H), 8.21 (d, 1H, J=8.2 Hz), 7.86 (dd, 1H, J=8.0 Hz, J=5.9 Hz), 7.37-7.40 (m, 2H), 7.26 (m, 3H), 4.35 (s, 2H), 4.07 (s, 2H), 3.75 (s, 2H), 3.40 (t, 2H, J=5.7 Hz), 3.20 (s, 2H), 2.96 (t, 2H, J=5.7 Hz); $^{13}$C NMR (101 MHz, D$_2$O) ⏃ 175.1, ⏃ 169.1, 147.6, 141.0, 141.0, 138.3, 131.8 (2C), 131.2, 130.1 (2C), 129.1, 128.0, 60.7, 54.9, 54.3, 54.1, 52.0, 49.6.

Example 12: Synthesis of Ligand H$_2$L12 (FIG. 2 and Scheme 12)

Step 1: Synthesis of Compound 23 (tert-butyl N-{2-[benzyl({2-[(tert-butoxycarbonyl)amino] ethyl})amino]ethyl}carbamate)

To a solution of 1,7-bis-boc-1,4,7-triazaheptane (0.229 g, 0.76 mmol) in tetrahydrofuran (2 mL), potassium carbonate (0.156 g; 1.13 mmol) and benzyl bromide (0.259 g; 1.51 mmol) were successively and slowly added at 0° C. The mixture was then stirred at RT overnight. The solution was filtered and the solvent removed under vacuum. The obtained oil was purified using flash chromatography on silica gel using a gradient of heptane (A) and ethyl acetate (B) (0-1 min: 0% B, 1-9 min: linear gradient 0% B to 80% B) at a flow rate of 15 mL/min affording pure product 23 (0.236 g; 80%). HRMS (ESI): Calcd. for $C_{21}H_{35}N_3O_4$ [M+H$^+$] 394,2700; found 394.2698. $^1$H NMR (400 MHz, CDCl$_3$) δ 7.39-7.18 (m, 5H), 3.58 (s, 2H), 3.20 (br. s, 4H), 2.55 (br. s, 4H), 1.45 (s, 18H). $^{13}$C NMR (101 MHz, CDCl$_3$) δ 156.27, 128.93, 128.34, 127.15, 79.09, 58.67, 53.75, 38.27, 28.46.

Step 2: Synthesis of Compound H$_2$L12 (2-[({2-[benzyl(2-{[(2-hydroxyphenl)methyl]amino}ethyl)amino]ethyl}amino)methyl)phenol)

Compound 23 (0.236 g; 0.60 mmol) was stirred in trifluoroacetic acid (2 mL) at RT. The deprotection was monitored using LC-MS and after 2 hours, the deprotection was complete. The solvent was removed under vacuum and the residue was washed three times with dichloromethane. Salicylaldehyde (0.41 g; 3.32 mmol) and methanol (7 mL) were added and the reaction mixture was heated at 50° C. for 60 min. Then, sodium borohydride (95 mg; 2.5 mmol) was slowly added at 0° C. and the mixture was stirred at RT overnight. The solvent was then evaporated under reduced pressure. The residue was taken up in dichloromethane and an aqueous solution of sodium hydroxide (0.1 M) was added. After three extractions with dichloromethane, the combined organic phases were dried over magnesium sulfate, filtered and evaporated under reduced pressure. The residue was dissolved in a minimal volume of hot methanol and the mixture immediately filtered. The filtrate was placed in an ice bath and after a short period of time crystals started to form. The filtrate was stored at 6° C. overnight to complete the crystallization. The crystals were filtered off and washed twice with ice-cold methanol (2×30 mL), affording pure H$_2$L12 (0.153 g; 0.38 mmol) with 63% yield. HRMS (ESI): Calcd. for C$_{25}$H$_{31}$N$_3$O$_2$ [M+H$^+$] 406.2489; found 406,2496.

$^1$H NMR (400 MHz, MeOD) δ 7.36-7.18 (m, 5H), 7.06 (br. t, J=7.7 Hz, 2H), 6.96 (d, J=7.2 Hz, 2H), 6.79-6.67 (m, 4H), 3.71 (s, 4H), 3.45 (s, 2H), 2.64-2.56 (m, 4H), 2.56-2.49 (m, 4H). $^{13}$C NMR (101 MHz, MeOD) δ 158.65, 140.23, 130.53, 130.23, 129.63, 129.38, 128.15, 124.84, 119.90, 116.76, 60.11, 54.00, 51.33, 46.62.

Example 13: Synthesis of Ligand H$_3$L13 (FIG. 2 and Scheme 13)

Step 1: Synthesis of Compound 24 (N$^1$,N$^2$-ditosylethane-1,2-diamine)

Toluene-4-sulfonyl chloride (13.84 g, 72.6 mmol) in diethyl ether (100 mL) was added to a solution of 1,2-diaminoethane (2.07 g, 34.5 mmol) in water (80 mL) and NaOH (2.84 g, 71.0 mmol) at RT. The reaction mixture was stirred at RT for 17 h and then diethyl ether (50 mL) was added and the mixture was filtered. The solid was washed with water followed by diethyl ether. The product was dried to afford compound 24 as a white solid (10.88 g, 85%). HRMS (ESI): Calcd. for C$_{16}$H$_{20}$N$_2$O$_4$S$_2$[M+H$^+$] 369.0937; found 369.0952. $^1$H NMR (400 MHz, DMSO) δ 7.60 (d, J=8.0 Hz, 4H), 7.37 (d, J=8.0 Hz, 4H), 3.34 (s, 6H), 2.70 (s, 2H), 2.38 (s, 4H). $^{13}$C NMR (101 MHz, DMSO) δ 142.74, 137.34, 129.66, 126.46, 42.13, 20.96.

Step 2: Synthesis of Compound 25 (1,4-ditosyl-1,4-diazepan-6-ol)

A mixture of compound 24 (6.73 g, 18 mmol) and sodium methoxide (1,966 g, 37 mmol) in absolute ethanol (100 mL) was refluxed for 30 min. The solution was allowed to cool and 1,3-dibromopropan-2-ol (4.34 g, 18 mmol) in absolute ethanol (20 mL) was added. The mixture was stirred under reflux for 6 hr. The mixture was cooled after the addition of water (50 mL) and the pH of the solution adjusted to 10 with a concentrated solution of NaOH. The white precipitate that formed after 3 days in the freezer was filtered and washed with water. The crude solid contained a mixture of compounds identified as starting material and compound 25. The white solid was stirred in NaOH solution (10% m/V, 10 mL per g of impure material) on a steam bath (2 h) and the undissolved solid was filtered while the mixture was still hot. The white solid was washed with water. The residual solvent was removed under vacuum affording compound 25 (3 g, 40%). HRMS (ESI): Calcd. for C$_{19}$H$_{24}$N$_2$O$_5$S$_2$[M+H$^+$] 425.1199; found 425.1212. $^1$H NMR (400 MHz, Acetone) δ 7.72 (d, J=8.1 Hz, 4H), 7.43 (d, J=8.1 Hz, 4H), 4.14-3.86 (m, 1H), 3.67-3.47 (m, 4H), 3.41-3.25 (m, 2H), 3.24-3.00 (m, 2H), 2.43 (s, 6H). $^{13}$C NMR (101 MHz, Acetone) δ 144.39, 137.41, 130.70, 127.88, 70.05, 54.82, 51.57, 21.39.

Step 3: Synthesis of Compound 26 (1,4-diazepan-6-yl acetate dihydrobromide)

A solution of 25 (1 g 2.34 mmol) and acetic anhydride (0.238 g, 2.34 mmol) in 30% anhydrous solution of hydrogen bromide in acetic acid (15 mL) was stirred at room temperature for 30 min. Then phenol (0.886 g, 9.36 mmol) was added, and the reaction mixture was stirred at 60° C. for 6 h and allowed to cool to room temperature overnight. Solvents were removed at 70° C. under vacuum to give an oil which, after trituration with dry diethyl ether and stirring with 5 mL of absolute ethanol, afforded product 26 (0.596 g, 80%). HRMS (ESI): Calcd. for C$_{17}$H$_{14}$N$_2$O$_2$ [M+H*] 159.1128; found 159.1140. $^1$H NMR (400 MHz, D$_2$O) δ 3.98-3.54 (m, 9H), 2.22 (s, 3H). $^{13}$C NMR (101 MHz, D$_2$O) δ 150.92, 44.42, 26.81, 22.41.

Step 4: Synthesis of Compound 27 (1,4-ditert. butylacetat)1,4-diazepan-6yl acetate)

To a suspension of 26 (0.10 g, 0.31 mmol) and K$_2$CO$_3$ (0.086 g, 0.625 mmol) in dry acetonitrile (2 mL), tert-butyl bromoacetate (0.121 g, 0.625 mmol) was added and the mixture was allowed to react for 12 h at room temperature. Then, saturated solution of NaHCO$_3$ (10 mL) was added and the mixture was extracted with dichloromethane (3×10 mL). The combined organic layers were dried over anhydrous Na$_2$SO$_4$, filtered and concentrated under reduced pressure. The resulting oil was purified by flash column chromatography on SiO$_2$ (ethyl acetate) affording compound 27. (30 mg, 20%) HRMS (ESI): Calcd. for C$_{19}$H$_{34}$N$_2$O$_6$ [M+H$^+$] 387.1428; found 387.1430. $^1$H NMR (400 MHz, CDCl$_3$) δ 4.91 (dd, J=10.7, 5.2 Hz, 1H), 3.36 (s, 4H), 3.17 (dd, J=14.2, 4.9 Hz, 2H), 2.95 (dd, J=14.3, 5.8 Hz, 2H), 2.88 (s, 4H), 2.05 (s, 3H), 1.44 (s, 18H). $^{13}$C NMR (101 MHz, CDCl$_3$) δ 170.82, 170.57, 81.24, 72.59, 60.75, 58.29, 56.54, 28.32, 21.45.

Step 5: Synthesis of Compound 28 (1,4-diacetic acid)1,4-diazepan-6yl acetate)

Compound 27 (30 mg, 0.071 mmol) was stirred at RT in 2 mL of TFA. The reaction was monitored by LC-MS. The solvent was removed under vacuum and diethyl ether was added. Compound 28 was isolated as a white powder after trituration. HRMS (ESI): Calcd. for C$_{11}$H$_{18}$N$_2$O$_6$ [M+H$^+$] 275.1165; found 275.1140. $^1$H NMR (400 MHz, D$_2$O) δ

5.55 (s, 1H), 4.10 (s, 4H), 3.97-3.71 (m, 8H), 2.25 (s, 3H). $^{13}$C NMR (101 MHz, D$_2$O) δ 172.15, 169.73, 65.97, 58.61, 56.70, 52.28, 20.96.

Step 6: Synthesis of Compound H$_3$L13 (1,4-diacetic acid)1,4-diazepan-6-ol)

Compound 28 was refluxed in 2 mL of water. The cleavage of the acyl group was followed by LC-MS. When the reaction was complete the solvent was removed under reduced pressure to afford pure H$_3$L13. $^1$H NMR (400 MHz, D$_2$O) δ 4.65-4.56 (m, 1H), 4.18 (s, 3H), 4.12-4.03 (m, 2H), 4.02-3.81 (m, 4H), 3.69 (d, J=14.1 Hz, 2H). $^{13}$C NMR (101 MHz, D$_2$O) δ 168.88, 62.25, 58.71, 58.65, 51.45.

Example 14: Identification of Reference Compounds, Al$^{19}$F-L$_n$

Na$^{19}$F (42 mg, 1 mmol) was added to an aqueous solution of AlCl$_3$ (1 M, 1 mL). The pH was adjusted to 4 using an aqueous solution of sodium hydroxide (0.1 M) and the mixture was stirred for 10 min. Then, an aqueous solution of the corresponding ligand (1 M, 1 mL) was slowly added and the mixture was heated at 40° C. for 1 h. The reaction was monitored by LC-MS. Al$^{19}$F-L1, HRMS (ESI): Calcd. for C$_{15}$H$_{17}$AlFN$_2$O$_6^-$ [M]$^-$ 367.0892; found 367.0862. Al$^{19}$F-L2, HRMS (ESI): Calcd. for C$_{20}$H$_{21}$AlFN$_2$O$_6^-$ [M]$^-$ 431,1205; found 431.1210. Al$^{19}$F-L3, HRMS (ESI): Calcd. for C$_{20}$H$_{21}$AlF N$_2$O$_5^-$ [M]$^-$ 415.1255; found 415.1262. Al$^{19}$F-L4, HRMS (ESI): Calcd. for C$_{20}$H$_{21}$AlF$_2$N$_2$O$_5^-$ [M]$^-$ 433.1115; found 433.1162. Al$^{19}$F-L5, HRMS (ESI): Calcd. for C$_{20}$H$_{21}$AlFN$_3$O$_7^-$ [M]$^-$ 460.1059; found 460.1099. Al$^{19}$F-L7, HRMS (ESI): Calcd. for C$_{19}$H$_{21}$AlFN$_3$O$_4$ [M+H]$^+$ 402.1407; found 402.1397. Al$^{19}$F-NODA, HRMS (ESI): Calcd. for C$_{17}$H$_{23}$AlFN$_3$O$_4$[M+H$^+$]379.1488; found 379.1470.

Example 15: Complexation of {Al$^{18}$F}$^{2+}$

Production of Aqueous Solution of [$^{18}$F]Fluoride and {Al$^{18}$F}$^{2+}$

After cyclotron production, [$^{18}$F]F$^-$ was separated from [$^{18}$O]H$_2$O by trapping on a SepPak™ Light Accel plus QMA anion exchange cartridge (Cl$^-$ form; Waters, Milford, USA). The [$^{18}$F]F$^-$ (148-333 MBq) was eluted from the cartridge with an aqueous solution of sodium chloride 0.9% (0.4 mL). This aqueous solution of [$^{18}$F]fluoride (50 µl) was added to 22.5 µl of 2 mM aluminum chloride (AlCl$_3$) in sodium acetate buffer (0.1 M, pH 4). The solution was incubated at RT for 10 min to form {A $^{18}$F}$^{2+}$.

Production and Purification of [Al$^{18}$F]-Complexes

A solution of each ligand (1 mL, 150 µM) in sodium acetate buffer (0.1 M, pH 4) was added to a vial which contained a freshly prepared {Al$^{18}$F}$^{2+}$ solution. The vials were heated at different temperatures for 12 min and the radiochemical yields were determined by iTLC-SG.

The resulting mixtures were purified with a Sep-Pak® Plus Alumina-N-Cartridge (Waters, Milford, USA). The cartridge was pre-rinsed with an aqueous solution of sodium chloride 0.9% (5 mL) and the crude reaction mixture was loaded on the column. The cartridge was then rinsed with an aqueous solution of sodium chloride 0.9% (3 mL). The eluate was collected and each of the purified ligand-[Al$^{18}$F]$^{2+}$ complex solutions was analysed using iTLC-SG.

Results on Complexation with {Al$^{18}$F}$^{2+}$

Al$^{18}$F-L1

H$_3$L1 was labeled with {Al$^{18}$F}$^{2+}$ in a non-optimized yield of 96% (12 min 40° C., pH 4). Radio-HPLC-HRMS confirmed the presence of the aluminum fluoride complex (ESI-MS (m/z): found, 367.0851 [M]$^-$ calculated for C$_{15}$H$_{17}$AlFN$_2$O$_6$ 367.0881), and the aluminum hydroxide complex (similar complex in which the fluoride ion is replaced by an hydroxide ion) (ESI-MS (m/z): found, 365.0935 [M]$^-$ calculated for C$_{15}$H$_{18}$AlN$_2$O$_7$ 365.0929.

Al$^{18}$F-L2

H$_3$L2 was labeled with {Al$^{18}$F}$^{2+}$ in a non-optimized yield of 96% (12 min 40° C., pH 4). Radio-HPLC-HRMS confirmed the presence of the aluminum fluoride complex (ESI-MS (m/z): found, 431.0751 [M]$^-$ calculated for C$_{20}$H$_{21}$AlFN$_2$O$_6$ 431.1194), an aluminum complex (ESI-MS (m/z): found, 411.1008 [M]$^-$ calculated for C$_{20}$H$_{20}$AlN$_2$O$_6$ 411.1131) and the free chelator (ESI-MS (m/z): found, 387.1166 [M–H]$^-$ calculated for C$_{20}$H$_{24}$N$_2$O$_6$ 387.1551).

Al$^{18}$F-L3

H$_3$L3 was labeled with {Al$^{18}$F}$^{2+}$ in a non-optimized yield of 89% (12 min 40° C., pH 4). Radio-HPLC-HRMS confirmed the presence of the aluminum fluoride complex (ESI-MS (m/z): found, 415.1217 [M]$^-$ calculated for C$_{20}$H$_{21}$AlFN$_2$O$_5$ 415.1244), an aluminum hydroxide complex (ESI-MS (m/z): found, 413.1141 [M]$^-$ calculated for C$_{20}$H$_{22}$AlN$_2$O$_6$ 413.119) and the free chelator (ESI-MS (m/z): found, 371.1587 [M–H]$^-$ calculated for C$_{20}$H$_{24}$N$_2$O$_5$ 371.1512).

Al$^{18}$F-L4

H$_3$L4 was labeled with {Al$^{18}$F}$^{2+}$ in a non-optimized yield of 92% (12 min 40° C., pH 4). Radio-HPLC-HRMS confirmed the presence of the aluminum fluoride complex (ESI-MS (m/z): found 433.1162 [M]$^-$ calculated for C$_{20}$H$_{21}$AlF$_2$N$_2$O$_5$ 433.1115) and an aluminum hydroxide complex (ESI-MS (m/z): found, 431.1203 [M]$^-$ calculated for C$_{20}$H$_{22}$AlFN$_2$O$_6$ 431.1194).

Al$^{18}$F-L5

H$_3$L5 was labeled with {Al$^{18}$F}$^{2+}$ in a non-optimized yield of 56% (12 min 40° C., pH 4). Radio-HPLC-HRMS confirmed the presence of the aluminum fluoride complex (ESI-MS (m/z): found, 460.1099 [M]$^-$ calculated for C$_{20}$H$_{21}$AlFN$_3$O$_7$ 460.1113) and an aluminum hydroxide complex (ESI-MS (m/z): found, 458.1154 [M]$^-$ calculated for C$_{20}$H$_{22}$AlN$_3$O$_8$ 458.1139).

Al$^{18}$F-L7

H$_2$L7 was labeled with {Al$^{18}$F}$^{2+}$ in a non-optimized yield of 94% (12 min 80° C., pH 4). Radio-HPLC-HRMS confirmed the presence of the aluminum fluoride complex (ESI-MS (m/z): found, 402.1397 [M+H] calculated for C$_{19}$H$_{21}$AlFN$_3$O$_4$ 402.1407), and an aluminum hydroxide complex (ESI-MS (m/z): found, 400.1405 [M+H] calculated for C$_{20}$H$_{22}$AlN$_3$O$_5$ 400.1448).

Al$^{18}$F-L9

H$_3$L9 was labeled with {Al$^{18}$F}$^{2+}$ in a non-optimized yield of 8% (12 min 110° C., pH 4), determined with iTLC-SG. Radio-HPLC-HRMS could not confirm the presence of the aluminum fluoride complex, probably because the complex is not stable under the used conditions.

Al$^{18}$F-L8, Al$^{18}$F-L10, Al$^{18}$F-L12, Al$^{18}$F-L13

H$_3$L8, H$_2$L10, H$_2$L12, and H$_3$L13 were not able to complex [Al$^{18}$F]$^{2+}$.

The radiochemical yields (RCY's) derived from iTLC-SG analyses at different temperatures are represented in FIG. 3. The RCY's obtained with NODA-Benzyl (FIG. 2) are also displayed in the graphic and it is clear that Al$^{18}$F-NODA-benzyl is only formed at temperatures higher than 100° C. getting a yield of 79%. H$_3$L1 showed efficient chelation of {Al$^{18}$F}$^{2+}$ at all tested temperatures with RCY's higher than 80%. The major difference in reactivity of this ligand with respect to the other evaluated ligands was observed at room temperature where H$_3$L1 had a non-optimized RYC of 92%. Yields after reaction at room temperature for 12 minutes were 36%, 31%, 44%, 49% and 4% for H$_2$L2, H$_3$L3, H$_3$L4, H$_3$L5 and H$_2$L7, respectively. For H$_3$L3, H$_3$L4 and H$_3$L5 minor differences in RCY's at temperatures between 40 and 100° C. were observed. H$_3$L2 was the only ligand that did not chelate {Al$^{18}$F}$^{2+}$ at 110° C. while H$_3$L1, H$_3$L3, H$_3$L4, H$_3$L5 and H$_2$L7 gave RCY's of 84%, 72%, 85%, 62% and 93%, respectively. For H$_2$L7 good RCY's of <85% were observed at temperatures starting from 60° C. The ligand H$_3$L9 was labeled with {Al$^{18}$F}$^{2+}$ in a non-optimized yield of 8% (12 min 110° C., pH 4). The ligands H$_3$L8, H$_2$L10, H$_2$L12, and H$_3$L13 were not able to complex [Al$^{18}$F]$^{2+}$.

All complexes had >95% radiochemical purity (RCP) after Alumina-N cartridge purification. FIG. 4 shows the iTLC-SG analysis of [Al$^{18}$F]-L3 before and after alumina-N-cartridge purification. The radiochemical purity after purification was 98.3%.

Example 16: Semi Automated Radiosynthesis and Purification of [Al$^{18}$F]-L3

To assess the efficiency of the labeling agent in a more realistic setting, the process for radiosynthesis and purification of [Al$^{18}$F]-L3 was performed semi-automatically. [$^{18}$F] fluoride was produced and trapped on a SepPak™ Light Accel plus QMA anion as described previously. The [$^{18}$F]F$^-$ was eluted from the cartridge with an aqueous solution of sodium chloride 0.9% (0.2 mL) and added to 22.5 µl of 20 mM aluminum chloride (AlCl$_3$) in sodium acetate buffer (0.1 M, pH 4). The solution was incubated at RT for 10 min to form {Al$^{18}$F}$^{2+}$. A solution of H$_3$L3 (0.5 mL, 1.5 mM) was added and the reactor was heated at 40° C. for 12 min. After dilution with water (0.5 mL), the crude reaction mixture was injected onto a semi-preparative HPLC column (XBridge C$_{18}$, 5 µm, 4.6 mm×150 mm, Waters) eluted with EtOH: sodium acetate 0.05M pH 5.5, 8:92 (v/v) at a flow rate of 1 mL/min. UV detection of the eluate was performed at 254 nm. Identification of the [Al$^{18}$F]-L3 complex was done by radio-LC-HRMS (Acquity UPLC BEH C18, 1.7 µm, 2.1 mm×150 mm, Waters. 0.6 mL/min A: H$_2$O B: ACN, 0-2 min 5% B, 2 to 8 min 5% B to 95% B, 8-10 min 95% B, 10 to 12 min 95% B to 5% B).

H$_3$L3 was labeled with {Al$^{18}$F}$^{2+}$ in a non-optimized yield of 74% (12 min 40° C., pH 4). The batch (4.63 GBq) was produced with a RCP higher than 98% in 35 min starting after elution of fluorine-18. FIG. 5 shows the radio-LC-HRMS analysis of [Al$^{18}$F]-L3 after purification with preparative RP-HPLC. Chromatogram A is the radiometric signal and chromatogram B is an extracted ion chromatogram of the Al$^{19}$F-L3-complex. The radio-HPLC-HRMS confirms the presence of the expected aluminum fluoride complex (C). The retention times of all Al$^{18}$F-complexes were the same as those of their homologous cold 19F complexes. Finally, the stability test on the batch showed that more than 95% of [Al$^{18}$F]-L3 was still intact after incubation at room temperature for 2 hours.

Example 17: Effect of pH

A solution (1 mL, 150 µM) of each ligand was prepared in sodium acetate buffer (0.1 M) at different pH, ranging from pH 3 to pH 5.5. The solution was added to a vial which contained a freshly prepared {Al$^{18}$F}$^{2+}$ solution. The vials were heated at 40° C. for 12 min and the radiochemical yields were determined by iTLC-SG.

The radiochemical yields at different pH as shown by iTLC-SG are represented in FIG. 6. The optimal pH range for labeling H$_3$L3, H$_3$L4 and H$_3$L5 was between 4 and 5, but even at pH 5.5 high RCY's were observed. When the labeling was performed under pH 4, the RCY's were decreasing rapidly.

Example 18: Effect of H$_3$L3/AlCl$_3$ ratio

Different stock solutions of AlCl$_3$ in sodium acetate buffer (0.1 M, pH 4) were prepared: 2000, 1000, 500, 100, 50, 25 and 10 µM. From these solutions 22.5 µl was added to Na$^{18}$F (50 µl) and the solution was incubated at RT for 10 min to form {Al$^{18}$F}$^{2+}$. Different stock solutions of H$_3$L3 in sodium acetate buffer (0.1 M, pH 4) were prepared: 150, 100, 75, 50 and 25 µM. The freshly prepared {Al$^{18}$F}$^{2+}$ solution was added to 1 mL of the H$_3$L3 stock solutions. With this protocol we obtained H$_3$L3/AlCl$_3$ ratios ranging from 652 to 0.54. The vials were heated at 40° C. for 12 min and the RCY's were determined by iTLC-SG. The RCY's as shown by iTLC-SG are represented in FIG. 7. The optimal H$_3$L3/AlCl$_3$ ratio was in the range of 3.26 to 65.

Example 19: Effect of volume

Na$^{18}$F solution (50 µl) was added to 22.5 µl of 2 mM aluminum chloride (AlCl$_3$) in sodium acetate buffer (0.1 M, pH 4). The solution was incubated at RT for 10 min to form {Al$^{18}$F}$^{2+}$. Different stock solutions of H$_3$L3 in sodium acetate buffer (0.1 M, pH 4) were prepared: 900, 750, 600, 300 and 150 µM. Respectively 165, 200, 250, 500 and 1000 µl of the H$_3$L3 stock solutions were added to the freshly prepared {Al$^{18}$F}$^{2+}$ solution. With this protocol we obtained reaction volumes ranging from 238 µl to 1073 µl without changing the concentration of the ligand. The vials were heated at 40° C. for 12 min and the RCY's were determined by iTLC-SG. There was no significant effect of volume in the range of 238 µl to 573 µl (RCY>90%). When the volume was 1073 µl the RCY decreased to 82%.

Example 20: Effect of Na$^{19}$F Concentration

Na$^{18}$F solution (50 µl) and 5, 10, 20, 40 or 80 µl of Na$^{19}$F solution (1 mM) were added to 22.5 µl of 2 mM aluminum chloride (AlCl$_3$) in sodium acetate buffer (0.1 M, pH 4). Extra buffer was added to have in each vial the same reaction volume. The solutions were incubated at RT for 10 min to form {Al$^{18}$F}$^{2+}$. A solution of H$_3$L3 (1 mL, 150 µM) in sodium acetate buffer (0.1 M, pH 4) was added to the vials which contained the freshly prepared {Al$^{18/19}$F}$^{2+}$ solutions. The vials were heated at 40° C. for 12 min and the RCY's were determined by iTLC-SG. The results are shown in Table 1. As expected the RCY decreases if extra Na$^{19}$F is added. This experiment shows that not only the H$_3$L3/AlCl$_3$ ratio is important but also the Na$^{18/19}$F/AlCl$_3$ ratio.

TABLE 1

Effect of adding Na$^{19}$F on the complexation yield of H$_4$L3 (labeling reaction for 12 min at 40° C.).

| $^{19}$F added (mmol) | RCY % (determined by iTLC) |
|---|---|
| 0 | 80 |
| 5 | 80 |

TABLE 1-continued

Effect of adding Na$^{19}$F on the complexation yield
of H$_3$L3 (labeling reaction for 12 min at 40° C.).

| $^{19}$F added (mmol) | RCY % (determined by iTLC) |
|---|---|
| 10 | 77 |
| 20 | 68 |
| 40 | 65 |
| 80 | 47 |

Example 21: Effect of Organic Solvents and Additives

Na$^{18}$F solution (50 µl) was added to 22.5 µl of 2 mM aluminum chloride (AlCl$_3$) in sodium acetate buffer (0.1 M, pH 4). The solution was incubated at RT for 10 min to form {Al$^{18}$F}$^{2+}$. Different stock solutions of H$_3$L3 (1 mL, 150 µM) in sodium acetate buffer (0.1 M, pH 4) were prepared containing different percentages of acetonitrile or ethanol, ranging from 0% to 80%. Each solution was added to a vial which contained the freshly prepared {Al$^{18}$F}$^{2+}$ solution. The vials were heated at 40° C. for 12 min and the radiochemical yields were determined by iTLC-SG. We observed for both organic solvents an increase in RCY. The RCY's increased to 95% when we used a percentage of 20% of organic solvent. Acetonitrile and ethanol had a similar effect on the RCY.

Example 22: Effect of Incubation Time of the {Al$^{18}$F}$^{2+}$ Solution

Na$^{18}$F solution (50 µl) was added to 22.5 µl of 2 mM aluminum chloride (AlCl$_3$) in sodium acetate buffer (0.1 M, pH 4). Without incubation, the solution was directly added to 1 mL of the H$_3$L3 solution (150 µM) in sodium acetate buffer (0.1 M, pH 4) at RT. The yields were comparable (RCY's>75%, N=3) to those obtained by the standard protocol described in Example 15 where the solution of Na$^{18}$F and AlCl$_3$ in sodium acetate buffer (0.1 M, pH 4) was incubated at RT for 10 min to form {Al$^{18}$F}$^{2+}$.

Example 23: $^{18/19}$F Labeling of H$_3$L3 with Other Metals

Na$^{19}$F (42 mg, 1 mmol) was added to an aqueous solution of GaCl$_3$ (1 M, 1 mL). The pH was adjusted to 4 using an aqueous solution of sodium hydroxide (0.1 M) and the solution was stirred for 10 min. Then, an aqueous solution of the corresponding ligand (1 M, 1 mL) was slowly added and the mixture was heated at 80° C. for 1 h. The reaction was monitored by LC-MS. Ga$^{19}$F-L1, HRMS (ESI): Calcd. for C$_{20}$H$_{21}$FGaN$_2$O$_5$[M]$^-$ 457.0684; found 457.0691 and GaOH-L1, HRMS (ESI): Calcd. for C$_{20}$H$_{22}$GaN$_2$O$_6$[M]$^-$ 455.0728; found 455.0706 Na$^{18}$F solution (50 µl) was added to 22.5 µl of 2 mM gallium chloride (GaCl$_3$) in sodium acetate buffer (0.1 M, pH 4). The solution was incubated at RT for 10 min to form {Ga$^{18}$F}$^{2+}$. A solution of H$_3$L3 (1 mL, 150 µM) in sodium acetate buffer (0.1 M, pH 4) was added to a vial which contained a freshly prepared {Ga$^{18}$F}$^{2+}$ solution. The vials were heated at different temperatures for 12 min and the radiochemical yields were determined by iTLC-SG. H$_3$L3 was labeled with {Ga$^{18}$F}$^2$ in a non-optimized yield of 41% (30 min at room temperature, pH 4). Radio-HPLC-HRMS confirmed the presence of a gallium hydroxide complex (ESI-MS (m/z): found, 455.0693 [M]$^-$ calculated for C$_{20}$H$_{22}$GaN$_2$O$_6$ 455.0728) and a radioactive signal was observed with the same retention time as that of the cold Ga$^{19}$F-L3 complex. This confirms the presence of the Ga$^{18}$F-L3 complex.

Example 24: Labeling by Addition of 18F to a Ligand Pre-Incubated with Aluminum Aluminum chloride solution (22.5 µl, 2 mM) was added to 1 mL of H$_3$L3 solution (150 µM) in sodium acetate buffer (0.1 M, pH 4). The solution was incubated at RT for 10 min to form the AlOH-L3 complex. Then, Na$^{18}$F (50 µl) was added to the solution. The vials were heated at 40° C. for 12 min and the RCY's were determined by iTLC-SG. The yields were comparable (RCY>75%, N=4) to those obtained by addition of an Al$^{18}$F complex to the ligands. Thus, $^{18}$F labeling by addition of [$^{18}$F]fluoride to the ligand with aluminum already bound to the chelating moiety is a feasible alternative approach to the standard labeling protocol described in Example 15.

Example 25: Stability Tests of Al$^{18}$F-L3 in Different Buffers Ranging from pH 2 to 8

Al$^{18}$F-L3 was produced and purified as described in Example 15 by heating the mixture at 40° C. for 12 min. 200 µl of the purified Al$^{18}$F-L3 solution was added to 1 mL of sodium phosphate buffer (0.1 M, pH 2), sodium phosphate buffer (0.1 M, pH 3), sodium acetate buffer (0.1 M, pH 4), sodium acetate buffer (0.1 M, pH 5), sodium acetate buffer (0.1 M, pH 6), PBS buffer (0.1 M, pH 7) or Tris-HCl buffer (0.1 M, pH 8). These mixtures were incubated at room temperature and analyzed by iTLC-SG at 30 and 60 min after the start of the incubation. The results of the stability experiment are shown in FIG. 8 where the RCP is displayed as a function of time for the different buffers. The Al$^{18}$F-L3 complex is not stable at pH 2, pH 3 and pH 4. After 60 min the RCP has dropped respectively to 58%, 68% and 75%. In contrast the Al$^{18}$F-L3 complex is stable for at least 60 min in the pH range from 5 to 8. Consequently, an appropriate buffer should be selected for HPLC analysis of the [Al$^{18}$F]-complexes.

Example 26: Stability Tests of Al$^{18}$F-L1, Al$^{18}$F-L2, Al$^{18}$F-L3, Al$^{18}$F-L4, Al$^{18}$F-L5, Al$^{18}$F-L7 and Al$^{18}$F-NODA-benzyl in PBS (0.1 M, pH 7) and Rat Serum Al$^{18}$F-complexes were produced and purified as described in Example 15 by heating the mixtures at 40° C. for 12 min (Al$^{18}$F-L1, Al$^{18}$F-L2, Al$^{18}$F-L3, Al$^{18}$F-L4, Al$^{18}$F-L5 and Al$^{18}$F-L7) or at 110° C. for 12 min (Al$^{18}$F-NODA-benzyl). 400 µl of each purified [Al$^{18}$F]-complex solution was added to 1 mL of PBS and/or 1 mL of rat serum. These mixtures were incubated at 37° C. and analysed by iTLC-SG at 10, 30, 60, 120, 180 and 240 min after the start of the incubation. Serum samples were denatured by addition of 50 µl of the serum solution to 50 µl of acetonitrile. The mixture was stirred and centrifuged (1300 g, 3 min). Finally the supernatant was analysed using iTLC-SG.

Stability Tests in PBS

The stability of Al$^{18}$F-L1, Al$^{18}$F-L2, Al$^{18}$F-L3, Al$^{18}$F-L4, Al$^{18}$F-L5, Al$^{18}$F-L7 and Al$^{18}$F-NODA-benzyl in PBS (0.1M, pH7) at 37° C. is shown in FIG. 9 where the RCP is displayed as a function of time. Al$^{18}$F-L3, Al$^{18}$F-L4, and Al$^{18}$F-L5 exhibited stability in PBS comparable to that of Al$^{18}$F-NODA-benzyl up to 60 minutes. After that time the RCP's starts to decrease slowly to 80%, 85% and 78% respectively at 120 minutes. The RCP's after 240 min were 70%, 74% and 65% respectively. The RCP's of Al$^{18}$F-NODA-benzyl after 60 min, 120 min and 240 min were 99%, 98% and 88% respectively. The complexes Al$^{18}$F-L1, Al$^{18}$F-L2 and Al$^{18}$F-L7 do not seem to be stable, as substantial degradation occurs between 10 and 30 min. Only 31% of A$^{18}$F-L2 was still intact after 120 min.

Stability Tests in Rat Serum

The stability of Al$^{18}$F-L1, Al$^{18}$F-L2, Al$^{18}$F-L3, Al$^{18}$F-L4, Al$^{18}$F-L5, Al$^{18}$F-L7 and Al$^{18}$F-NODA-benzyl in rat serum at 37° C. is shown in FIG. 10 where the RCP is displayed as a function of time. Al$^{18}$F-L3, Al$^{18}$F-L4 and Al$^{18}$F-L5 exhibited good stability in rat serum, comparable to the stability observed for Al$^{18}$F-NODA-benzyl. The RCP's of Al$^{18}$F-L3, Al$^{18}$F-L4, and Al$^{18}$F-L5 after 120 min were higher than 80%. The RCP's after 240 min were 66%, 41% and 39% respectively. The RCP's of Al$^{18}$F-NODA-benzyl after 60 min, 120 min and 240 min were 99%, 97% and 87% respectively. On the other hand, Al$^{18}$F-L1 and Al$^{18}$F-L2 are unstable in serum and consequently their RCP's dropped to 0% in 120 minutes. The degradation of Al$^{18}$F-L1 and Al$^{18}$F-L2 occurred faster than in PBS.

Example 27: Biodistribution Studies

General

Quantification of radioactivity during biodistribution studies was performed using an automated gamma counter equipped with a 3-inch NaI(TI) well crystal coupled to a multichannel analyzer, mounted in a sample changer (Perkin Elmer 1480 Wizard 3q). Counts were corrected for background radiation, physical decay and counter dead time.

Animals were housed in individually vented cages in a thermoregulated (~22° C.), humidity-controlled facility under a 12 h-12 h light-dark cycle, with access to food and water ad libitum. All animal experiments were conducted according to the Belgian code of practice for the care and the use of animals, after approval from the university ethics committee for animals.

Biodistribution of [Al$^{18}$F]-L3 and {Al$^{18}$F}$^{2+}$

The biodistribution of the [Al$^{18}$F]-L3 complex and {Al$^{18}$F}$^{2+}$ was determined in healthy male Naval Medical Research Institute (NMRI) mice (body weight: 30-40 g) at 10 and 60 min post injection (p.i.) (n=4/time point). Mice were injected with the [Al$^{18}$F]-L3 complex (about 1 MBq) or {Al$^{18}$F}$^{2+}$ (5.55 MBq) via a tail vein under anesthesia (2.5% isoflurane in O$_2$ at 1 L/min flow rate) and sacrificed by decapitation at above specified time points. Blood and major organs were collected in tared tubes and weighed. The radioactivity in blood, organs and other body parts was counted using an automated γ-counter. For the calculation of total radioactivity in blood, bone and muscle, masses were assumed to be, respectively, 7, 12 and 40% of the total body mass.[20, 21]

Results

This biodistribution study was carried out to further assess the in vivo stability and evaluate the distribution profile of the Al$^{18}$F-L3 complex in comparison with that of {Al$^{18}$F}$^{2+}$. The results of the biodistribution of Al$^{18}$F-L3 and {Al$^{18}$F}$^{2+}$ injected mice are shown in FIG. 11. The graph shows the uptake of {Al$^{18}$F}$^{2+}$ and Al$^{18}$F-L3, presented as % ID, in different organs at 10 min and 60 min p.i. of the tracer.

As expected, there was high bone uptake for {Al$^{18}$F}$^{2+}$, 60% at 10 min p.i. and 83% at 60 min p.i. We also observed {Al$^{18}$F}$^{2+}$ excretion by the kidneys. In comparison, the biodistribution results of Al$^{18}$F-L3 showed 1.1% of ID at 10 min and 0.3% after 60 min in blood. Bone showed an uptake of 1.6% after 10 min and 2.5% 60 min after injection of Al$^{18}$F-L3 (Table 2).

TABLE 2

| | Biodistribution of Al$^{18}$F-L3 and {Al$^{18}$F}$^{2+}$ in mice at 10 minutes (N = 4) and 60 minutes (N = 4) p.i. | | | | | | | |
|---|---|---|---|---|---|---|---|---|
| | Al$^{18}$F-L3 | | | | {Al$^{18}$F}$^{2+}$ | | | |
| | 10 min p.i | SD | 60 min p.i | SD | 10 min p.i. | SD | 60 min p.i. | SD |
| blood | 1.1 | 0.30 | 0.3 | 0.03 | 5.0 | 0.52 | 0.6 | 0.13 |
| bone | 1.6 | 0.28 | 2.5 | 0.64 | 60.0 | 11.94 | 83.3 | 10.65 |
| kidneys | 2.2 | 0.30 | 1.0 | 1.17 | 2.2 | 0.25 | 0.5 | 0.32 |
| Urinary bladder | 13.2 | 4.41 | 17.8 | 5.40 | 20.7 | 2.28 | 30.6 | 11.53 |
| liver | 47.83 | 5.14 | 13.53 | 3.70 | 3.71 | 0.43 | 0.55 | 0.10 |
| intestines | 25.17 | 3.69 | 59.48 | 4.94 | 4.22 | 0.74 | 1.91 | 0.29 |

Particular and preferred aspects of the invention are set out in the accompanying independent and dependent claims. Features from the dependent claims may be combined with features of the independent claims and with features of other dependent claims as appropriate and not merely as explicitly set out in the claims.

Thus, the claims following the detailed description are hereby expressly incorporated into this detailed description, with each claim standing on its own as a separate embodiment of this invention.

Example 28: Ligand H$_3$L24 and H$_3$L25

Synthesis of Ligand H$_3$L24 and H$_3$L25 (FIG. 2 and Scheme 14)

Step 1: Synthesis of Compound 29 (methyl 2-(benzyl(2-((2-hydroxybenzyl)(2-methoxy-2-oxoethyl)amino)ethyl)amino)acetate)

To a solution of 4 (200 mg; 0.61 mmol) in tetrahydrofuran (5 mL) were successively added potassium carbonate (336 mg; 2.43 mmol; 4 eq.) and methyl bromoacetate (253 µL; 2.67 mmol; 4.4 eq.), at 0° C. The mixture was stirred at RT overnight. After filtration, the solvent was evaporated under reduced pressure. The obtained residue was purified by column chromatography (silica, n-heptane/ethyl acetate 75/25→60/40 v/v) to give 29 (58 mg; 0.15 mmol) as a colorless oil. Yield: 25% (formation of cyclic compounds with MS=297.1686); Rf (silica, n-heptane/ethyl acetate 5/5) 0.56; Rf (silica, n-heptane/ethyl acetate 75/25) 0.29; HRMS (ESI): Calcd. for C$_{22}$H$_{28}$N$_2$O$_5$ [M+H$^+$] 401.2071; found 401.2091; $^1$H NMR (400 MHz, CDCl$_3$) 2.78 (m, 2H, CH$_2$-b or c), 2.85 (m, 2H, CH$_2$-b or c), 3.38 (s, 4H, CH$_2$-e, f), 3.66 (s, 3H, CH$_3$), 3.68 (s, 3H, CH$_3$), 3.79 (s, 2H, CH$_2$-a or d), 3.80 (s, 2H, CH$_2$-a or d), 6.76 (t, 1H, J=7.3 Hz, CH-4), 6.86 (d, 1H, J=8.0 Hz, CH-3), 6.94 (d, 1H, J=7.2 Hz, CH-6), 7.18 (t, 1H, J=7.6 Hz, CH-5), 7.23-7.31 (m, 5H, CH—Ar benzyle); $^{13}$C NMR (101 MHz, CDCl$_3$) 51.4 (2C, CH$_3$), 52.0 (C-b or c), 52.4 (C-b or c), 54.4 (C-e or f), 54.5 (C-e or f), 57.5 (C-a), 59.2 (C-d), 117.1 (C-4), 119.8 (C-6), 122.4 (C-2), 128.0 (C-4' or 3), 129.0 (2C, C-3', 5'), 129.8 (C-4' or 3), 129.9 (3C, C-2', 6', 5?), 138.9 (C-1'), 158.3 (C-1), 171.8 (C=O), 172.3 (C=O).

Step 2: Synthesis of Compound H₃L24 (2-((2-(benzyl(2-(hydroxyamino)-2-oxoethyl)amino)ethyl)(2-hydroxybenzyl)amino)acetic acid) and H₃L25 (2-(benzyl(2-((2-(hydroxyamino)-2-oxoethyl)(2-hydroxybenzyl)amino)ethyl)amino)-N-hydroxyacetamide)

To a solution of 29 (30 mg; 75 µmol) in methanol/tetrahydrofuran (1:1, 1000 µL) were successively added NaOH aq. (1N, 600 µL) and hydroxylamine 50% wt. in water (1000 µL) at 0° C. The mixture was stirred at 0° C. for 1 h, and then at RT for 2 h. The reaction was then quenched by adding HCl aq. (37%) until pH 6-7, and the solvent was concentrated under reduced pressure. The crude mixture was then diluted with water (2 mL) and loaded on a C18+ cartridge (conditioned with EtOH (1 mL) then water (20 mL)). The cartridge was washed with water (5 mL) then the product was eluted with EtOH (5×1 mL). Fractions 1-3 were evaporated under reduced pressure to yield to a mixture of H₃L24 and H₃L25 (19 mg total, ~50:50 according to UV chromatogram). HRMS (ESI) H₃L24: Calcd. for $C_{20}H_{25}N_3O_5[M+H^+]$ 388.1867; found 388.1879; and HRMS (ESI) H₃L25: Calcd. for $C_{20}H_{26}N_4O_5$ [M+H⁺] 403.1976; found 403.1994; ¹H NMR (400 MHz, MeOD-d4), H₃L24 and H₃L25.2.62-2.68 (m, 8H), 3.06-3.21 (m, 8H), 3.35-3.67 (m, 8H), 6.78-7.39 (m, 18H).

Production of [Al¹⁸F]-H₃L24/[Al¹⁸F]-H₃L25

A solution of the mixture of H₃L24 and H₃L25 (1 mL, 150 M, 50:50 according to UV chromatogram) in sodium acetate buffer (0.1 M, pH 4) was added to a vial which contained a freshly prepared {Al¹⁸F}²⁺ solution. The vials were heated at different temperatures for 12 min and the radiochemical yields were determined by iTLC-SG.

The radiochemical yields (RCY's) derived from iTLC-SG analyses at different temperatures are represented in table 3.

TABLE 3 radiochemical yields of the {Al¹⁸F}-complexation with a mixture of H₃L24 and H₃L25 (~50:50 according to UV chromatogram) at different temperatures.

| Temperature | RCY (%) |
|---|---|
| RT | 10 |
| 40° C. | 10 |
| 60° C. | 15 |
| 80° C. | 47 |
| 110° C. | 34 |

Example 29: Ligand H₃L26

Synthesis of Ligand H₃L26 (FIG. 2 and Scheme 1S)

Step 1: Synthesis of Compound (±)30 ((+)-trans-1-N-benzylcyclohexane-1,2-diamine)

To a solution of (+)-trans-1,2-Diaminocyclohexane (4.2 g, 36 mmol) in methanol (MeOH) (10 mL), benzaldehyde (400 mg, 3.6 mmol) was added. The mixture was stirred for 2 h at 65° C. The mixture was then cooled on an ice bath to 0° C. Next, sodium borohydride (136 mg, 3.6 mmol) was gradually added to the mixture, during which time the solution was allowed to reach RT. The solvent was evaporated and an aqueous saturated solution of sodium carbonate (10 mL) was added. The product was extracted three times using equal volumes of dichloromethane (DCM). The combined organic layers were then dried with magnesium sulfate and evaporated under reduced pressure affording (±)-30 quantitative (735 mg). HRMS (ESI): Calcd. for $C_{13}H_{18}N_2$ [M+H⁺] 203.1699; found 203.1712. ¹H NMR (400 MHz, CDCl₃) δ 7.37-7.27 (m, 4H), 7.27-7.20 (m, 1H), 3.94 (d, J=13.0 Hz, 1H), 3.69 (d, J=13.0 Hz, 1H), 2.44-2.35 (m, 1H), 2.20-2.06 (m, 2H), 1.92-1.83 (m, 1H), 1.77-1.65 (m, 2H), 1.32-0.99 (m, 4H). ¹³C NMR (101 MHz, CDCl₃) δ 141.2, 128.4, 128.2, 126.9, 63.4, 61.0, 55.5, 51.2, 36.2, 31.5, 25.4.

Step 2: Synthesis of Compound (+)31 tert-butyl 2-{benzyl[(±)-trans-2-{bis[2-(tert-butoxy)-2-oxo-ethyl]amino}cyclohexyl]amino}acetate To a solution of compound (±)-30 (735 mg, 3.6 mmol) in DCM (5 mL) N,N-Diisopropylethylamine (DIPEA) (1.9 ml, 10.8 mmol) and tert-butyl bromoacetate (2.1 g, 10.8 mmol) were successively and slowly added. The mixture was then stirred at RT for 12 h. The solution was filtered and the solvent removed under vacuum. A saturated solution of NaHCO₃ (50 mL) was added and the product was extracted three times with DCM (20 mL). The obtained oil was purified using flash chromatography on silica gel (ethyl acetate/heptane, 1:3) affording pure product (±)-31 (1.42 g, 72%).

HRMS (ESI): Calcd. for $C_{31}H_{50}N_2O_6[M+H^+]$ 547.3742; found 547.3651. ¹H NMR (400 MHz, CDCl₃) δ 7.43 (d, J=7.9 Hz, 2H), 7.31-7.27 (m, 1H), 7.24-7.17 (m, 2H), 4.01 (d, J=13.4 Hz, 1H), 3.69 (d, J=13.4 Hz, 1H), 3.47 (d, J=16.7 Hz, 1H), 3.42 (d, J=16.7 Hz, 1H), 3.39 (d, J=16.7 Hz, 1H), 3.27 (d, J=16.7 Hz, 1H), 2.71 (d, J=10.8 Hz, 1H), 2.56 (td, J=10.6, 3.5 Hz, 1H), 2.05 (d, J=10.9 Hz, 1H), 1.66 (s, 1H), 1.44 (s, 6H), 1.43 (s, 5H), 1.08 (t, J=10.0 Hz, 1H), 0.90-0.84 (m, 1H). ¹³C NMR (101 MHz, CDCl₃) δ 172.3, 171.8, 140.4, 129.4, 128.2, 126.9, 80.4, 80.3, 63.7, 61.2, 54.9, 53.4, 53.0, 29.7, 28.5, 28.3, 28.3, 26.1, 25.9.

Step 3: Synthesis of Compound H₃L26 2-{[(±)-trans-2-[benzyl(carboxymethyl)amino]cyclohexyl](carboxymethyl)amino}acetic Acid Compound (±)-31 (100 mg, 0.22 mmol) was stirred in trifluoroacetic acid (TFA) (2 mL) at RT for 12 h. The deprotection was monitored over time using LC-MS until full conversion of compound (±)-31 was established. Afterwards, the solvent was evaporated under reduced pressure affording pure H₃L26 (78 mg, 90%).

HRMS (ESI): Calcd. for $C_{19}H_{26}N_2O_6$ [M+H⁺] 379.1758; found 379.1762. ¹H NMR (400 MHz, D₂O) δ 7.64-7.31 (m, 5H), 4.57 (br.d, J=12.5 Hz, 1H), 4.23 (br.d, J=13.0 Hz, 2H), 3.94 (d, J=16.8 Hz, 1H), 3.52-3.38 (m, 1H), 3.38-3.16 (m, 2H), 3.00-2.80 (m, 1H), 2.51-2.38 (m, 1H), 2.33 (br.d, J=9.8 Hz, 1H), 1.97 (br.d, J=8.9 Hz, 1H), 1.87 (br.d, J=12.5 Hz, 1H), 1.75 (br.d, J=11.0 Hz, 1H), 1.60-1.45 (m, 1H), 1.38-1.06 (m, 4H). ¹³C NMR (101 MHz, D₂O) δ 174.7, 174.5, 131.6, 131.2, 130.3, 130.2, 66.7, 62.2, 59.9, 58.0, 54.0, 51.1, 48.5, 17.5, 14.8.

Identification of Reference Compound, Al¹⁹F-L26 (FIG. 12)

Na¹⁹F (0.69 mg, 0.017 mmol) was added to an aqueous solution of AlCl₃ (0.83 M, 20 µL). The pH was adjusted to 4.5 using an aqueous solution of sodium hydroxide (0.1 M) and the mixture was stirred for 10 min. Then, an aqueous solution of H₃L26 (0.017 mmol, 0.5 mL) was slowly added and the mixture was stirred at RT for 1 h.

HRMS (ESI): Calcd. for $C_{19}H_{23}AlFN_2O_6[M]^-$ 421.1350; found 421.1342. ¹H NMR (400 MHz, D₂O) δ 7.57-7.35 (m, 5H), 4.28-4.15 (m, 2H), 3.95 (d, J=12.8 Hz, 1H), 3.81 (d, J=16.1 Hz, 1H), 3.69 (d, J=16.6 Hz, 1H), 3.59 (d, J=16.4 Hz, 1H), 3.46 (d, J=16.5 Hz, 1H), 3.36 (d, J=19.1 Hz, 1H), 3.10 (br.t, J=11.0 Hz, 1H), 2.78 (br.t, J=10.2 Hz, 1H), 1.93 (br.d, J=13.4 Hz, 1H), 1.77-1.69 (m, 1H), 1.66-1.56 (m, 1H), 1.55-1.45 (m, 1H), 1.19-1.09 (m, 2H), 1.05-0.94 (m, 1H), 0.94-0.83 (m, 1H). $^{19}F$ NMR (376 MHz, $D_2O$) δ−171.43.

Production of [$Al^{18}F$]-$H_3L26$

Production of Aqueous Solution of [$^{18}F$]Fluoride and $\{Al^{18}F\}^{2+}$

After cyclotron production, [$^{18}F$]$F^-$ was separated from [$^{18}O$]$H_2O$ by trapping on a SepPak™ Light Accel plus QMA anion exchange cartridge ($Cl^-$ form; Waters, Milford, USA). The [$^{18}F$]$F^-$ (148-333 MBq) was eluted from the cartridge with an aqueous solution of sodium chloride 0.9% (0.4 mL). This aqueous solution of [$^{18}F$]fluoride (50 μl) was added to 22.5 μl of 2 mM aluminum chloride ($AlCl_3$) in sodium acetate buffer (0.1 M, pH 4). The solution was incubated at RT for 10 min to form $\{Al^{18}F\}^{2+}$.

Production and Purification of [$Al^{18}F$]-$H_3L26$

A solution of $H_3L26$ (1 mL, 150 μM) in sodium acetate buffer (0.1 M, pH 4) was added to a vial which contained a freshly prepared $\{Al^{18}F\}^{2+}$ solution. The vials were heated at different temperatures for 12 min and the radiochemical yields were determined by iTLC-SG.

The resulting mixtures were purified with a Sep-Pak® Plus Alumina-N-Cartridge (Waters, Milford, USA). The cartridge was pre-rinsed with an aqueous solution of sodium chloride 0.9% (5 mL) and the crude reaction mixture was loaded on the column. The cartridge was then rinsed with an aqueous solution of sodium chloride 0.9% (3 mL). The eluate was collected and each of the purified ligand-[$Al^{18}F$]$^{2+}$ complex solutions was analysed using iTLC-SG and radio-HPLC-HRMS.

$H_3L26$ was labeled with $\{Al^{18}F\}^{2+}$ in a non-optimized yield of 86% (12 min, room temperature, pH 4.5; N=3), determined with iTLC-SG. Radio-HPLC-HRMS confirmed the presence of the aluminum fluoride complex (ESI-MS (m/z): found, 421.1346 [M]$^-$ calculated for $C_{19}H_{23}AlFN_2O_6$ 421.1350), and the aluminum hydroxide complex (similar complex in which the fluoride ion is replaced by an hydroxide ion) (ESI-MS (m/z): found, 419.1389 [M]$^-$ calculated for $C_{19}H_{23}AlN_2O_7$ 419.1393.

The radiochemical yields (RCY's) derived from iTLC-SG analyses at different temperatures are represented in table 4. $H_3L26$ showed efficient chelation of $\{Al^{18}F\}^{2+}$ at all tested temperatures with RCY's higher than 80%. The radiochemical purity after purification was >98%. FIG. 13 shows the radio-HPLC-HRMS of $Al^{18}F$-L26 after purification.

TABLE 4 radiochemical yields of the $\{Al^{18}F\}$-complexation with $H_3L26$ at different temperatures. (N = 3)

| Temperature | RCY (%) | SD |
|---|---|---|
| RT | 86 | 3.5 |
| 40° C. | 93 | 3.8 |
| 60° C. | 92 | 1.7 |
| 80° C. | 85 | 0.6 |
| 110° C. | 80 | 2.5 |

Effect of pH

A solution (1 mL, 150 μM) of $H_3L26$ was prepared in sodium acetate buffer (0.1 M, pH 3, 3.5, 4, 4.5, 5, 5.5), 2-(N-morpholino)ethanesulfonic acid (MES) buffer (0.1M; pH 6, 6.5; 7) or Tris(hydroxymethyl)aminomethane hydrochloride (Tris-HCl) buffer (0.1M; pH 7.5, 8) and was added to different vials which contained 50 μL (3.7 MBq) of a freshly prepared $\{Al^{18}F\}^{2+}$ solution. The mixtures were incubated at room temperature and radiochemical yields were determined by by iTLC-SG at 12 min after the start of the incubation (N=3).

The radiochemical yields at different pH as shown by iTLC-SG are represented in FIG. 14. The optimal pH range for labeling $H_3L26$ was between 4 and 5, but even at pH 5.5 high RCY's were observed. When the labeling was performed under pH 4, the RCY's were decreasing rapidly.

Stability Tests of $Al^{18}F$-L26 in PBS (0.1 M, pH 7.4) and Rat Serum

100 μl of [$Al^{18}F$]-L26 was added to 400 μl of PBS or 400 μl of rat serum. These mixtures were incubated at 37° C. and analysed by iTLC-SG at 10, 30, 60, 120, 180 and 240 min after the start of the incubation (N=3). Serum samples were denatured by addition of 50 μl of the serum solution to 50 μl of acetonitrile. The mixture was stirred and centrifuged (1300 g, 3 min). Finally the supernatant was analysed using iTLC-SG.

The results of the stability experiment of $Al^{18}F$-L26 in PBS (0.1M, pH7) and rat serum at 37° C. are shown in table 4. These data indicate excellent stability of the $Al^{18}F$-L26 complex in both PBS and rat serum at 37° C.

TABLE 4 stability experiment of $Al^{18}F$-L26 in PBS (0.1M, pH 7.4) and rat serum at 37° C. (N = 3)

| | PBS % intact tracer | SD | Rat Serum % intact tracer | SD |
|---|---|---|---|---|
| 10 min | 99.1 | 0.1 | 97.2 | 5.0 |
| 30 min | 98.0 | 0.1 | 99.0 | 0.9 |
| 1 h | 97.8 | 2.3 | 97.3 | 0.7 |
| 2 h | 91.0 | 4.2 | 86.7 | 7.0 |
| 3 h | 95.3 | 2.5 | 91.6 | 0.6 |
| 4 h | 87.3 | 0.6 | 91.2 | 2.4 |

Stability Tests of $Al^{18}F$-L26 in Different Buffers Ranging from pH 2 to 8

200 μl of the purified $Al^{18}F$-L26 solution was added to 1 mL of sodium phosphate buffer (0.1 M, pH 2), sodium phosphate buffer (0.1 M, pH 3), sodium acetate buffer (0.1 M, pH 4), sodium acetate buffer (0.1 M, pH 5), sodium acetate buffer (0.1 M, pH 6), PBS buffer (0.1 M, pH 7) or Tris-HCl buffer (0.1 M, pH 8). These mixtures were incubated at room temperature and analyzed by iTLC-SG at 30 and 60 min after the start of the incubation.

The results of the stability experiment are shown in FIG. 15 where the percentage intact tracer is displayed as a function of time for the different buffers. The $Al^{18}F$-L26 complex is stable for at least 60 min in the pH range from 2 to 8. Consequently, an acidic buffer can be selected for HPLC analysis of the $Al^{18}F$-L26-complex.

Biodistribution Study [$Al^{18}F$]-L26

General

Quantification of radioactivity during biodistribution studies was performed using an automated gamma counter equipped with a 3-inch Nai(Tl) well crystal coupled to a multichannel analyzer, mounted in a sample changer (Perkin Elmer 1480 Wizard 3q). Counts were corrected for background radiation, physical decay and counter dead time.

Animals were housed in individually vented cages in a thermoregulated (~22° C.), humidity-controlled facility under a 12 h-12 h light-dark cycle, with access to food and water ad libitum. All animal experiments were conducted according to the Belgian code of practice for the care and the use of animals, after approval from the university ethics committee for animals.

Biodistribution of [Al$^{18}$F]-L26 and {Al$^{18}$F}$^{2+}$

The biodistribution of the [Al$^{18}$F]-L26 complex and {Al$^{18}$F}$^{2+}$ was determined in healthy male Naval Medical Research Institute (NMRI) mice (body weight: 30-40 g) at 10 and 60 min post injection (p.i.) (n=3/time point for 10 min p.i. and n=4/time point for 60 min p.i.). Mice were injected with the [Al$^{18}$F]-L26 complex (about 1 MBq) or {Al$^{18}$F}$^{2+}$ (5.55 MBq) via a tail vein under anesthesia (2.5% isoflurane in O$_2$ at 1 L/min flow rate) and sacrificed by decapitation at above specified time points. Blood and major organs were collected in tared tubes and weighed. The radioactivity in blood, organs and other body parts was counted using an automated γ-counter. For the calculation of total radioactivity in blood, bone and muscle, masses were assumed to be, respectively, 7, 12 and 40% of the total body mass.[20,21]

Results

This biodistribution study was carried out to further assess the in vivo stability and evaluate the distribution profile of the Al$^{18}$F-L26 complex in comparison with that of {Al$^{18}$F}$^{2+}$. The results of the biodistribution of Al$^{18}$F-L26 and {Al$^{18}$F}$^{2+}$ injected mice are shown in FIG. 16. The graph shows the uptake of {Al$^{18}$F}$^{2+}$ and Al$^{18}$F-L26, presented as % ID, in different organs at 10 min and 60 min p.i. of the tracer.

As expected, there was high bone uptake for {Al$^{18}$F}$^{2+}$, 60% at 10 min p.i. and 83% at 60 min p.i. We also observed {A 18F}$^{2+}$ excretion by the kidneys. In comparison, the biodistribution results of Al$^{18}$F-L26 showed 2.0% of ID at 10 min and 0.1% after 60 min in blood. Bone showed an uptake of 1.6% after 10 min and 1.9% 60 min after injection of Al$^{18}$F-L26 (Table 5). The biodistribution of Al$^{18}$F-L26 showed high stability, since only very limited bone uptake-which would be an indication of release of fluorine-18 in the form of fluoride—was observed, whereas the major fraction of activity 60 min p.i. was observed in liver and intestines due to hepatobiliary clearance of the radiolabeled ligand.

TABLE 5

Biodistribution of Al$^{18}$F-L26 and {Al$^{18}$F}$^{2+}$ in mice at 10 minutes (N = 3) and 60 minutes (N = 4) p.i.

| | Al$^{18}$F-L26 | | | | {Al$^{18}$F}$^{2+}$ | | | |
|---|---|---|---|---|---|---|---|---|
| | 10 min p.i | SD | 60 min p.i | SD | 10 min p.i. | SD | 60 min p.i. | SD |
| blood | 1.9 | 0.92 | 0.1 | 0.02 | 5.0 | 0.52 | 0.6 | 0.13 |
| bone | 1.6 | 0.34 | 1.9 | 0.30 | 60.0 | 11.94 | 83.3 | 10.65 |
| kidneys | 4.6 | 0.66 | 0.2 | 0.06 | 2.2 | 0.25 | 0.5 | 0.32 |
| Urinary bladder | 14.3 | 2.74 | 21.5 | 6.25 | 20.7 | 2.28 | 30.6 | 11.53 |
| liver | 49.5 | 3.25 | 8.8 | 2.19 | 3.71 | 0.43 | 0.55 | 0.10 |
| intestines | 19.6 | 4.01 | 62.7 | 5.26 | 4.22 | 0.74 | 1.91 | 0.29 |

Example 30: Ligand H$_3$L27

Synthesis of Ligand H$_3$L27 (FIG. 2 and Scheme 16)

Step 1: Synthesis of Compound (±)32 tert-butyl 2-{[(+)-trans-2-{bis[2-(tert-butoxy)-2-oxoethyl]amino}cyclohexyl]amino}acetate To a solution of compound (±)-31 (180 mg, 0.33 mmol) in MeOH (5 mL), ammonium formate (104 mg, 1.6 mmol) and palladium on activated carbon 10% (Pd/C) (100 mg) was added in a sealed tube. The mixture was stirred for 2 h at 65° C. Afterwards, the mixture was filtered and evaporated under reduced pressure. Next, DCM (10 mL) was added, the solution was filtered and evaporated under reduced pressure affording pure compound (±)-32 (122 mg, 81%). HRMS (ESI): Calcd. for C$_{24}$H$_{44}$N$_2$O$_6$ [M+H$^+$] 457.3272; found 457.3284. $^1$H NMR (400 MHz, CDCl$_3$) δ 3.84 (d, J=17.0 Hz, 1H), 3.56 (d, J=18.2 Hz, 2H), 3.47-3.39 (m, 3H), 3.07-2.93 (m, 1H), 2.73-2.61 (m, 1H), 2.14-2.07 (m, 1H), 2.07-2.00 (m, 1H), 1.92-1.73 (m, 3H), 1.50 (s, 9H), 1.45 (s, 18H), 1.23 (ddd, J=46.7, 32.1, 17.6 Hz, 3H). $^{13}$C NMR (101 MHz, CDCl$_3$) δ 172.11, 165.61, 83.63, 81.70, 64.43, 59.09, 53.24, 45.18, 28.03, 27.92, 27.22, 26.88, 24.47, 24.08.

Step 2: Synthesis of Compound 33 2-[4-({[(±)-trans-2-{bis[2-(tert-butoxy)-2-oxoethyl]amino}cyclohexyl][2-(tert-butoxy)-2-oxoethyl]amino}methyl)phenyl]acetic Acid To a solution of compound (±)-32 (122 mg, 0.27 mmol) in DCM (5 mL), DIPEA (69 μL, 0.53 mmol) and 4-(Bromomethyl)phenylaceticacid (61 mg, 0.27 mmol) were successively and slowly added. The mixture was then stirred at RT for 12 h and the solution was evaporated under reduced pressure. Next, diethylether (5 mL) was added to the crude mixture and the solution was filtered. Afterwards, the solvent was removed under vacuum affording compound 33 (143 mg).

HRMS (ESI): Calcd. for C$_{33}$H$_{52}$N$_2$O$_8$ [M+H$^+$] 605.3718; found 605.3723.

Example 31: Radiosynthesis and Preclinical Evaluation of New Al$^{18}$F-Labeled Urea-Based PSMA Inhibitors for PET Imaging of Prostate Cancer Introduction Prostate-specific membrane antigen (PSMA) is overexpressed in a majority of primary and metastatic prostate cancer patients and can be considered as a promising target for specific prostate cancer imaging and therapy. The urea based PSMA inhibitor $^{68}$Ga-HBED-CC-PSMA[1] showed excellent pharmacokinetics as well as stability in vivo, leading to its clinical applications worldwide for the imaging of prostate cancer.

However, among the positron-emitting isotopes ($^{11}$C, $^{64}$Cu, $^{18}$F, $^{13}$N, $^{15}$O, $^{68}$Ga, $^{89}$Zr, $^{124}$I), fluorine-18 has several advantages like, suitable decay properties (t$_{1/2}$=109.8 min, ~97% β$^+$-emission, β$^+$ max 635 keV), low β$^+$-trajectory in water (<2 mm), small atomic size and moreover, it is readily produced in a cyclotron in relatively large amounts. A promising approach for $^{18}$F-labeling of biomolecules consists of chelation of [Al$^{18}$F]$^{2+}$ by biomolecules-conjugated to macrocyclic chelators in aqueous environment. This methodology is promising in view of its potential to evolve to a simple "kit" type preparation and its applicability for a wide array of imaging probes for PET.

Three new Al$^{18}$F-labeled urea-based PSMA inhibitors were developed and their biodistribution in mice was compared with that of $^{68}$Ga-HBEDD-CC-PSMA[1]. Autoradiography experiments were conducted on LNCaP PSMA positive tumor coupes and on human prostate tumor tissue.

Materials and Methods

The bifunctional chelators H$_3$L6, H$_3$L27 and NODA-MPAA[2] were conjugated to the established lysine-glutamate urea scaffold to form H₃L6-PSMA, H₃L27-PSMA, and NODA-MPAA-PSMA (FIG. 17).

[¹⁸F]fluoride was produced and trapped on a SepPak™ Light Accel plus QMA anion as described previously. The [¹⁸F]F⁻ was eluted from the cartridge with an aqueous solution of sodium chloride 0.9% (0.25 mL) and added to 5 µl of 20 mM (100 nmol) aluminum chloride (AlCl₃) in sodium acetate buffer (0.1 M, pH 4.5). The solution was incubated at RT for 5 min to form {Al¹⁸F}²⁺. A solution of H₃L6-PSMA, H₃L27-PSMA or NODA-MPAA-PSMA (115 µl, 2.58 mM) in sodium acetate buffer (0.1 M, pH 4.5) was added and the reactor was heated at 40° C., RT (20-25° C.) or 110° C. respectively for 12 min. After dilution with water (0.5 mL), the crude reaction mixture was purified with semi-preparative HPLC (XBridge C₁₈, 5 µm, 4.6 mm×150 mm, Waters) using the following method. Solvent A (ammonium acetate 0.05M pH 5.5) and solvent B (EtOH), flow rate 1 ml/min. The elution gradient was 100% A to 80% A and 0% B to 20% B over 0-25 min. UV detection of the eluate was performed at 254 nm. Identification of the [Al¹⁸F]-complexes was done by radio-LC-HRMS (Acquity UPLC BEH C₁₈, 1.7 µm, 2.1 mm×150 mm, Waters. 0.6 mL/min A: H₂O B: ACN, 0-2 min 5% B, 2 to 8 min 5% B to 95% B, 8-10 min 95% B, 10 to 12 min 95% B to 5% B).

The compounds ⁶⁸Ga-HBED-CC-PSMA, Al¹⁸F-L6-PSMA, Al¹⁸F-L27-PSMA or Al¹⁸F-NODA-MPAA-PSMA were injected via the tail vain (1-2 MBq) with or without coadministration of 2 mg/kg 2-PMPA. At 10 min or 60 min p.i. (N=4), the animals were sacrificed. Blood and major organs were collected in tarred tubes and weighed. The radioactivity was measured using an automated γ-counter and calculated as % ID and % ID/g.

Quantification of radioactivity during biodistribution studies was performed using an automated gamma counter equipped with a 3-inch NaI(Tl) well crystal coupled to a multichannel analyzer, mounted in a sample changer (Perkin Elmer 1480 Wizard 3q). Counts were corrected for background radiation, physical decay and counter dead time.

Animals were housed in individually vented cages in a thermoregulated (~22° C.), humidity-controlled facility under a 12 h-12 h light-dark cycle, with access to food and water ad libitum. All animal experiments were conducted according to the Belgian code of practice for the care and the use of animals, after approval from the university ethics committee for animals. Autoradiography was performed using phosphor storage screens (super-resolution screen, Perkin Elmer). Screens were read in a Cyclone Plus system (Perkin Elmer) and analysed using Optiquant software.

Results

Al¹⁸F-L6-PSMA, Al¹⁸F-L27-PSMA and Al¹⁸F-NODA-MPAA-PSMA were prepared in high radiochemical yields (>50%) and purity (>95%). All tracers were stable (>95%) in saline at room temperature for at least three hours. Identification of the [Al¹⁸F]-complexes was done by radio-LC-HRMS. The results of the biodistribution of ⁶⁸Ga-HBED-CC-PSMA, Al¹⁸F-L6-PSMA, Al¹⁸F-L27-PSMA and Al¹⁸F-NODA-MPAA-PSMA injected mice are shown in FIGS. 17, 18, 19 and 20. The graphs show the uptake, presented as % ID, in different organs at 10 min and 60 min p.i. of the tracer. The biodistribution of ⁶⁸Ga-HBED-CC-PSMA, Al¹⁸F-L6-PSMA, Al¹⁸F-L27-PSMA or Al¹⁸F-NODA-MPAA-PSMA showed high in vivo stability, since no significant bone uptake, which would be an indication of release of fluorine-18, was observed (0.39±0.09% ID/g, 0.74±0.07% ID/g, 0.80±0.22% ID/g and 0.13±0.02% ID/g). All tracers were cleared fast from plasma and PSMA negative tissue. The retention at 60 min p.i. in organs with reported high expression of PSMA such as kidney (269.90±47.23% ID/g, 121.27±10.82% ID/g, 83.06±16.41% ID/g and 15.68±6.27% ID/g) and spleen (2.72±0.42% ID/g, 4.38±0.55% ID/g, 1.32±0.35% ID/g and 0.23±0.07% ID/g) was nearly completely blocked when 2-PMPA was coinjected to block PSMA specific binding indicating PSMA specific retention. Autoradiography with all four tracers on human prostate tumor tissue and human prostate tissue showed specific affinity for the human PSMA receptor (FIG. 22).

Conclusions

Three new Al¹⁸F-labeled urea-based PSMA inhibitors were successfully produced with high radioactive yields and purity. The high spleen and kidney uptake (and retention) of ⁶⁸Ga-HBED-CC-PSMA and Al¹⁸F-L6-PSMA and to a lower extend of Al¹⁸F-L27-PSMA indicates high affinity for the PSMA receptor. Autoradiography with Al¹⁸F-L6-PSMA and Al¹⁸F-L27-PSMA on human prostate tumor tissue showed specific affinity for the human PSMA receptor. The first preclinical results of especially Al¹⁸F-L6-PSMA and Al¹⁸F-L27-PSMA look promising.

Example 31: Ligand H₃L28

Step 1: Synthesis of Compound (±)-34 di-tert-butyl 2,2'-(((1R,2R)-2-((2-(tert-butoxy)-2-oxoethyl)(4-(2-oxo-2-(2,3,5,6-tetrafluorophenoxy)ethyl)benzyl)amino)cyclohexyl)azanediyl)diacetate A solution of 33 (0.33 g, 0.55 mmol), tetrafluorophenol (TFP) (0.136 g, 0.82 mmol), and N,N-dicyclohexylcarbodiimide (DCC) (0.17 g, 0.82 mmol) in dioxane (5 mL) was stirred overnight. Dicyclohexylurea (DCU) was filtered off and the solvent removed in vacuo. The obtained oil was purified using flash chromatography on silica gel (ethyl acetate/heptane, 1:4) affording pure product (±)-34 (92 mg, 20%). HRMS (ESI): Calcd. for $C_{39}H_{52}F_4N_2O_8[M+H^+]$ 753.3660; found 753.3610. ¹H NMR (400 MHz, CDCl₃) δ 7.46 (d, J=7.9 Hz, 2H), 7.28 (d, J=8.0 Hz, 2H), 6.97 (tt, J=9.9, 7.0 Hz, 1H), 4.03 (d, J=13.7 Hz, 1H), 3.94 (s, J=15.2 Hz, 2H), 3.68 (d, J=13.5 Hz, 1H), 3.48 (d, J=16.8 Hz, 2H), 3.43 (d, J=17.0 Hz, 2H), 3.37 (d, J=16.7 Hz, 1H), 3.26 (d, J=16.8 Hz, 1H), 2.76-2.66 (m, 1H), 2.65-2.50 (m, 1H), 2.02 (br.s, 3H), 1.66 (br.s, 3H), 1.43 (s, 18H), 1.41 (s, 9H), 1.15-0.98 (m, 4H). ¹³C NMR (101 MHz, CDCl₃) δ 147.3 (td, J=11.9, 4.3 Hz), 144.9 (td, J=11.9, 4.3 Hz), 142.0 (ddd, J=15.2, 4.7, 2.0 Hz), 139.5 (ddd, J=15.4, 4.7, 2.1 Hz), 103.3 (t, J=22.8 Hz). ¹⁹F NMR (376 MHz, D₂O) δ−138.9−−139.2 (m), −152.6−−152.9 (m).

Step 2: Synthesis of Compound H₃L28 (2,2'-(((1R,2R)-2-((carboxymethyl)(4-(2-oxo-2-(2,3,5,6-tetrafluorophenoxy)ethyl)benzyl)amino)cyclohexyl)azanediyl)diacetic Acid)

Compound (±)-34 (50 mg, 0.07 mmol) was stirred in trifluoroacetic acid (TFA) (2 mL) at RT for 4 h. The deprotection was monitored over time using LC-MS until full conversion of compound (+)-34 was established. Afterwards, the solvent was evaporated under reduced pressure affording pure H₃L28 (45 mg, 83%). HRMS (ESI): Calcd. for $C_{27}H_{28}F_4N_2O_8[M+H^+]$ 585.1782; found 585.1802.

Example 32: $^{18}$F-Labeling of Nanobodies Via the Al$^{18}$F-Method (FIG. 23)

Introduction

The Al$^{18}$F labeling method is a relatively new approach that allows radiofluorination of biomolecules such as peptides and proteins in a one-step procedure and in aqueous medium. Conventional radiofluorination strategies involve carbon-fluor bond formation in anhydrous aprotic solvents. In contrast, the Al$^{18}$F-strategy involves the formation of aluminium monofluoride ($\{Al^{18}F\}^{2+}$) which is trapped by a suitable chelator-mostly bound to a biomolecule—in aqueous medium. The newly developed chelators for the Al$^{18}$F-method provides efficient chelation of $\{Al^{18}F\}^{2+}$ at moderate temperature (<40° C.). This could ultimately allow development of a kit-based, room temperature fluorine-18 radiolabeling method for heat sensitive biomolecules.

Nanobodies (VHH) are the antigen-binding fragments (13-15 kDa) derived from heavy-chain-only antibodies occurring naturally in Camelid species. Nanobodies bind their antigens very fast and specifically in vivo, whereas unbound nanobody is rapidly cleared from the blood by the kidneys. This results in high contrast positron emission tomography (PET) images as early as 1 hour after administration.

The objective of this project is to radiolabel nanobodies efficiently via the Al$^{18}$F-method. In the first step the nanobody will be conjugated to the bifunctional chelator and the conjugate will be fully characterized with radio-LC-HRMS. Next the nanobody will be labeled with $[Al^{18}F]^{2+}$ in aqueous buffer at room temperature, conditions that are compatible with heat sensitive biomolecules.

Materials and Methods

Generic nanobody (3 mg) in 0.05 M sodium bicarbonate pH 8.6 (1.5 ml, 2% DMSO) was added to H$_3$L28 (20-fold molar excess) and incubated for 2 h at room temperature. The conjugate was successfully purified by gel filtration and the concentration of H$_3$L26-nanobodies was determined spectrophotometrically at 280 nm. The nanobody contains three lysine residues in its amino acid sequence and also the terminal amino group is accessible. Consequently, the active ester can react with multiple free amino functionalities of the nanobody. A chelator-to-protein ratio of 3.5 was estimated by ESI-TOF-HRMS analysis.

The construct was successfully labeled with $\{A\ 8F\}^{2+}$ with an estimated RCY of 30% (~15 nmol of nanobody) and purified manually via size exclusion (PD-10).

Conclusion

We successfully labeled for the first time a heat sensitive biomolecule via the Al$^{18}$F-method in one radiolabelling step. In less than 30 minutes the nanobody was radiolabeled and ready to use for preclinical studies. Moreover we were able to fully characterize the labeled nanobody with radio-LC-HRMS in order to assure that the radiolabeling procedure did not affect the nanobody's integrity. We are confident that this new class of AlF-chelators will have a great impact on PET radiochemical space as it will stimulate the rapid development of other fluorine-18 labeled heat-sensitive biomolecules.

Example 33: Derivatives of Ligand H$_3$L26: Synthesis, Reactivity and Stability of Ligands H$_3$L29, H$_3$L30, H$_3$L31 and H$_3$L32

Synthesis of Ligands H$_3$L29, H$_3$L30, H$_3$L31 and H$_3$L32

Synthesis of Ligand H$_3$L29 (FIG. 2 and Scheme 18)

Step 1: Synthesis of Compound (±)-35 (di-tert-butyl 2,2'-(((1R,2S)-2-((2-(tert-butoxy)-2-oxoethyl)amino)cyclohexyl)azanediyl)diacetate)

To a solution of cis-1,2-diaminocyclohexane (300 mg; 2.63 mmol) in dichloromethane (10 mL) were successively added N,N-diisopropylethylamine (1.37 mL; 7.88 mmol; 3 eq.) and tert-butyl bromoacetate (1.16 mL; 7.88 mmol; 3 eq.). The mixture was stirred at RT overnight and then poured into a saturated aqueous sodium hydrogencarbonate solution (15 mL). After extractions with dichloromethane (3×15 mL), the organic layers were combined, dried over magnesium sulfate, filtered and evaporated under reduced pressure. The crude product was purified by column chromatography (silica, ethyl acetate/heptane 1:9-) 1:1) to yield (±)-35 (684 mg; 1.50 mmol) as a pale orange oil. Yield: 57%. Rf (silica; ethyl acetate/heptane 1:2) 0.55; $^1$H NMR (400 MHz, CDCl$_3$) 1.11-1.26 (m, 3H, H-4, H-5, H-6), 1.38-1.46 (m, 28H, H-3, (CH$_3$)$_3$), 1.51-1.63 (m, 2H, H-3, H-5), 1.70-1.80 (m, 2H, H-4, H-6), 2.51 (bs, 1H, NH), 2.80-2.81 (m, 1H, H-1), 2.87 (dt, 1H, J=11.8 Hz, J=3.5 Hz, H-2), 3.12 (d, 1H, J=17.2 Hz, H-a), 3.27 (d, 1H, J=17.2 Hz, H-a), 3.41 (d, 2H, J=17.7 Hz, H-b, H-c), 3.49 (d, 2H, J=17.7 Hz, H-b, H-c); $^{13}$C NMR (101 MHz, CDCl$_3$) 18.8 (C-5), 25.0 (C-3), 25.7 (C-4), 27.8 (C-6), 28.2 and 28.2 (9C, C(CH$_3$)$_3$), 49.8 (C-a), 53.5 (2C, C-b, C-c), 53.7 (C-1), 62.6 (C-2), 80.5 (C-d), 80.7 (2C, C-e, C-f), 171.8 (2C, C=O), 172.1 (C=O).

Step 2: Synthesis of Compound (±)-36 (di-tert-butyl 2,2'-(((1R,2S)-2-((2-(tert-butoxy)-2-oxoethyl)(methyl)amino)cyclohexyl)azanediyl)diacetate)

To a solution of (±)-35 (350 mg; 0.77 mmol) in methanol (2.5 mL) was slowly added paraformaldehyde (69 mg; 2.30 mmol; 3 eq.). The mixture was then heated at 65° C. for 1 h, and cooled to 0° C. Sodium cyanoborohydride (63 mg; 1.00 mmol; 1.3 eq.) was added portionwise and the mixture was stirred at room temperature for 3 h. After dilution, the crude product was purified by column chromatography (silica, ethyl acetate/heptane 1:9→3:7) to yield (±)-36 (148 mg; 0.32 mmol) as a pale yellow oil. Yield: 42%. Rf (silica; ethyl acetate/heptane 1:4) 0.45; HRMS (ESI): Calcd. for C$_{25}$H$_{46}$N$_2$O$_6$ [M+H$^+$] 471.3429; found 471.3451; 1H NMR (400 MHz, CDCl$_3$): 1.25-1.79 (m, 35H, H-3, H-3, H-4, H-4, H-5, H-5, H-6, H-6, (CH$_3$)$_3$), 2.41 (s, 3H, CH$_3$), 2.75-2.82 (m, 1H, H-1 or H-2), 3.26-3.30 (m, 1H, H-1 or H-2), 3.46-3.70 (m, 6H, CH$_2$-a, b, c); $^{13}$C NMR (101 MHz, CDCl$_3$) (number of carbon(s) for each signal are not mentioned because some signals are low due to the chemical structure) 21.9, 24.7, 25.5, 28.3, 40.5, 54.4, 56.3, 57.3, 64.0, 80.4, 172.2.

Step 3: Synthesis of Compound H$_3$L29

A solution of (±)-36 (130 mg; 0.28 mmol) in trifluoroacetic acid (2.5 mL) was stirred at RT overnight. The solvent was then evaporated under reduced pressure. The sample was then taken up in diethyl ether (5 mL) and the solvent was evaporated under reduced pressure. The obtained residue was then dried under vacuum to give H$_3$L29 (114 mg; 0.21 mmol) as a white solid. Yield: 75%; HRMS (ESI): Calcd. for C$_{13}$H$_{22}$N$_2$O$_6$ [M+H$^+$] 303.1551; found 303.1550; $^1$H NMR (400 MHz, D$_2$O) 1.40-2.00 (m, 8H, H-3, H-3, H-4, H-4, H-5, H-5, H-6, H-6), 2.97 (s, 3H, CH$_3$), 3.23-3.28 (m, 1H, H-1 or H-2), 3.46-3.51 (m, 1H, H-1 or H-2), 3.57 (d, 2H, J=18.6 Hz, H-b, H-c), 3.78 (d, 2H, J=18.6 Hz, H-b, H-c), 4.05-4.20 (m, 2H, H-a); $^{13}$C NMR (101 MHz, D$_2$O) (some signals are low due to the chemical structure) (signals of TFA are not described) 22.2 (C-3 or 4 or 5 or 6), 22.4 (C-3 or 4 or 5 or 6), 22.8 (C-3 or 4 or 5 or 6), 25.2 (C-3 or 4 or 5 or 6), 41.7 (CH$_3$), 55.0 (C-a, b, c), 59.4 (C-1 or 2), 65.3 (C-1 or 2), 169.2 (C=O), 176.8 (C=O).

Synthesis of Ligand H$_3$L30 (FIG. 2 and Scheme 19)

Step 1: Synthesis of Compound 37 (di-tert-butyl 2,2'-(((1R,6R)-6-(benzyl(2-(tert-butoxy)-2-oxoethyl) amino)cyclohex-3-en-1-yl)azanediyl)diacetate)

To a solution of (1R,2R)-4-Cyclohexene-1,2-diamine, (0.87 g, 4.7 mmol) in methanol (MeOH) (10 mL), benzaldehyde (0.1 g, 0.94 mmol) was added. The mixture was stirred for 2 h at 65° C. The mixture was then cooled on an ice bath to 0° C. Next, sodium borohydride (36 mg, 0.94 mmol) was gradually added to the mixture, during which time the solution was allowed to reach RT. The solvent was evaporated and an aqueous saturated solution of sodium carbonate (10 mL) was added. The product was extracted three times using equal volumes of dichloromethane (DCM). The combined organic layers were then dried with magnesium sulfate and evaporated under reduced pressure. The compound was used without further purification. DCM (10 mL) N,N-Diisopropylethylamine (DIPEA) (0.5 ml, 2.82 mmol) and tert-butyl bromoacetate (0.55 g, 2.82 mmol) were successively and slowly added. The mixture was then stirred at RT for 12 h. The solution was filtered and the solvent removed under vacuum. A saturated solution of NaHCO$_3$ (50 mL) was added and the product was extracted three times with DCM (20 mL). The obtained oil was purified using flash chromatography on silica gel (ethyl acetate/heptane, 1:3) affording pure product (±)-37 (0.186 g, 36%). HRMS (ESI): Calcd. for C$_{31}$H$_{48}$N$_2$O$_6$ [M+H$^+$] 545.3512; found 545.3497. $^1$H NMR (400 MHz, CDCl3) δ 7.50-7.36 (m, 2H), 7.33-7.16 (m, 3H), 5.55 (s, 2H), 4.05 (d, J=13.1 Hz, 1H), 3.95 (d, J=13.3 Hz, 1H), 3.66 (d, J=13.1 Hz, 1H), 3.41 (d, J=16.7 Hz, 1H), 3.32 (d, J=20.0 Hz, 1H), 3.23 (d, J=17.5 Hz, 1H), 3.09 (td, J=9.9, 4.9 Hz, 1H), 2.92 (td, J=9.9, 5.2 Hz, 1H), 2.50-2.33 (m, 2H), 2.21-2.07 (m, 1H), 2.07-1.92 (m, 1H), 1.44 (s, 18H), 1.42 (s, 9H). $^{13}$C NMR (101 MHz, CDCl3) δ 172.7, 172.3, 130.0, 128.7, 128.7, 127.5, 126.4, 126.3, 81.1, 80.9, 60.6, 58.1, 57.8, 55.1, 55.0, 53.5, 53.1, 52.6, 28.8.

Step 2: Synthesis of Compound H$_3$L30 (2,2'-(((1R, 6R)-6-(benzyl(carboxymethyl)amino)cyclohex-3-en-1-yl)azanediyl)diacetic Acid)

Compound (±)-36 (0.186 g, 0.34 mmol) was stirred in trifluoroacetic acid (TFA) (2 mL) at RT for 12 h. The deprotection was monitored over time using LC-MS until full conversion of compound (±)-36 was established. Afterwards, the solvent was evaporated under reduced pressure affording pure H$_3$L27 (0.180 mg, 87%). HRMS (ESI): Calcd. for C$_{19}$H$_{24}$N$_2$O$_6$ [M+H$^+$]377.1634; found 377.1662.

Synthesis of Ligand H$_3$L31 (FIG. 2 and Scheme 20)

Step 1: Synthesis of Compound (±)-38 (tert-butyl ((1R,2R)-2-(benzylamino)cyclopentyl)carbamate)

To a solution of (1R,2R)-trans-N-Boc-1,2-cyclo-pentanediamine (0.1 g, 0.5 mmol) in methanol (MeOH) (2 mL), benzaldehyde (53 mg, 0.5 mmol) was added. The mixture was stirred for 2 h at 65° C. The mixture was then cooled on an ice bath to 0° C. Next, sodium borohydride (19 mg, 0.5 mmol) was gradually added to the mixture, during which time the solution was allowed to reach RT. The solvent was evaporated and an aqueous saturated solution of sodium carbonate (10 mL) was added. The product was extracted three times using equal volumes of dichloromethane (DCM). The combined organic layers were then dried with magnesium sulfate and evaporated under reduced pressure. The obtained oil was purified using flash chromatography on silica gel (ethyl acetate) affording pure product (±)-38 (37 mg, 26%). HRMS (ESI): Calcd. for C$_{17}$H$_{26}$N$_2$O$_6$ [M+H$^+$] 291.1994; found 291.2007. $^1$H NMR (400 MHz, CDCl3) δ 7.33-7.29 (m, 4H), 7.26-7.20 (m, 1H), 3.86 (d, J=13.4 Hz, 1H), 3.75 (d, J=13.4 Hz, 1H), 2.11 (td, J=13.4, 7.8 Hz, 1H), 1.93 (td, J=13.2, 7.7 Hz, 1H), 1.80-1.73 (m, 1H), 1.70-1.55 (m, 2H), 1.51-1.47 (m, 1H), 1.45 (s, 9H), 1.42-1.32 (m, 2H). $^{13}$C NMR (101 MHz, CDCl3) δ 155.9, 140.7, 128.4, 128.2, 126.9, 79.3, 65.2, 57.9, 52.2, 31.8, 31.3, 28.5, 21.8.

Step 2: Synthesis of Compound (+)-39 (di-tert-butyl 2,2'-(((1R,2R)-2-(benzyl(2-(tert-butoxy)-2-oxoethyl)amino)cyclopentyl)azanediyl)diacetate)

To a solution of (±)-38 (35 mg, 0.12 mmol) in DCM (5 mL), TFA (2 mL) was added and stirred for 2 h at RT. After removing the solvent, a solution of N,N-Diisopropylethylamine (DIPEA) (210 ml, 1.2 mmol) and tert-butyl bromoacetate (72 mg, 0.36 mmol) in DCM (2 mL) was slowly added. The mixture was then stirred at RT for 12 h. The solution was filtered and the solvent removed under vacuum. A saturated solution of NaHCO$_3$ (50 mL) was added and the product was extracted three times with DCM (20 mL). The obtained oil was purified using flash chromatography on silica gel (ethyl acetate/heptane, 1:3) affording pure product (±)-39 (39 mg, 62%). HRMS (ESI): Calcd. for C$_{30}$H$_{48}$N$_2$O$_6$ [M+H$^+$] 533.3512; found 533.3551. $^1$H NMR (400 MHz, CDCl3) δ 7.37 (d, J=7.2 Hz, 2H), 7.31-7.19 (m, 3H), 3.89 (d, J=13.4 Hz, 1H), 3.70 (d, J=17.4 Hz, 2H), 3.50 (d, J=17.4 Hz, 2H), 3.45-3.34 (m, 1H), 3.33-3.21 (m, 2H), 3.14 (d, J=16.5 Hz, 1H), 1.88-1.49 (m, 6H), 1.44 (s, 18H), 1.42 (s, 9H). $^{13}$C NMR (101 MHz, CDCl3) δ 171.6, 171.5, 139.4, 129.3, 128.3, 127.1, 80.6, 80.6, 66.8, 65.2, 55.9, 54.0, 53.2, 29.7, 28.3, 28.3, 25.4, 22.7.

Step 3: Synthesis of Compound H$_3$L31 (2,2'-(((1R, 2R)-2-(benzyl(carboxymethyl)amino)cyclopentyl) azanediyl)diacetic Acid)

Compound (±)-39 (39 mg, 0.07 mmol) was stirred in trifluoroacetic acid (TFA) (1 mL) at RT for 12 h. The deprotection was monitored over time using LC-MS until full conversion of compound (+)-31 was established. Afterwards, the solvent was evaporated under reduced pressure affording pure H$_3$L31 (30 mg, 70%). HRMS (ESI): Calcd.

for $C_{18}H_{24}N_2O_6$ [M+H+]365.1634; found 365.1654; $^1$H NMR (400 MHz, D2O) δ 7.46-7.41 (m, 2H), 7.40-7.31 (m, 3H), 4.44 (dd, J=13.0, 4.4 Hz, 1H), 4.30 (dd, J=12.9, 4.6 Hz, 1H), 4.10 (dd, J=17.3, 3.9 Hz, 1H), 3.99 (dd, J=17.2, 3.4 Hz, 1H), 3.86-3.71 (m, 1H), 3.72-3.47 (m, 5H), 2.17-2.05 (m, 1H), 1.95-1.84 (m, 1H), 1.84-1.64 (m, 3H), 1.64-1.50 (m, 1H). $^{13}$C NMR (101 MHz, D2O) δ 173.7, 169.6, 163.8, 163.5, 163.1, 162.8, 131.7, 131.1, 130.1, 129.3, 121.2, 118.3, 115.4, 112.5, 66.5, 65.5, 60.2, 53.4, 50.6, 23.0, 20.1. $^{19}$F NMR (376 MHz, D2O) δ −75.7.

Synthesis of Ligand $H_3L32$ (FIG. 2 and Scheme 21)

Step 1: Synthesis of Compound 44 (N-Benzylbenzene-1,2-Diamine)

To a solution of compound o-phenyldiamine (400 mg, 3.68 mmol) in ACN (60 mL) brenzyl bromide (632 mg, 3.68 mmol) was slowly added. The mixture was then stirred at 40° C. for 24 h. A saturated solution of NaHCO3 (50 mL) was added and the product was extracted three times with DCM (20 mL). The obtained oil was purified using flash chromatography on silica gel (ethyl acetate/heptane, 1:2) affording pure product 44 (200 mg, 30%). HRMS (ESI): Calcd. for $C_{13}H_{14}N_2$[M+H+] 199.1230; found 199.1236. $^1$H NMR (400 MHz, CDCl3) δ 7.44-7.27 (m, 5H), 6.85-6.79 (m, 1H), 6.77-6.67 (m, 3H), 4.35 (d, J=20.1 Hz, 2H). $^{13}$C NMR (101 MHz, CDCl3) δ 139.6, 137.8, 134.3, 128.8, 127.9, 127.4, 120.9, 119.0, 116.7, 112.2, 48.8.

Step 2: Synthesis of Compound 45 (di-tert-butyl 2,2'-((2-(benzyl(2-(tert-butoxy)-2-oxoethyl)amino) phenyl)azanediyl)diacetate)

To a solution of compound 44 (200 mg, 1.01 mmol) in Dry ACN (30 mL) N,N-Diisopropylethylamine (DIPEA) (0.6 ml, 3.5 mmol) and tert-butyl bromoacetate (0.7 g, 3.5 mmol) were successively and added. The mixture was refluxed for 12 h. The solution was filtered and the solvent removed under vacuum. A saturated solution of NaHCO3 (50 mL) was added and the product was extracted three times with DCM (20 mL). The obtained oil was purified using flash chromatography on silica gel (ethyl acetate/ heptane, 1:19) affording pure product 45 (157 mg, 29%). HRMS (ESI): Calcd. for $C_{31}H_{44}N_2O_6$ [M+H+] 541.3272; found 541.3304. $^1$H NMR (400 MHz, CDCl3) δ 7.30-7.21 (m, 5H), 7.03-6.96 (m, 2H), 6.94-6.88 (m, 2H), 4.46 (s, 2H), 4.17 (s, 4H), 3.97 (s, 2H), 1.38 (s, 9H), 1.37 (s, 18H). 3C NMR (101 MHz, CDCl3) δ 170.7, 170.3, 142.2, 141.5, 138.1, 129.5, 128.4, 127.3, 122.6, 122.5, 121.8, 121.1, 81.2, 80.8, 55.5, 53.6, 51.5, 28.3, 28.2.

Step 3: Synthesis of Compound $H_3L32$ (2,2'-((2-(benzyl(carboxymethyl)amino)phenyl)azanediyl) diacetic Acid)

Compound 45 (100 mg, 0.18 mmol) was stirred at RT in 2 mL of TFA. The reaction was monitored by LC-MS. The solvent was removed under vacuum and diethyl ether was added. Compound $H_3L32$ was isolated as an oil (108 mg, 97%). HRMS (ESI): Calcd. for $C_{19}H_{20}N_2O_6$ [M+H+] 373.1393; found 373.1394. $^1$H NMR (400 MHz, D2O) δ 7.75 (dd, J=8.1, 1.2 Hz, 1H), 7.56-7.51 (m, 1H), 7.47 (td, J=7.8, 1.5 Hz, 1H), 7.36 (dd, J=8.0, 1.4 Hz, 1H), 7.32-7.25 (m, 1H), 7.13 (t, J=7.6 Hz, 2H), 6.99-6.91 (m, 2H), 4.79 (s, 8H). $^{13}$C NMR (101 MHz, D2O) δ 173.4, 168.4, 143.2, 135.7, 132.1, 131.3, 130.7, 129.6, 129.2, 128.3, 126.7, 121.1, 64.4, 58.3, 56.2.

Reactivity of Ligands $H_3L29$, $H_3L30$, $H_3L31$ and $H_3L32$

Production of Aqueous Solution of [$^{18}$F]fluoride and $\{Al^{18}F\}^{2+}$

After cyclotron production, [$^{18}$F]F− was separated from [$^{18}$O]H2O by trapping on a SepPak™ Light Accel plus QMA anion exchange cartridge (Cl− form; Waters, Milford, USA). The [$^{18}$F]F− (148-333 MBq) was eluted from the cartridge with an aqueous solution of sodium chloride 0.9% (0.4 mL). This aqueous solution of [$^{18}$F]fluoride (50 μl) was added to 22.5 μl of 2 mM aluminum chloride (AlCl3) in sodium acetate buffer (0.1 M, pH 4). The solution was incubated at RT for 5 min to form $\{Al^{18}F\}^{2+}$.

Production and Purification of [Al$^{18}$F]-$H_3L29$, [Al$^{18}$F]-$H_3L30$, [Al$^{18}$F]-$H_3L31$ and [Al$^{18}$F]-$H_3L32$ A solution of each ligand (1 mL, 150 μM) in sodium acetate buffer (0.1 M, pH 4) was added to a vial which contained a freshly prepared $\{Al^{18}F\}^{2+}$ solution. The vials were heated at different temperatures for 12 min and the radiochemical yields were determined by iTLC-SG.

The resulting mixtures were purified with a Sep-Pak® Plus Alumina-N-Cartridge (Waters, Milford, USA). The cartridge was pre-rinsed with an aqueous solution of sodium chloride 0.9% (5 mL) and the crude reaction mixture was loaded on the column. The cartridge was then rinsed with an aqueous solution of sodium chloride 0.9% (3 mL). The eluate was collected and each of the purified ligand-[Al$^{18}$F]$^{2+}$ complex solutions was analysed using iTLC-SG and radio-HPLC-HRMS.

The radiochemical yields (RCY's) derived from iTLC-SG analyses at different temperatures are represented in FIG. 24. All ligands showed efficient chelation of $\{Al^{18}F\}^{2+}$ at all tested temperatures with RCY's higher than 60%. The radiochemical purity after purification for all ligands was >98%.

Stability tests of Al$^{18}$F-L26, [Al$^{18}$F]-$H_3L29$, [Al$^{18}$F]-$H_3L30$, [Al$^{18}$F]-$H_3L31$ and [Al$^{18}$F]-$H_3L32$ in PBS (0.1 M, pH 7.4) and Rat Serum 100 μl of [Al$^{18}$F]-L26, [Al$^{18}$F]-$H_3L29$, [Al$^{18}$F]-$H_3L30$, [Al$^{18}$F]-$H_3L31$ or [Al$^{18}$F]-$H_3L32$ was added to 400 μl of PBS or 400 μl of rat serum. These mixtures were incubated at 37° C. and analysed by iTLC-SG at 10, 30, 60, 120, 180 and 240 min after the start of the incubation (N=3). Serum samples were denatured by addition of 50 μl of the serum solution to 50 μl of acetonitrile. The mixture was stirred and centrifuged (1300 g, 3 min). Finally the supernatant was analysed using iTLC-SG. The results of the stability experiment in PBS (0.1M, pH7) and rat serum at 37° C. are shown in FIG. 25 where the percentage intact tracer is displayed as a function of time. Al$^{18}$F-L26 exhibited excellent stability in both PBS and rat serum, the observed percentage intact tracer in rat serum was 98±2.3% and 91±2.4% after one and four hours respectively. Al$^{18}$F-L29 and Al$^{18}$F-L30 displayed only moderate stability in PBS and rat serum. After four hours incubating in rat serum, 37±0.6% of Al$^{18}$F-L29 and 36±14.6% of Al$^{18}$F-L30 remained intact. On the other hand, Al$^{18}$F-L31 and Al$^{18}$F-L32 were unstable in PBS and rat serum, the percentage intact tracer dropped to 0% in 60 minutes.

Example 34: Synthesis of Ligands H$_3$L16 and H$_3$L17

Synthesis of Ligand H$_3$L16 (FIG. 2 and Scheme 21)

Step 1: Synthesis of Compound 40 (2-(((2-(benzylamino)ethyl)amino)methyl)phenol)[19]

A mixture of 2-hydroxy-3-nitrobenzaldehyde (0.112 g, 0.67 mmol) and N-benzylethylenediamine (0.100 g, 0.67 mmol) was heated in methanol (2 mL) at 50° C. for 60 min. The solvent was then evaporated under reduced pressure, and the residue was suspended in ethanol (2 mL). Then, sodium borohydride (0.026 g, 0.67 mmol) was added. The reaction mixture was stirred at RT for 12 h and the precipitate filtered and washed with water affording compound 40 as a yellow powder (0.156 g, 62%). HRMS (ESI): Calcd. for $C_{16}H_{19}N_3O_3$ [M+H$^+$] 302.1499; found 302.1498. $^1$H NMR (400 MHz, CDCl$_3$) 7.99 (1H, d, J 7.8), 7.24-7.17 (4H, m), 7.16-7.10 (2H, m), 6.54-6.46 (1H, m), 3.96 (2H, s), 3.58 (2H, s), 2.88-2.82 (2H, m), 2.82-2.73 (2H, m). $^{13}$C NMR (101 MHz, CDCl$_3$) δ 139.2, 136.7, 135.9, 128.6, 128.2 (2C), 127.4, 127.3, 126.5, 112.4, 53.3, 50.7, 45.9, 45.6.

Step 2: Synthesis of Compound 41 (tert-butyl 2-(benzyl(2-((2-(tert-butoxy)-2-oxoethyl)(2-hydroxybenzyl)amino)ethyl)amino)acetate)

To a solution of compound 40 (0.08 g, 0.26 mmol) in dichloromethane (4 mL) DIPEA (95 ⍰L, 0.53 mmol) and tert-butyl bromoacetate (0.206 g, 1.06 mmol) were successively and slowly added at 0° C. The mixture was then stirred at RT for 12 h. The solution was filtrated and the solvent removed in vacuum. The obtained oil was purified using flash chromatography on silica gel (ethyl acetate/heptane, 1:3) affording pure product 41 (0.119 g, 88%). HRMS (ESI): Calcd. for $C_{28}H_{40}N_2O_5$ [M+H$^+$] 485.3010; found 485.3028. $^1$H NMR (400 MHz, CDCl$_3$) δ 7.89 (dd, J=8.4, 1.6 Hz, 1H), 7.39 (dd, J=7.4, 1.6 Hz, 1H), 7.34-7.21 (m, 5H), 6.85 (dd, J=8.3, 7.4 Hz, 1H), 3.91 (s, 2H), 3.78 (s, 2H), 3.31 (s, 2H), 3.24 (s, 2H), 2.86-2.80 (m, 4H), 1.45 (s, 9H), 1.44 (s, 9H). $^{13}$C NMR (101 MHz, CDCl$_3$) δ 170.6, 170.1, 153.3, 138.6, 136.3, 135.5, 129.2, 128.4, 127.5, 127.3, 124.6, 118.7, 81.7, 81.1, 58.6, 55.2, 55.0, 54.6, 51.3, 51.1, 28.3, 28.2.

Step 3: Synthesis of Ligand H$_3$L16.HCl (2-(benzyl (2-((carboxymethyl)(2-hydroxybenzyl)amino)ethyl) amino)acetic Acid 2,2,2-trifluoroacetate Salt)

Compound 41 (0.119 g, 0.23 mmol) was stirred in 4N HCl in dioxane (2 mL) at RT for 12 h. The deprotection was monitored using LC-MS. Afterwards, the solvent was evaporated under reduced pressure affording compound H$_3$L16.2HCl (0.100 g, 89% yield). HRMS (ESI): Calcd. for $C_{20}H_{23}N_3O_7$ [M+H$^+$] 418.1609; found 418.1618. $^1$H NMR (400 MHz, D$_2$O) δ 8.27-8.13 (m, 1H), 7.76-7.67 (m, 1H), 7.53-7.35 (m, 5H), 7.20-6.99 (m, 1H), 4.44 (s, 4H), 4.06 (s, 2H), 3.92 (s, 2H), 3.77-3.67 (m, 2H), 3.59-3.48 (m, 2H). $^{13}$C NMR (101 MHz, D$_2$O) δ 170.0, 169.4, 153.5, 141.5, 134.9, 131.8, 131.3, 130.2, 129.0, 128.4, 121.2, 120.7, 60.6, 54.9 (2C), 54.2, 49.9 (2C).

Synthesis of Ligand H$_3$L17 (FIG. 2 and Scheme 22)

Step 1: Synthesis of Compound 42 (2-(((2-(benzylamino)ethyl)amino)methyl)phenol)

A mixture of 2-hydroxy-5-methoxy-benzaldehyde (0.100 g, 0.67 mmol) and N-benzylethylenediamine (0.100 g, 0.67 mmol) was heated in methanol (2 mL) at 50° C. for 60 min. The solvent was then evaporated under reduced pressure, and the residue was suspended in ethanol (2 mL). Then, sodium borohydride (0.026 g, 0.67 mmol) was added. The reaction mixture was stirred at RT for 12 h and the precipitate filtered and washed with water affording compound 42 as a yellow powder (0.149 g, 62%). HRMS (ESI): Calcd. for $C_{17}H_{22}N_2O_6$ [M+H$^+$] 287.1468; found 287.1482. $^1$H NMR (400 MHz, D$_2$O) δ 7.52-7.40 (m, 5H), 7.02-6.94 (m, 1H), 6.94-6.87 (m, 2H), 4.27 (s, 2H), 4.24 (s, 2H), 3.76 (s, 3H), 3.47-3.37 (m, 4H). $^{13}$C NMR (101 MHz, D$_2$O) δ 153.0, 149.8, 130.6, 130.5, 130.0, 118.1, 117.8, 117.6, 117.4, 56.7, 52.2, 48.0, 43.0, 43.0.

Step 2: Synthesis of Compound 43 (tert-butyl 2-(benzyl(2-((2-(tert-butoxy)-2-oxoethyl)(2-hydroxybenzyl)amino)ethyl)amino)acetate)

To a solution of compound 42 (93 mg, 0.26 mmol) in dichloromethane (4 mL) DIPEA (190 ⍰L, 1.04 mmol) and tert-butyl bromoacetate (0.100 g, 0.52 mmol) were successively and slowly added at 0° C. The mixture was then stirred at RT for 12 h. The solution was filtrated and the solvent removed in vacuum. The obtained oil was purified using flash chromatography on silica gel (ethyl acetate/heptane, 1:3) affording pure product 43 (53 mg, 40%). HRMS (ESI): Calcd. for $C_{29}H_{42}N_2O_6$ [M+H$^+$] 515.6536; found 515.6654. $^1$H NMR (400 MHz, CDCl$_3$) δ 7.38-7.18 (m, 5H), 6.83-6.68 (m, 2H), 6.55-6.48 (m, 1H), 3.79 (s, 2H), 3.76 (s, 2H), 3.27 (s, 2H), 3.23 (s, 2H), 2.92-2.80 (m, 2H), 2.80-2.69 (m, 2H), 1.45 (s, 18H). $^{13}$C NMR (101 MHz, CDCl$_3$) δ 170.6, 170.2, 152.5, 151.6, 138.6, 129.3, 128.4, 127.3, 122.7, 116.9, 115.0, 113.9, 81.7, 81.1, 58.5, 57.2, 55.8, 55.3, 54.9, 50.9, 50.8, 28.3, 28.2.

Step 3: Synthesis of Ligand H$_3$L17.HCl (2-(benzyl (2-((carboxymethyl)(2-hydroxybenzyl)amino)ethyl) amino)acetic acid 2,2,2-trifluoroacetate Salt)

Compound 43 (53 mg, 0.10 mmol) was stirred in 4N HCl in dioxane (2 mL) at RT for 12 h. The deprotection was monitored using LC-MS. Afterwards, the solvent was evaporated under reduced pressure affording compound H$_3$L17.2HCl (47 mg, 96% yield). HRMS (ESI): Calcd. for $C_{21}H_{27}N_3O_6$ [M+H$^+$] 403.1869; found 403.1901. $^1$H NMR (400 MHz, D$_2$O) δ 7.43-7.28 (m, 5H), 6.94-6.84 (m, 1H), 6.84-6.72 (m, 2H), 4.30 (s, 2H), 4.25 (s, 2H), 3.93-3.79 (m, 4H), 3.65 (s, 3H), 3.52 (s, 2H), 3.42 (s, 2H). $^{13}$C NMR (101 MHz, CDCl$_3$) δ 169.7, 169.7, 153.2, 150.3, 131.7, 131.2, 130.2, 129.0, 118.8, 118.2, 117.8, 116.4, 60.4, 56.6, 55.6, 55.2, 55.1, 49.7.

DRAWING DESCRIPTION

Brief Description of the Drawings

The present invention will become more fully understood from the detailed description given herein below and the accompanying drawings which are given by way of illustration only, and thus are not limitative of the present invention, and wherein.

Figure 1:
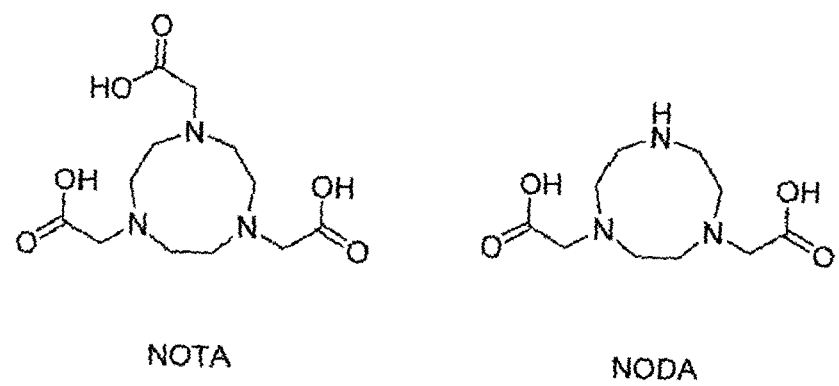
FIG. 1. displays the structural formulas of chelators 1,4,7-triazacyclononane-1,2,4-triacetic acid (NOTA) and 1,4,7-triazacyclononane-1,2-diacetic acid (NODA)
Figure 2:
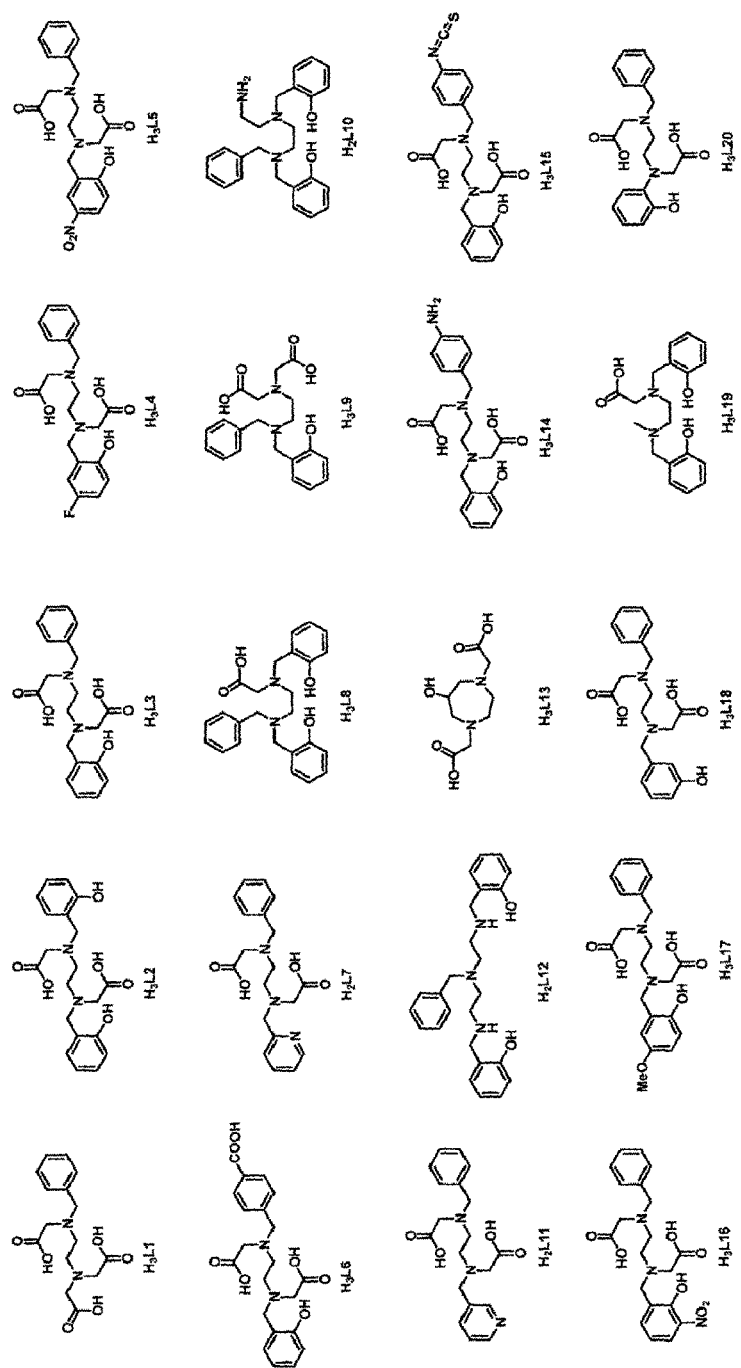
FIG. 2. displays the structural formulas of chelators H$_3$L1-31 and NODA-benzyl.
Figure 2:
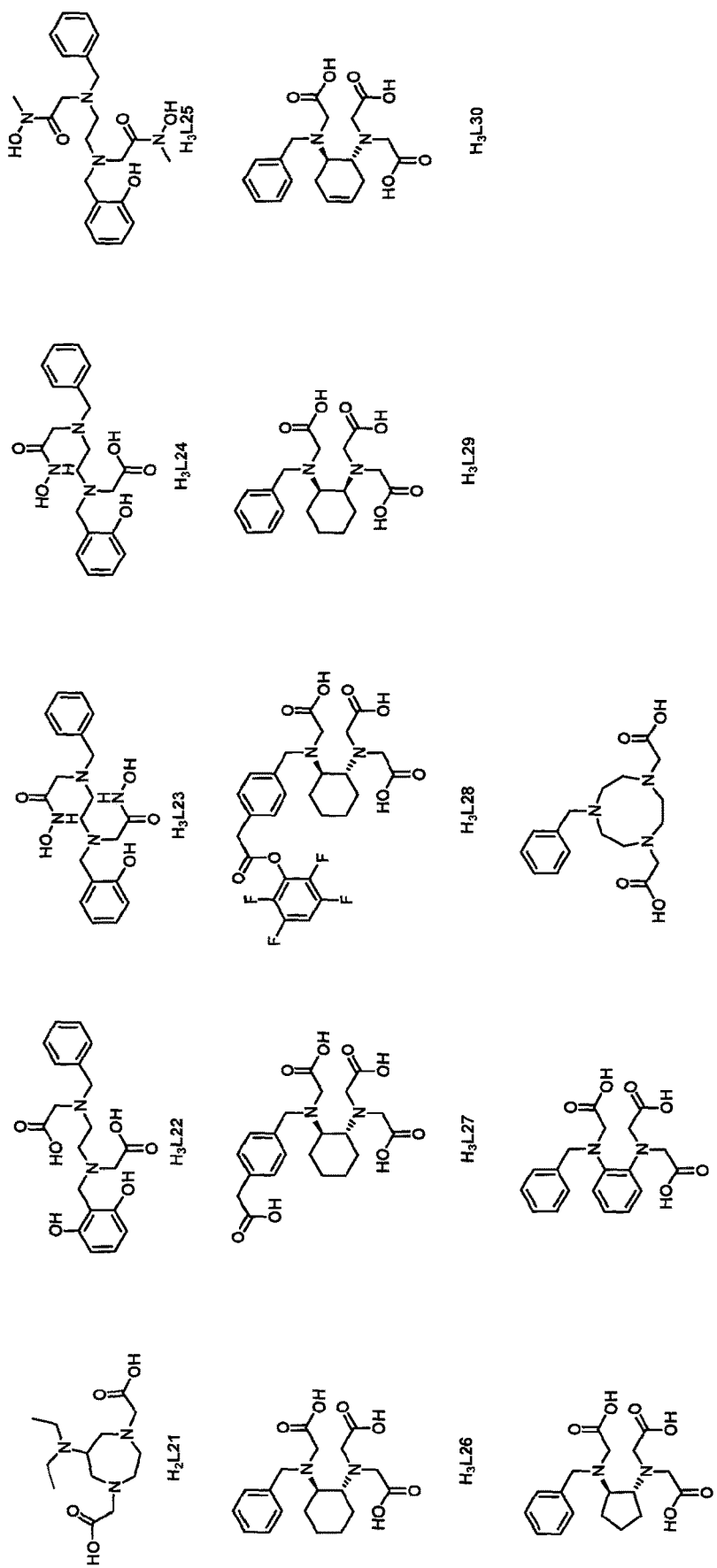
Figure 3:
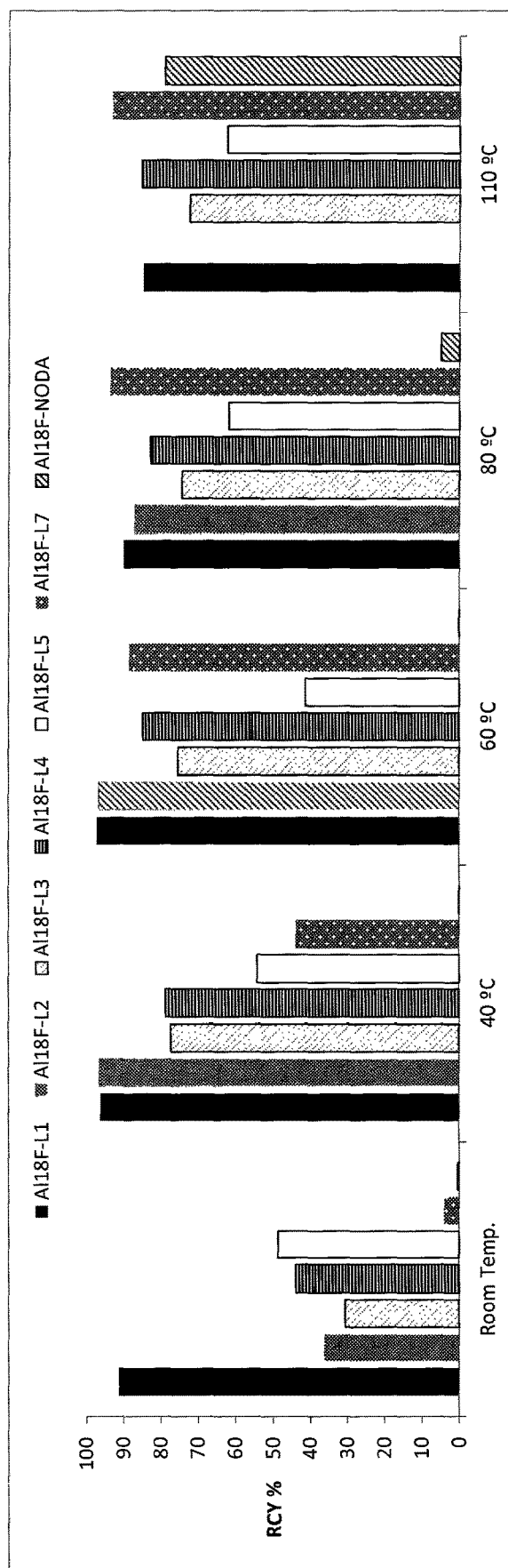
FIG. 3. provides in a graphic the radiochemical yields of the {Al$^{18}$F}-complexation with H$_3$L1, H$_3$L2, H$_3$L3, H$_3$L4, H$_3$L5, H$_2$L7 and H$_3$L9 at different temperatures. X-axis displays the reaction temperature, while the Y-axis displays the radiochemical yield in percent.
Figure 4:
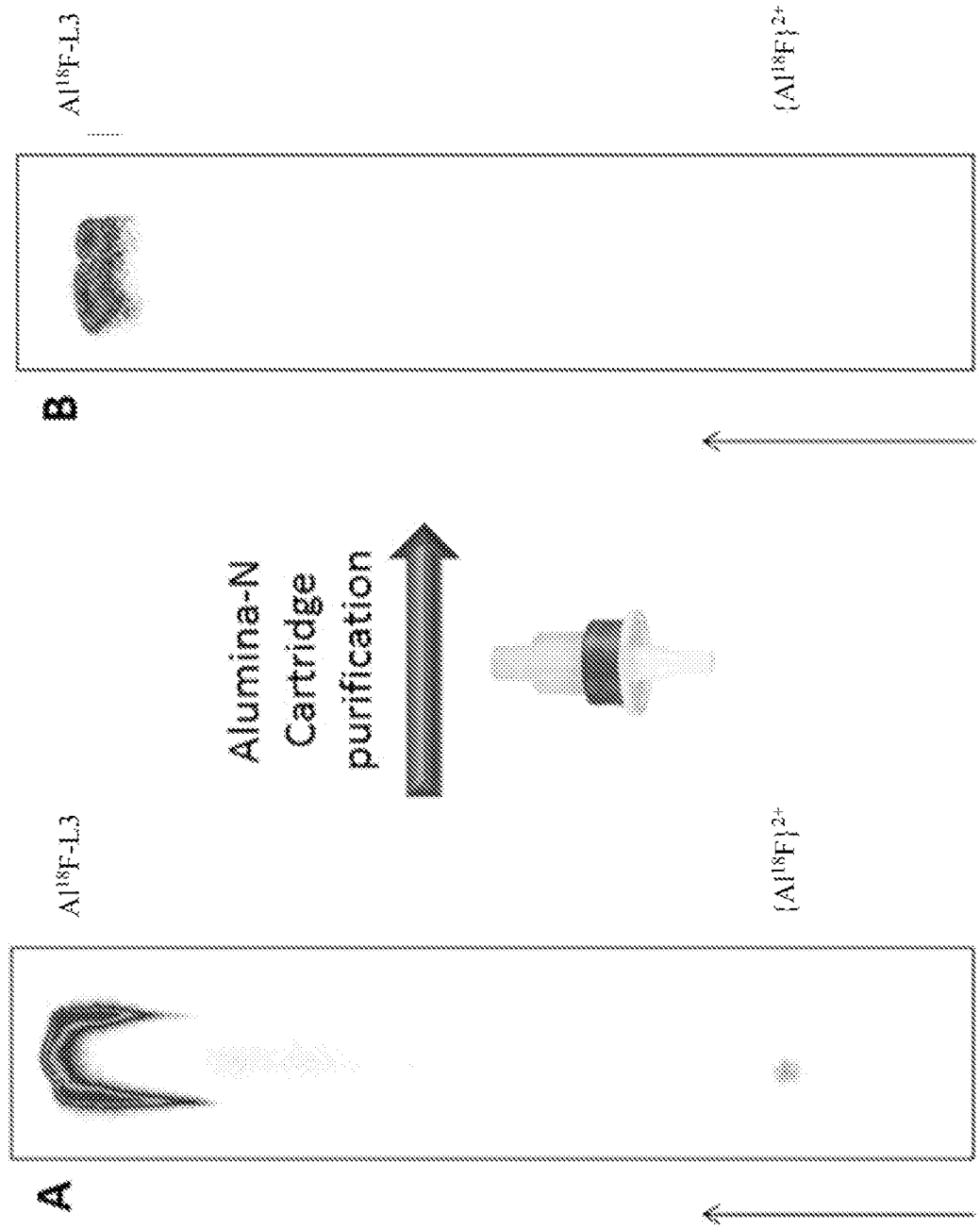
FIG. 4. shows the iTLC-SG analysis of [Al$^{18}$F]-L3, before (A) and after (B) alumina-N-cartridge purification. H$_3$L3 was labeled with {Al$^{18}$F}$^{2+}$. Labeling efficiency was 89.8% and the radiochemical purity after purification was 98.3%, both determined by ITLC-SG followed by autoradiography.
Figure 5:
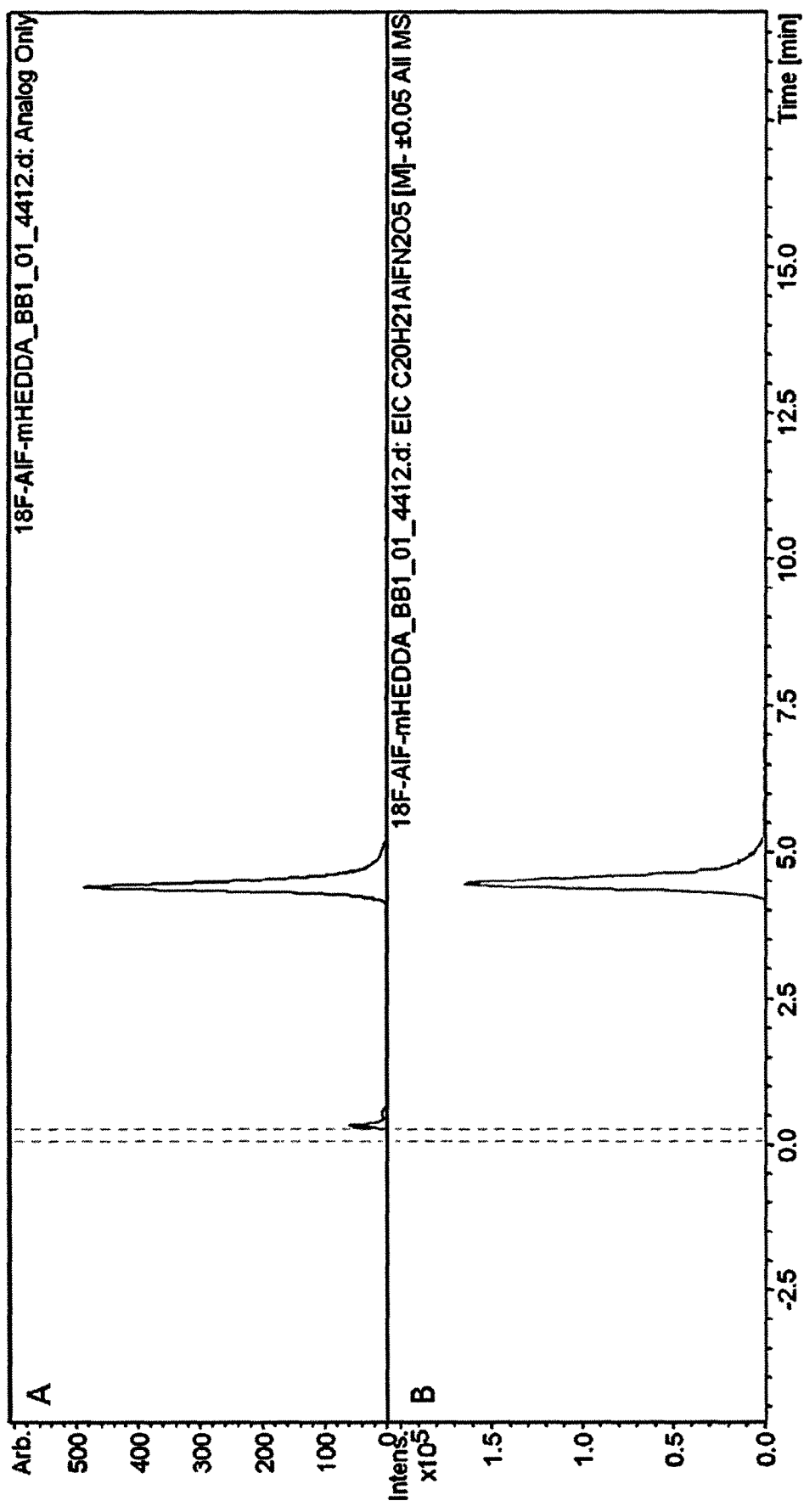
FIG. 5. is a graphic that shows the radio-HPLC-HRMS of Al$^{18}$F-L3 after purification (a) Radiometric channel; (b) Extracted ion chromatogram (ESI C$_{20}$H$_{21}$AlFN$_2$O$_5$±0.05); (c) spectrum view corresponding to peak Rt 4.4 min.
Figure 5:
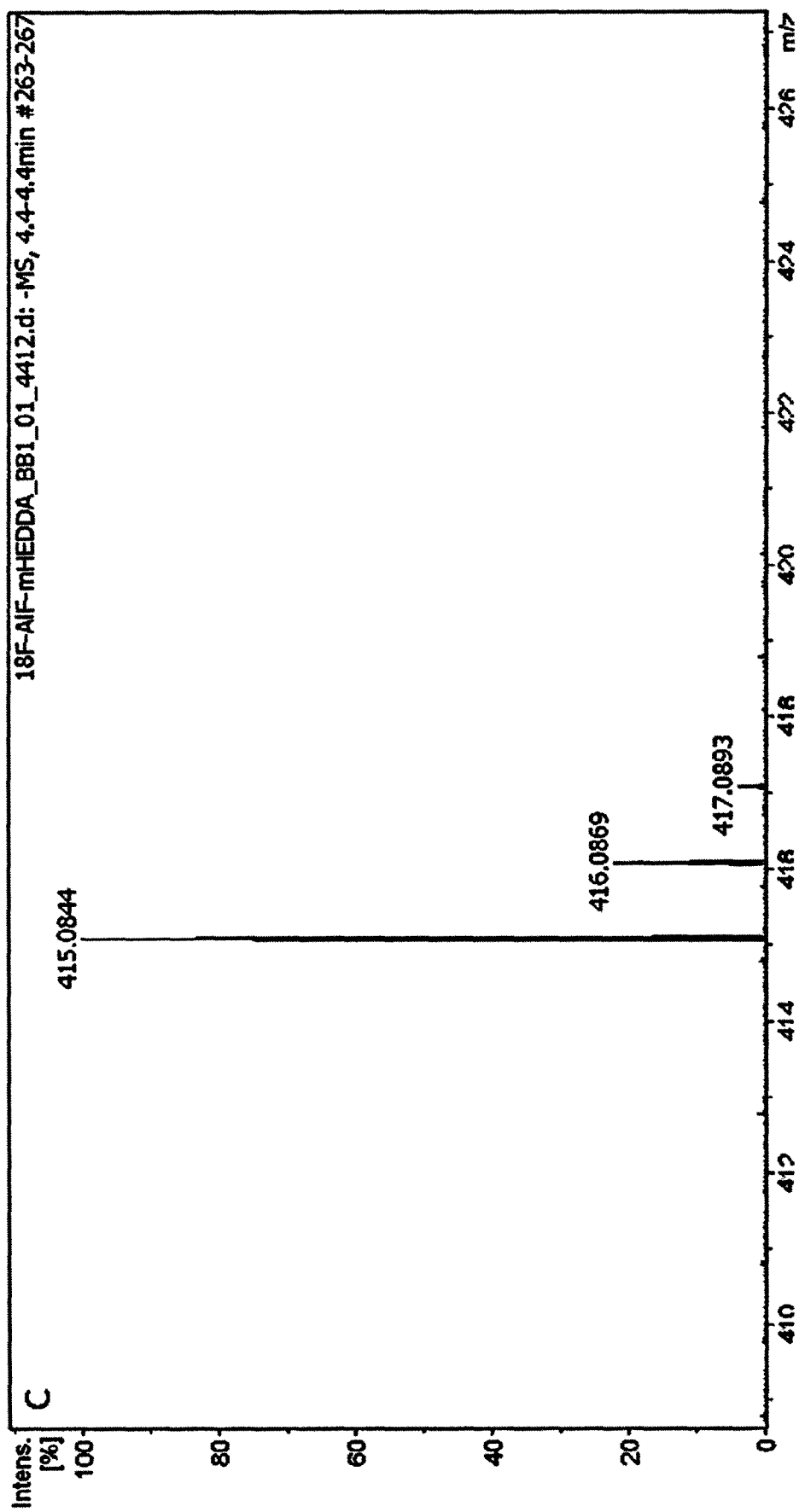
Figure 6:
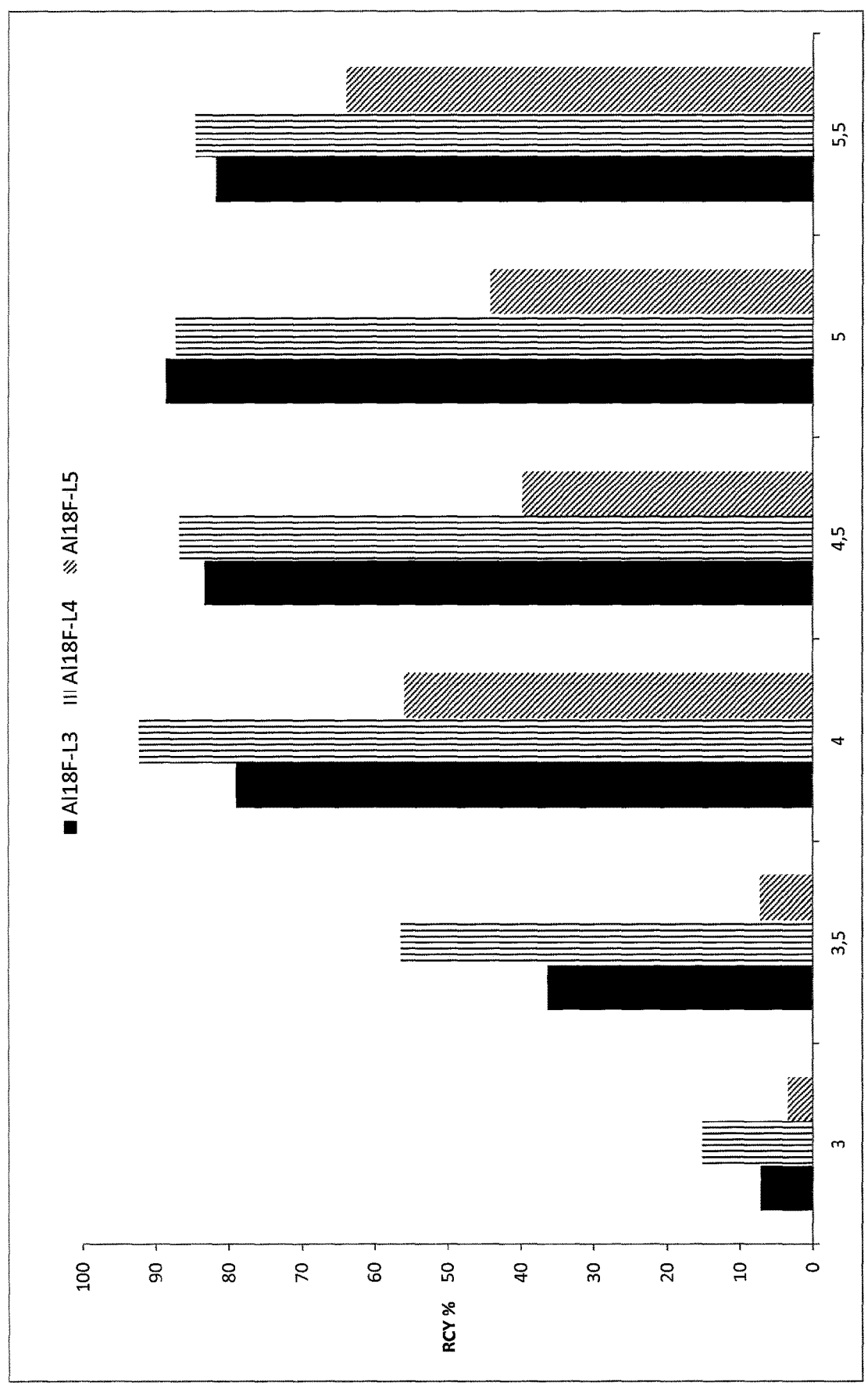
FIG. 6. provides in a graphic the radiochemical yields of the {Al$^{18}$F}-complexation with H$_3$L3, H$_3$L4 and H$_3$L5 at different pH. X-axis displays the pH of the reaction medium, while the Y-axis displays the radiochemical yield in percent.
Figure 7:
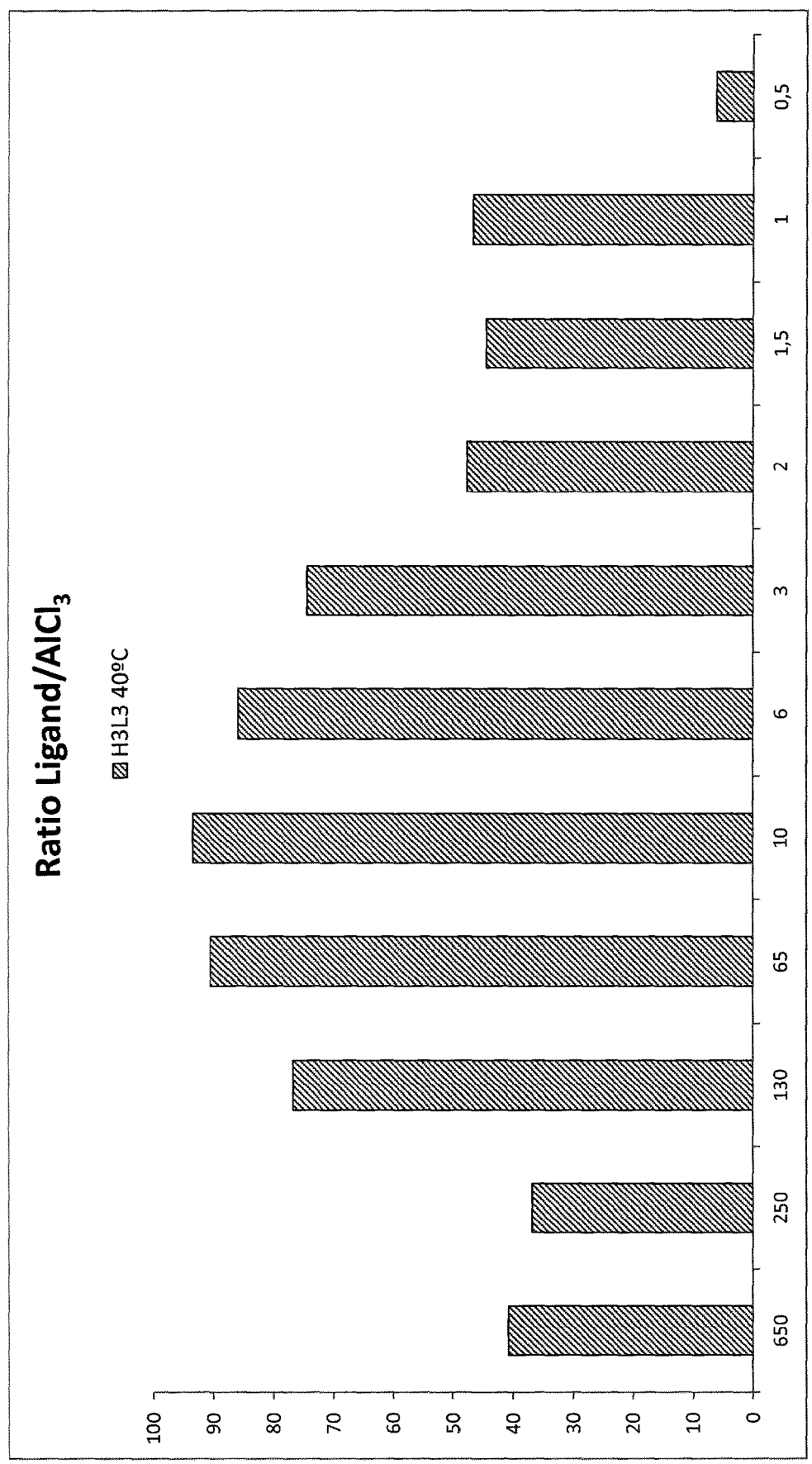
FIG. 7. provides in a graphic way the radiochemical yields of the {Al$^{18}$F}-complexation with H$_3$L3 when different H$_3$L3/AlCl$_3$ ratios are used. X-axis displays the H$_3$L3/AlCl$_3$ ratio, while the Y-axis displays the radiochemical yield in percent.
Figure 8:
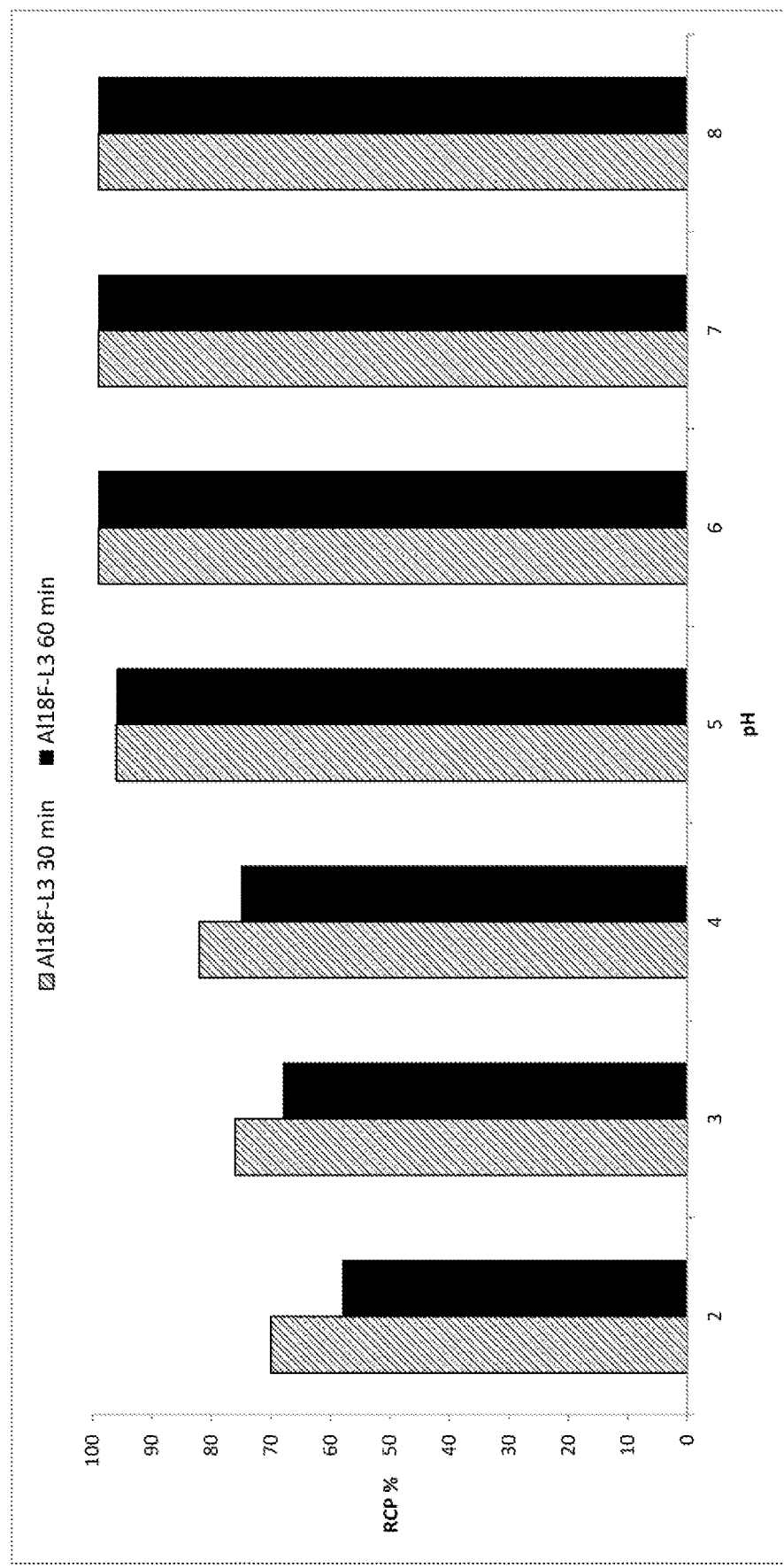
FIG. 8. provides a graph that shows the stability results of Al$^{18}$F-L3 at different pH FIG. 9. provides a graphic that shows the stability results of the aluminum fluoride complexes Al$^{18}$F-L1, Al$^{18}$F-L2, Al$^{18}$F-L3 and Al$^{18}$F-NODA in PBS over time. Radiochemical purity in percent is represented as a function of time.
Figure 9:
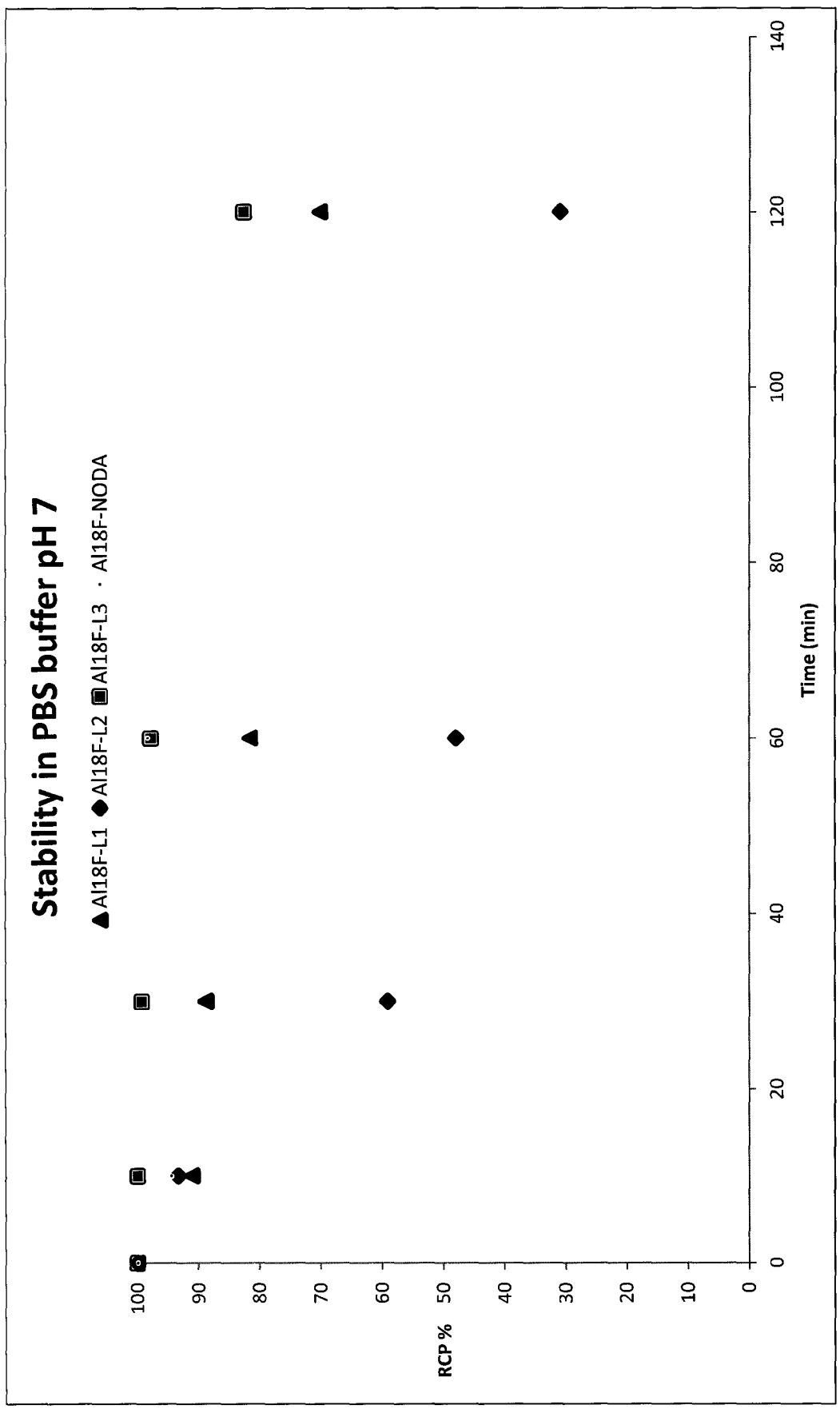
Figure 9:
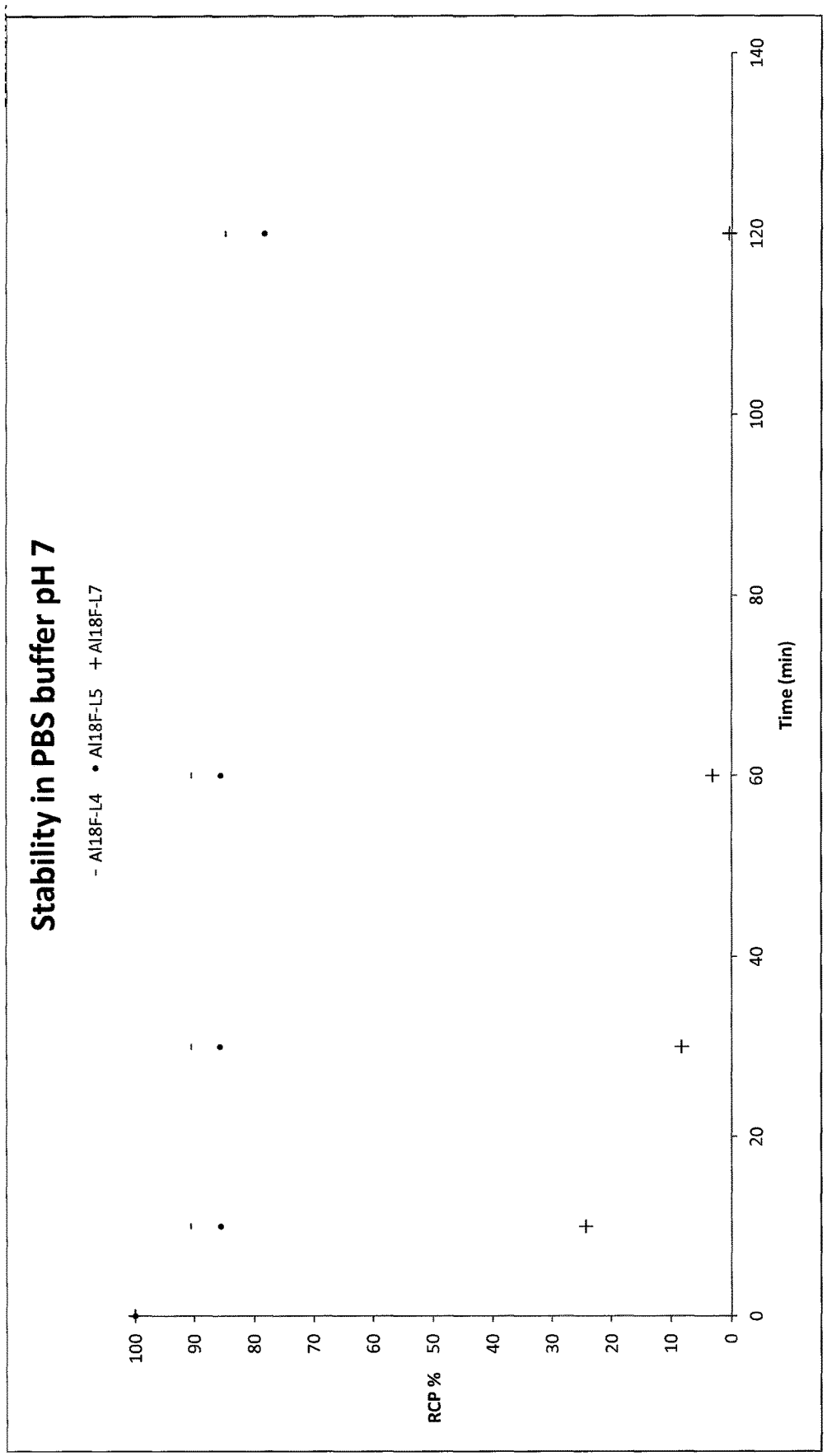
Figure 10:
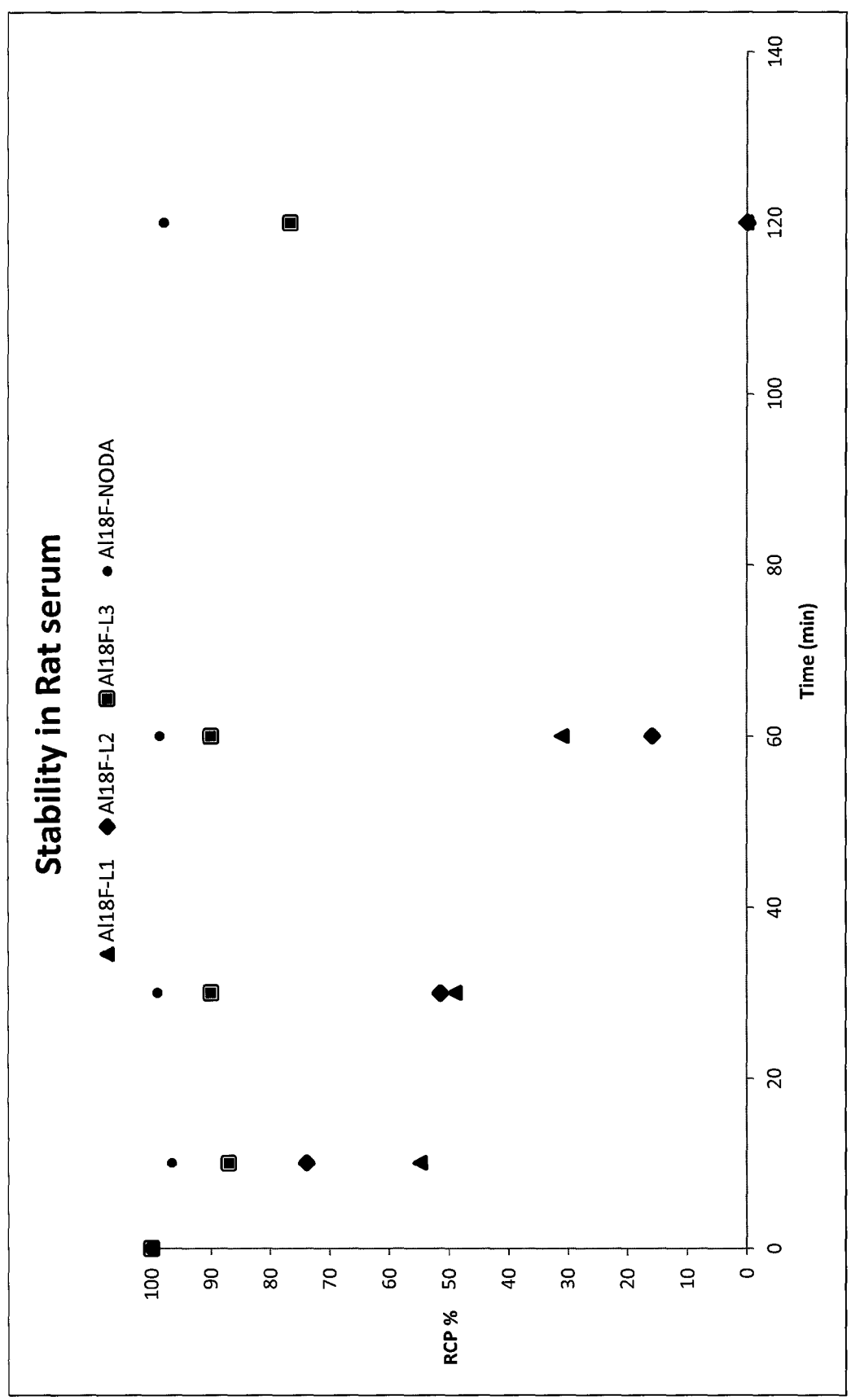
FIG. 10. provides a graphic that shows radiochemical purities of the aluminum fluoride complex Al$^{18}$F-L1, Al$^{18}$F-L2, Al$^{18}$F-L3 and Al$^{18}$F-NODA in rat serum over time. RCP in percent is represented as a function of time.
Figure 10:
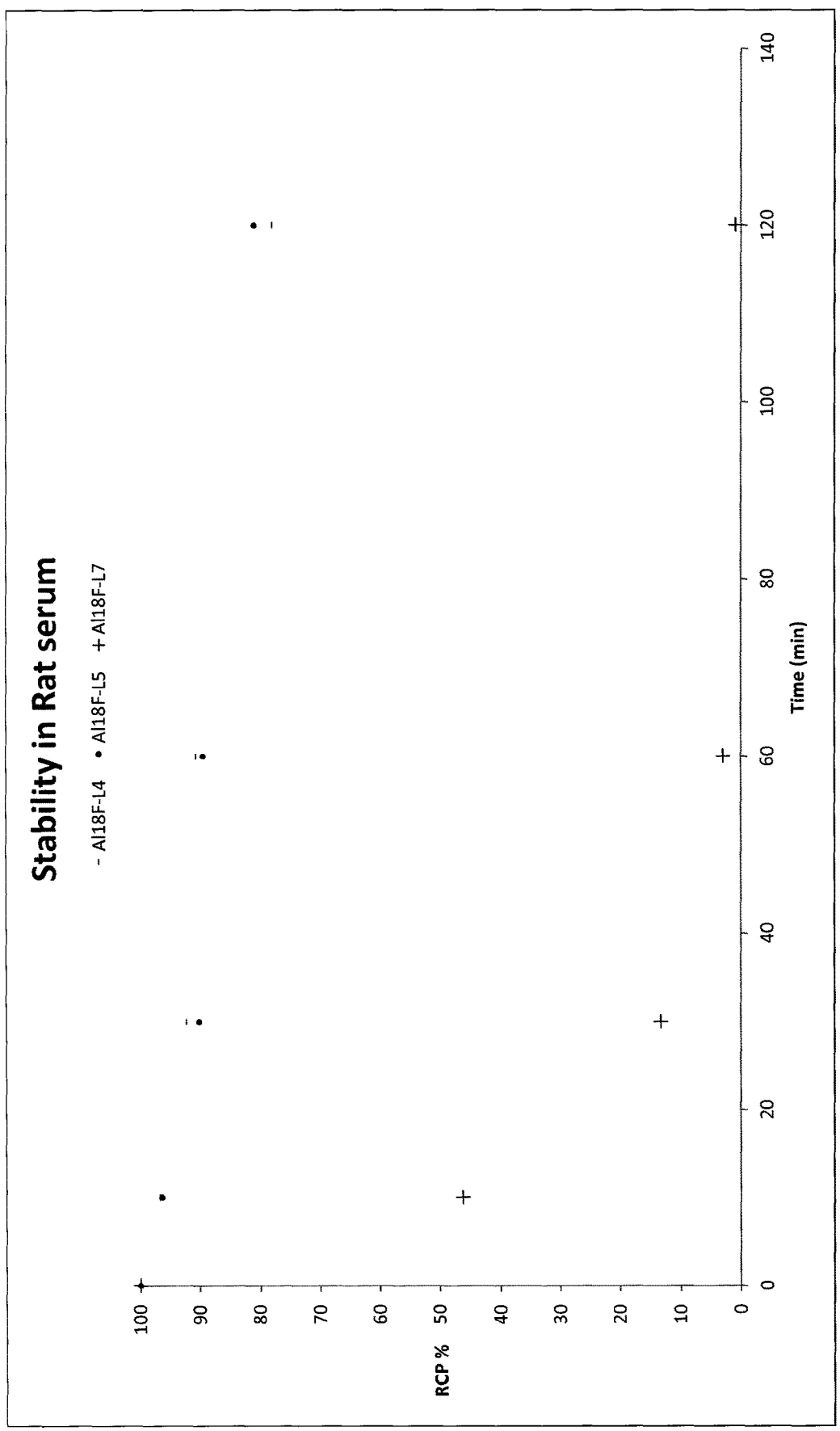
Figure 11:
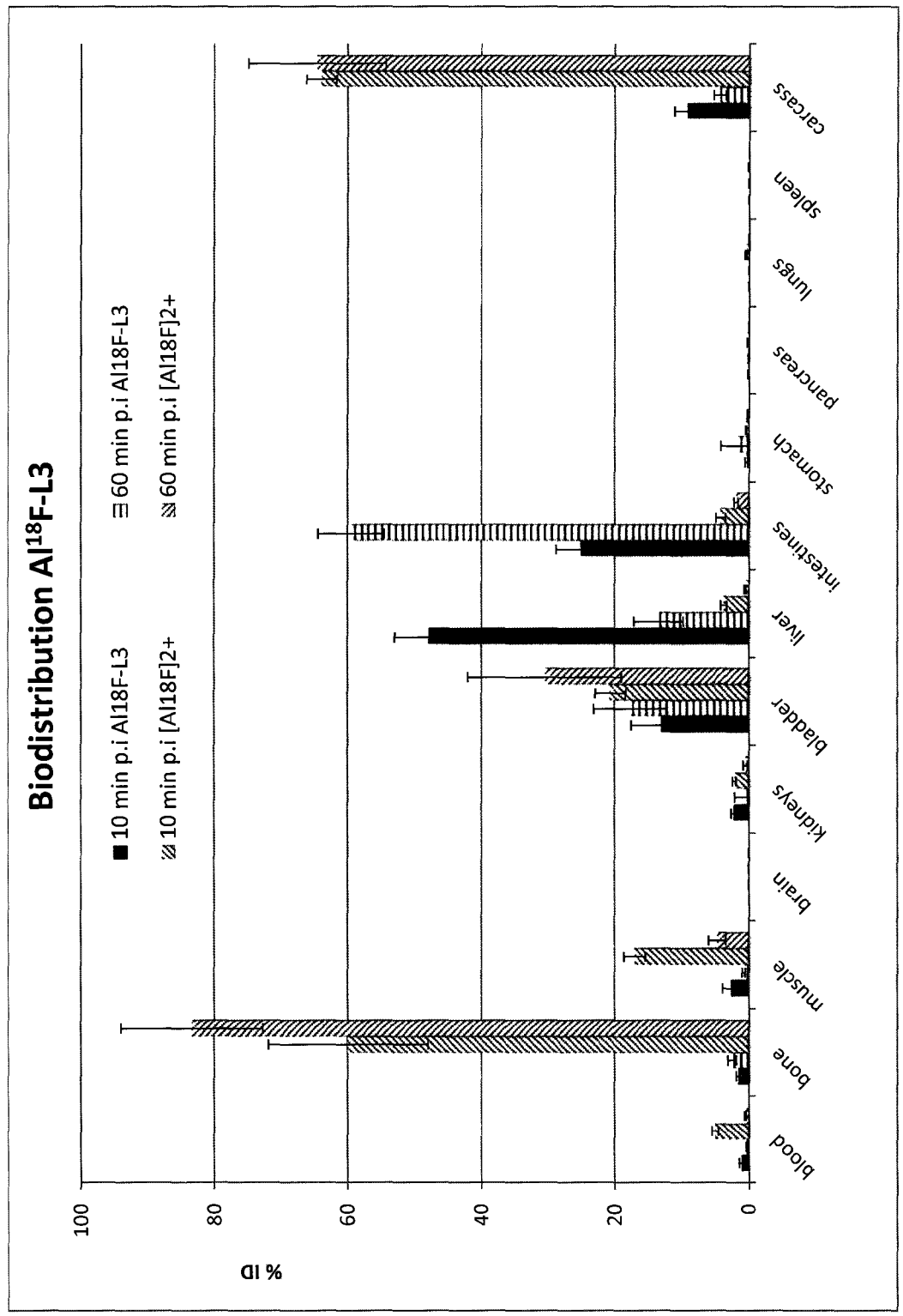
FIG. 11. provides a graphic that shows the results of biodistribution of {Al$^{18}$F}$^2$ and Al$^{18}$F-L3 after IV injection in mice at 10 minutes and 60 minutes p.i. In Y-axis, values represent % of injected dose (ID) and error bars represent SD while X-axis displays the organs studied FIG. 12. is a graphic that shows the HPLC-HRMS of Al$^{19}$F-L26 (a) BPC; (b) Extracted ion chromatogram (ESI C$_{19}$H$_{24}$AlN$_2$O$_7$+0.05); (c) Extracted ion chromatogram (ESI C$_{19}$H$_{23}$AlFN$_2$O$_6$±0.05) and (d) spectrum view corresponding to peak Rt 4.2-4.4 min.
Figure 12:
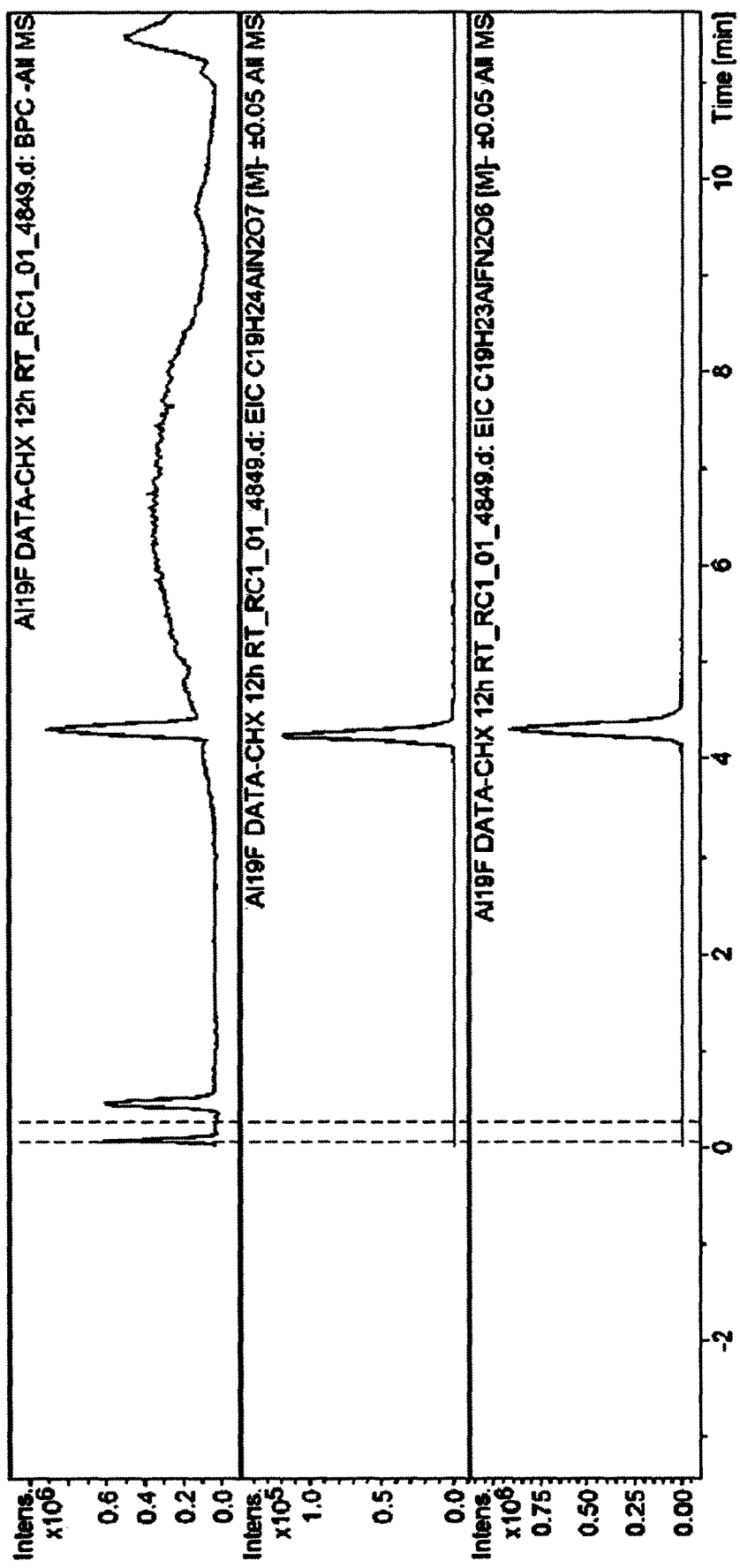
Figure 12:
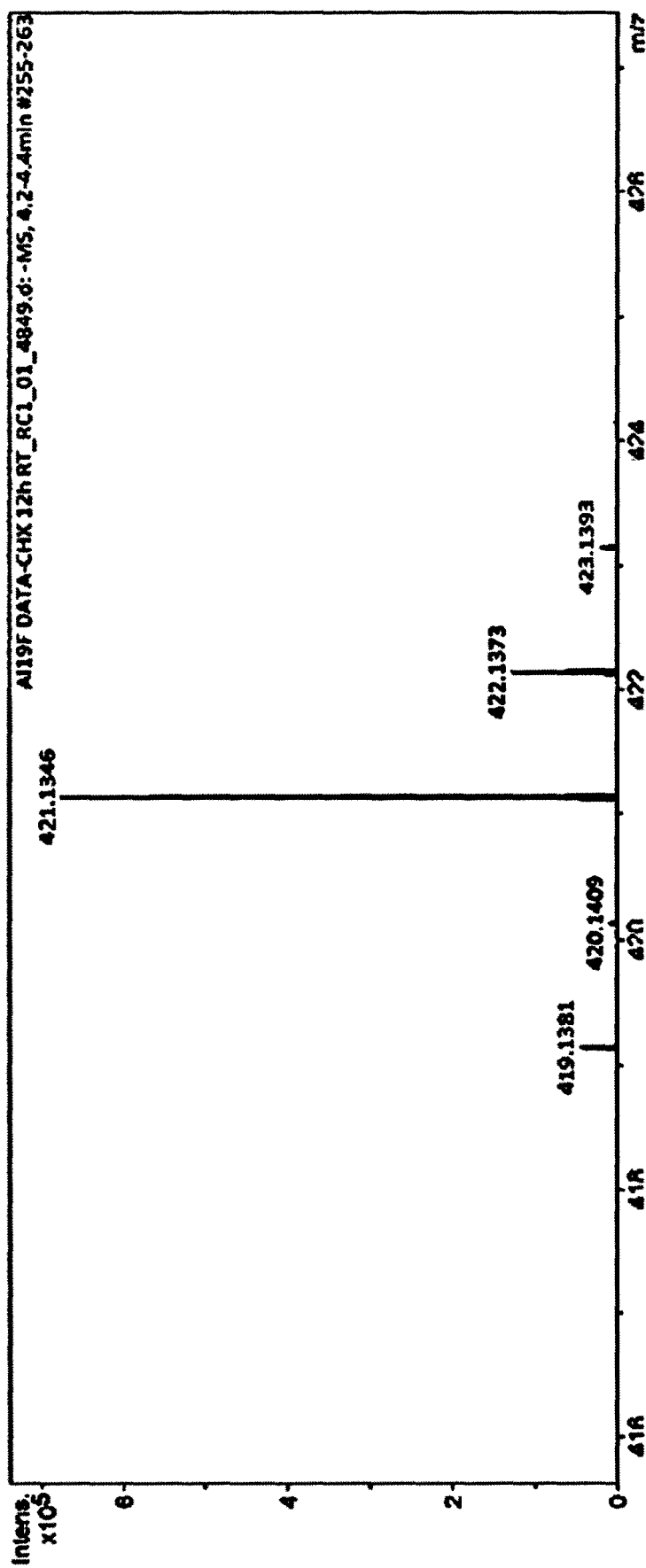
Figure 13:
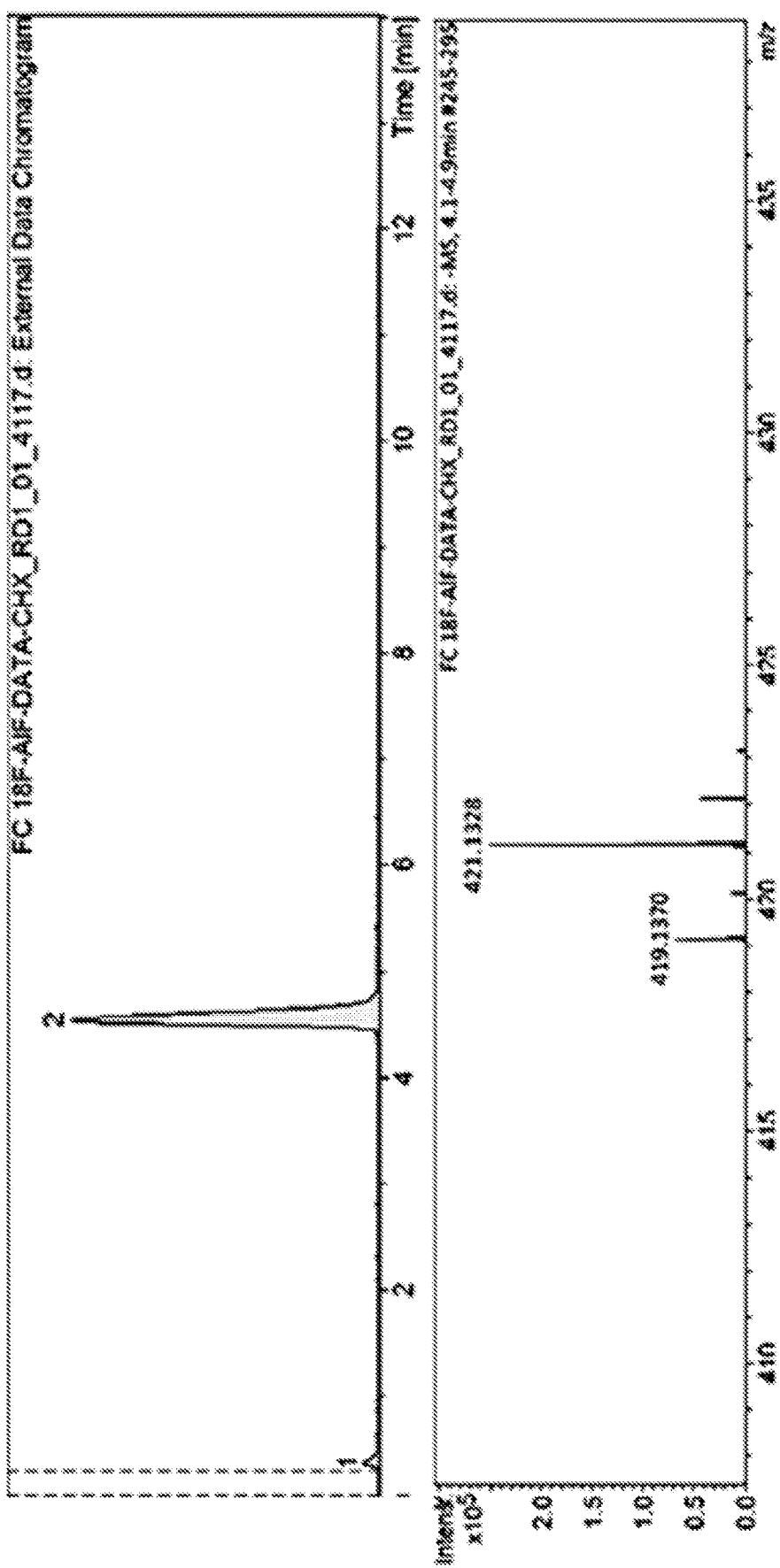
FIG. 13. is a graphic that shows the radio-HPLC-HRMS of Al$^{18}$F-L26 after purification (a) Radiometric channel; (b) spectrum view corresponding to peak Rt 4.1-4.9 min.
Figure 14:
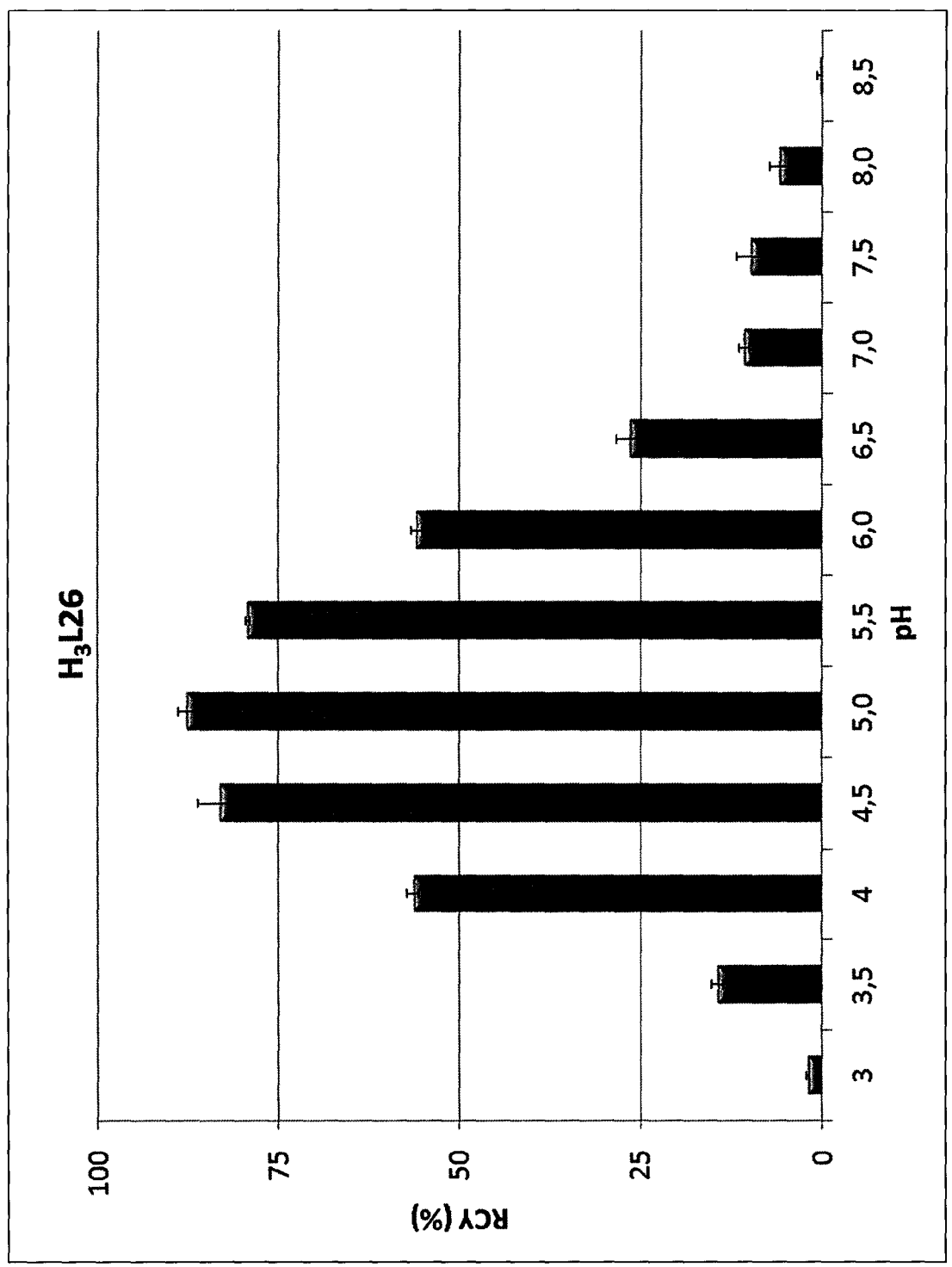
FIG. 14. provides in a graphic the radiochemical yields of the {Al$^{18}$F}-complexation with H$_3$L26 at different pH. X-axis displays the pH of the reaction medium, while the Y-axis displays the radiochemical yield in percent.
Figure 15:
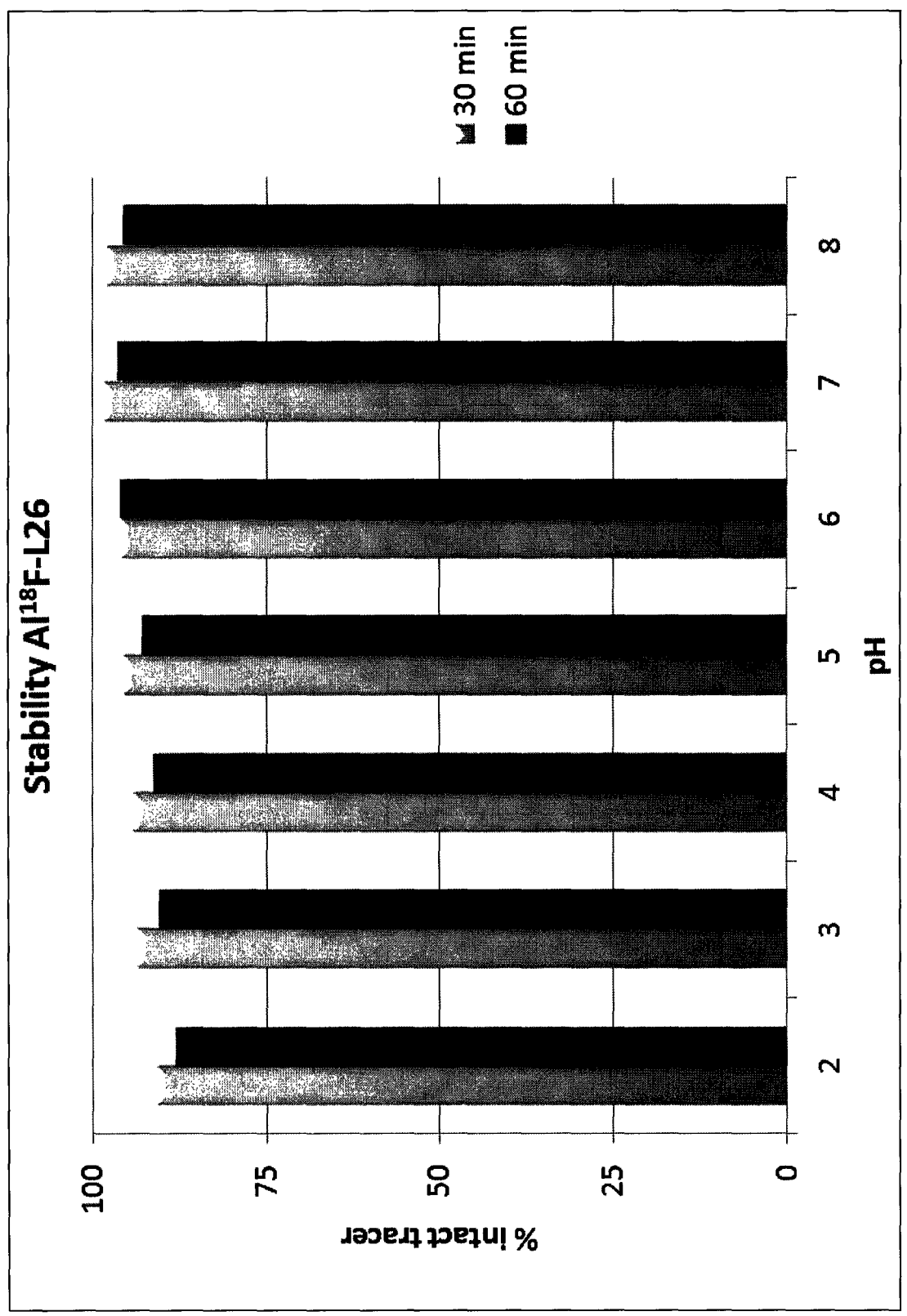
FIG. 15. provides a graph that shows the stability results of Al$^{18}$F-L26 at different pH.
Figure 16:
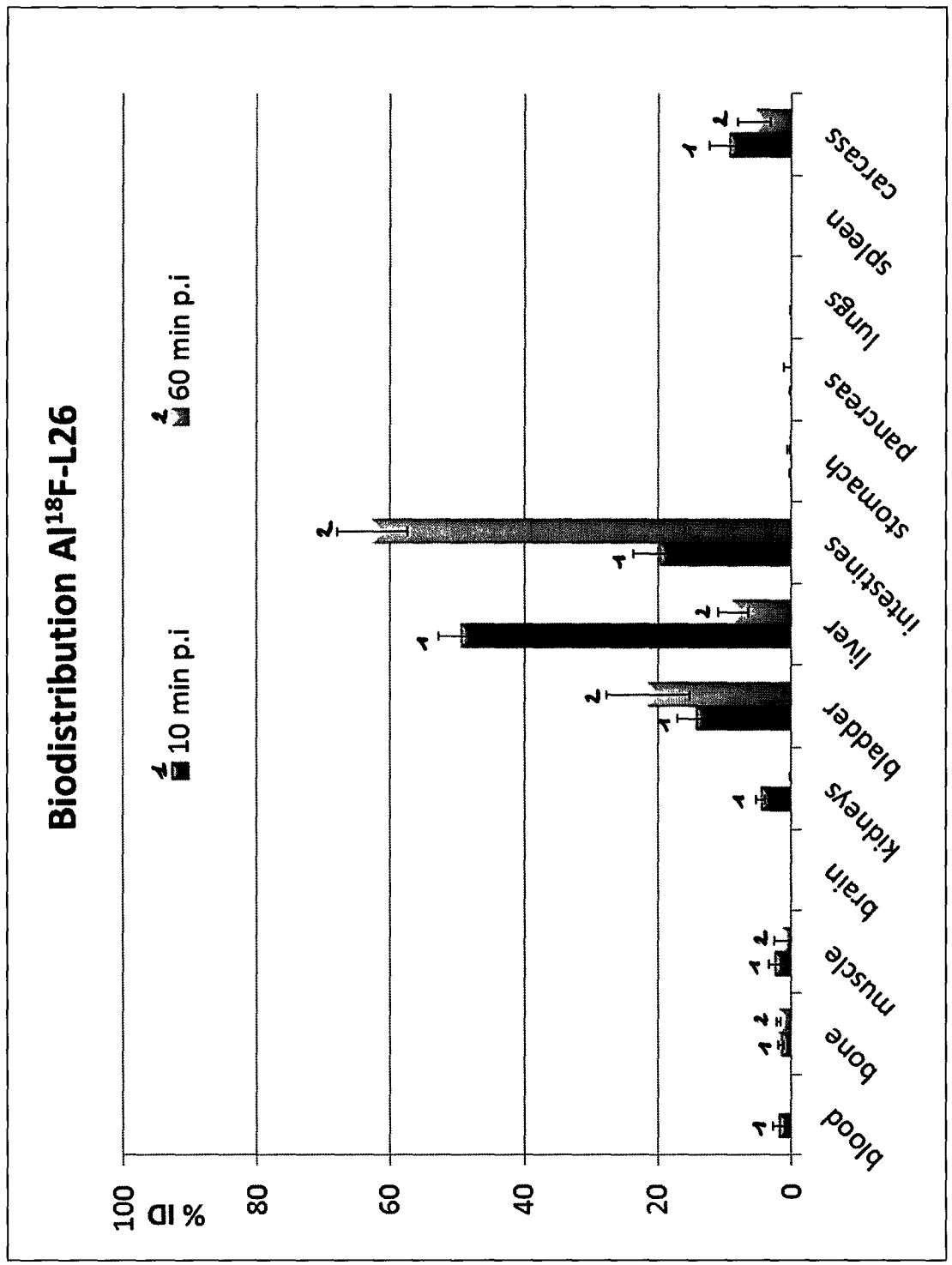
FIG. 16. provides a graphic that shows the results of biodistribution of {Al$^{18}$F}$^{2+}$ and Al$^{18}$F-L26 after IV injection in mice at 10 minutes and 60 minutes p.i. In Y-axis, values represent % of injected dose (ID) and error bars represent SD while X-axis displays the organs studied.
Figure 17:
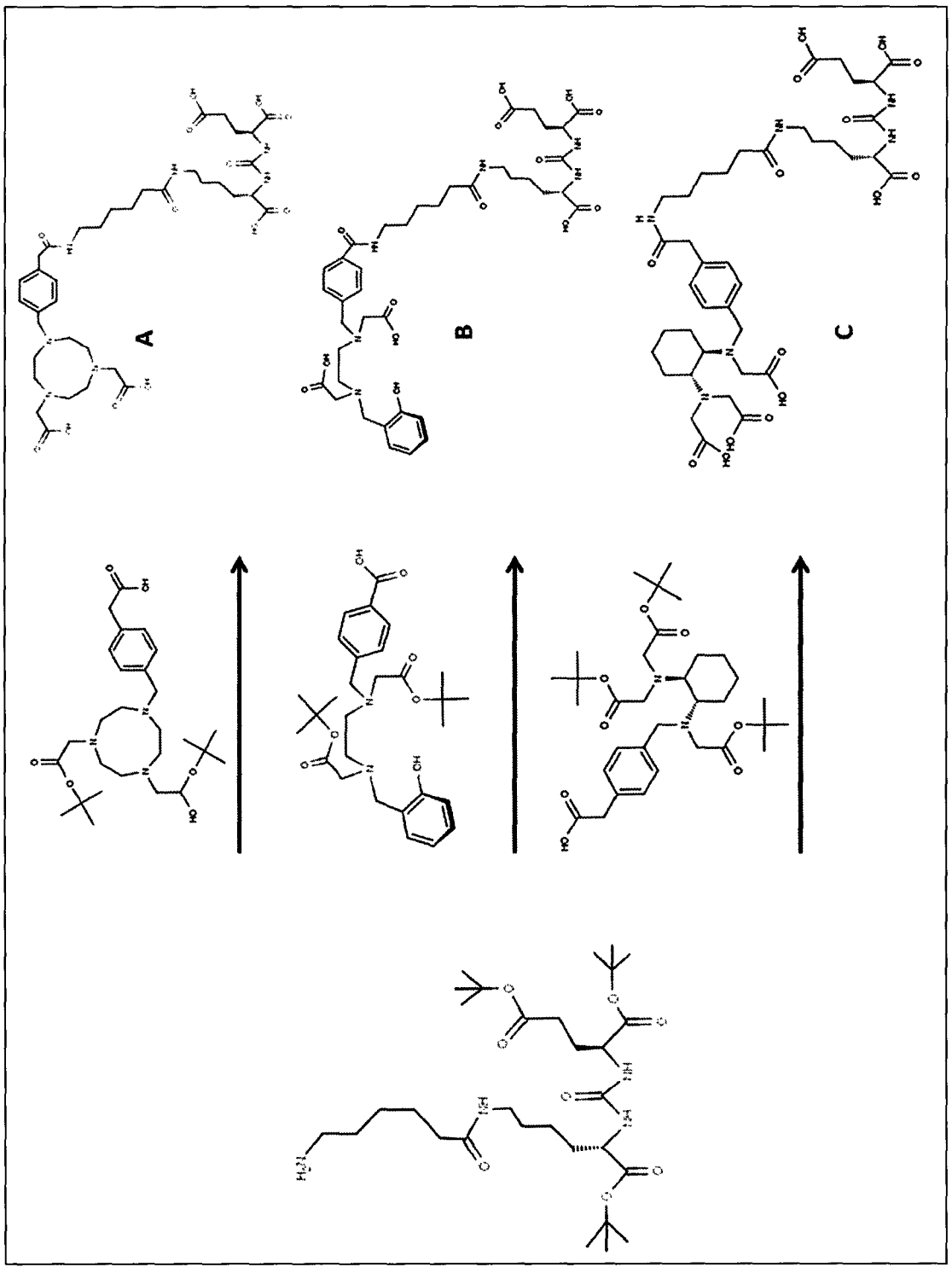
FIG. 17. synthesis of (A) NODA-MPAA-PSMA, (B) H$_3$L6-PSMA and (C) H$_3$L27-MPAA-PSMA FIG. 18. provides a graphic that shows the results of biodistribution (% ID) of $^{68}$Ga-HBED-CC-PSMA with or without coadministration of 2 mg/kg 2-PMPA at 10 min or 60 min p.i. In Y-axis, values represent % of injected dose (ID) and error bars represent SD while X-axis displays the organs studied.
Figure 18:
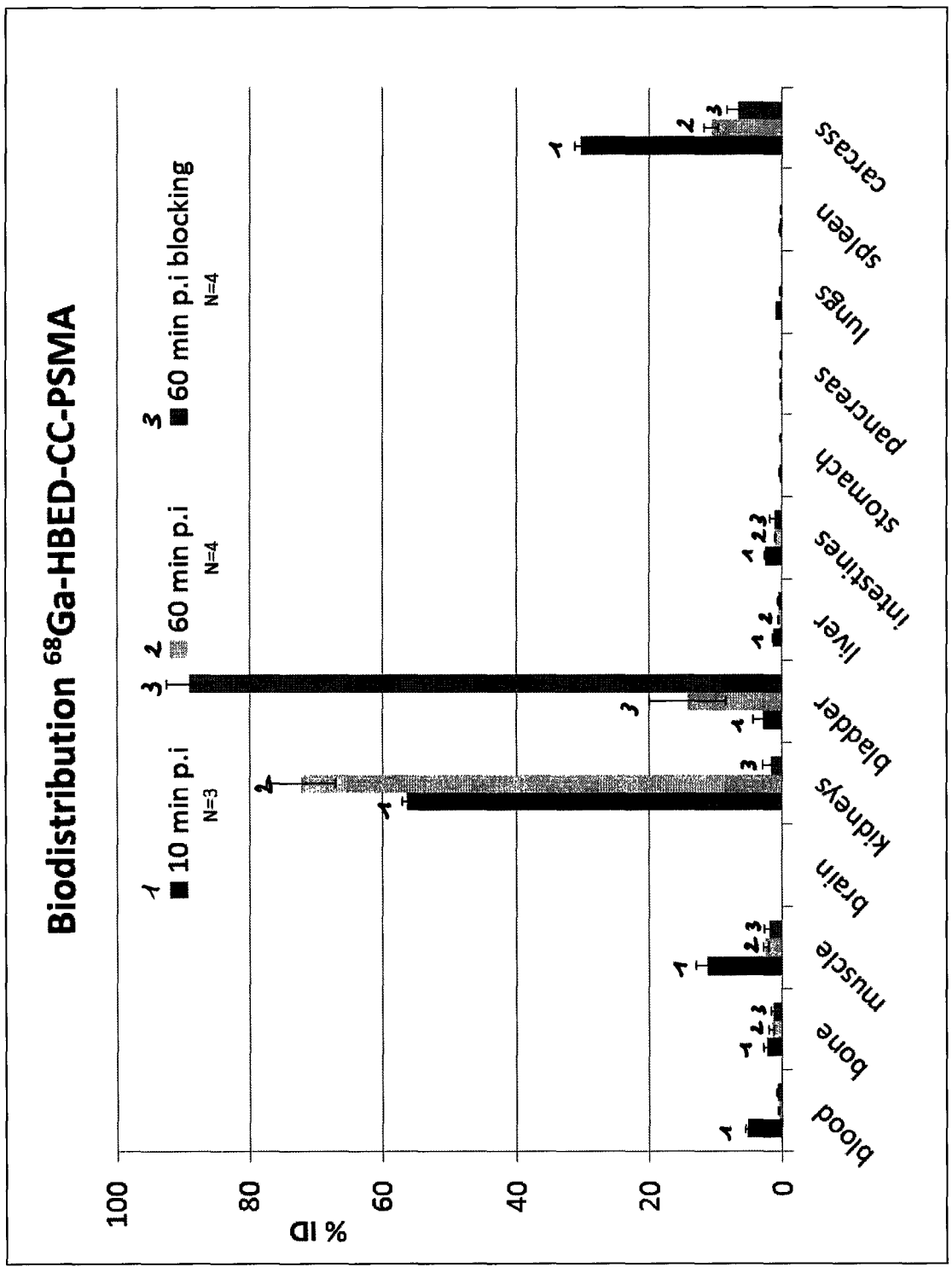
Figure 19:
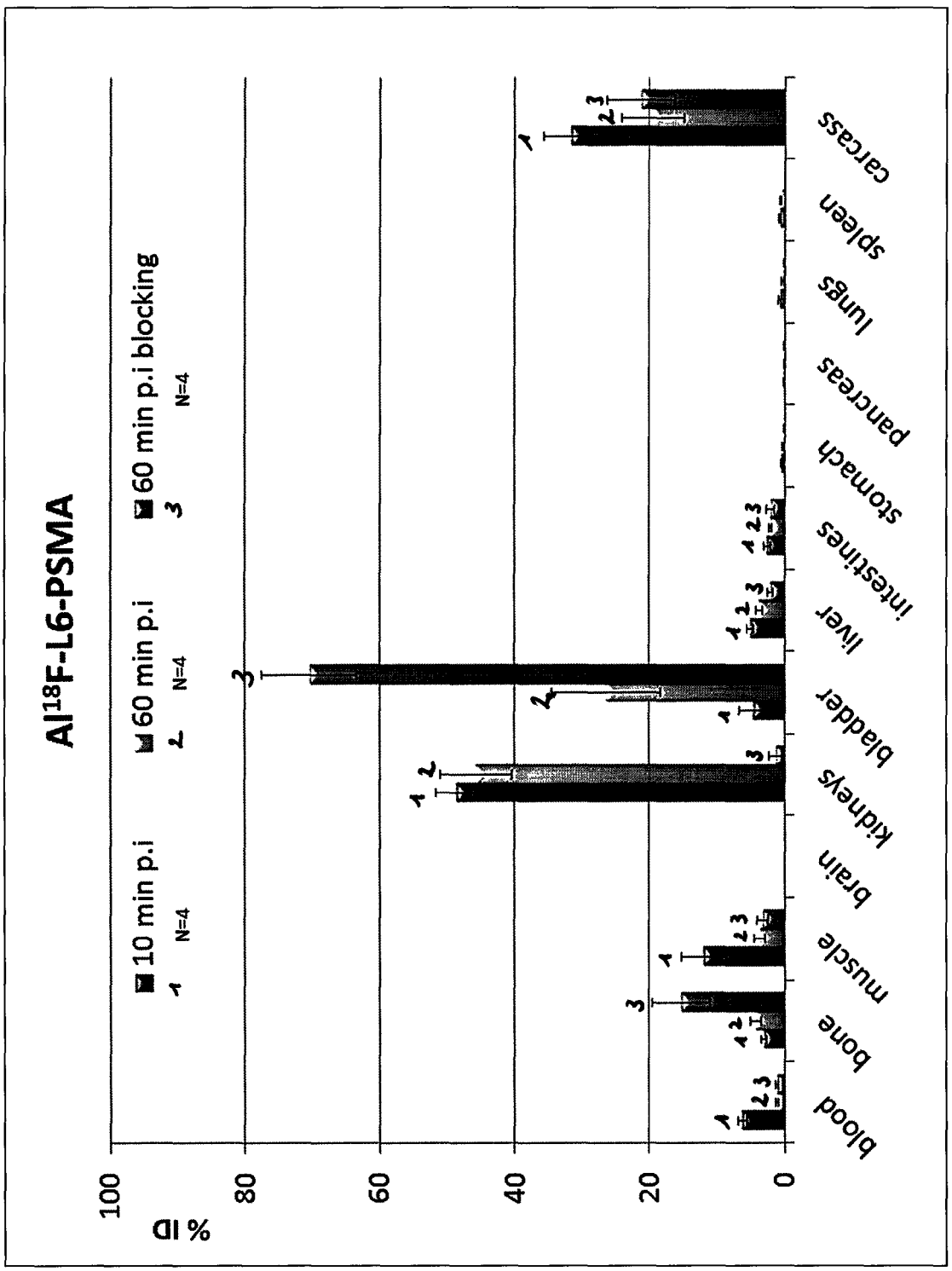
FIG. 19. provides a graphic that shows the results of biodistribution (% ID) of Al$^{18}$F-L6-PSMA with or without coadministration of 2 mg/kg 2-PMPA at 10 min or 60 min p.i. In Y-axis, values represent % of injected dose (ID) and error bars represent SD while X-axis displays the organs studied.
Figure 20:
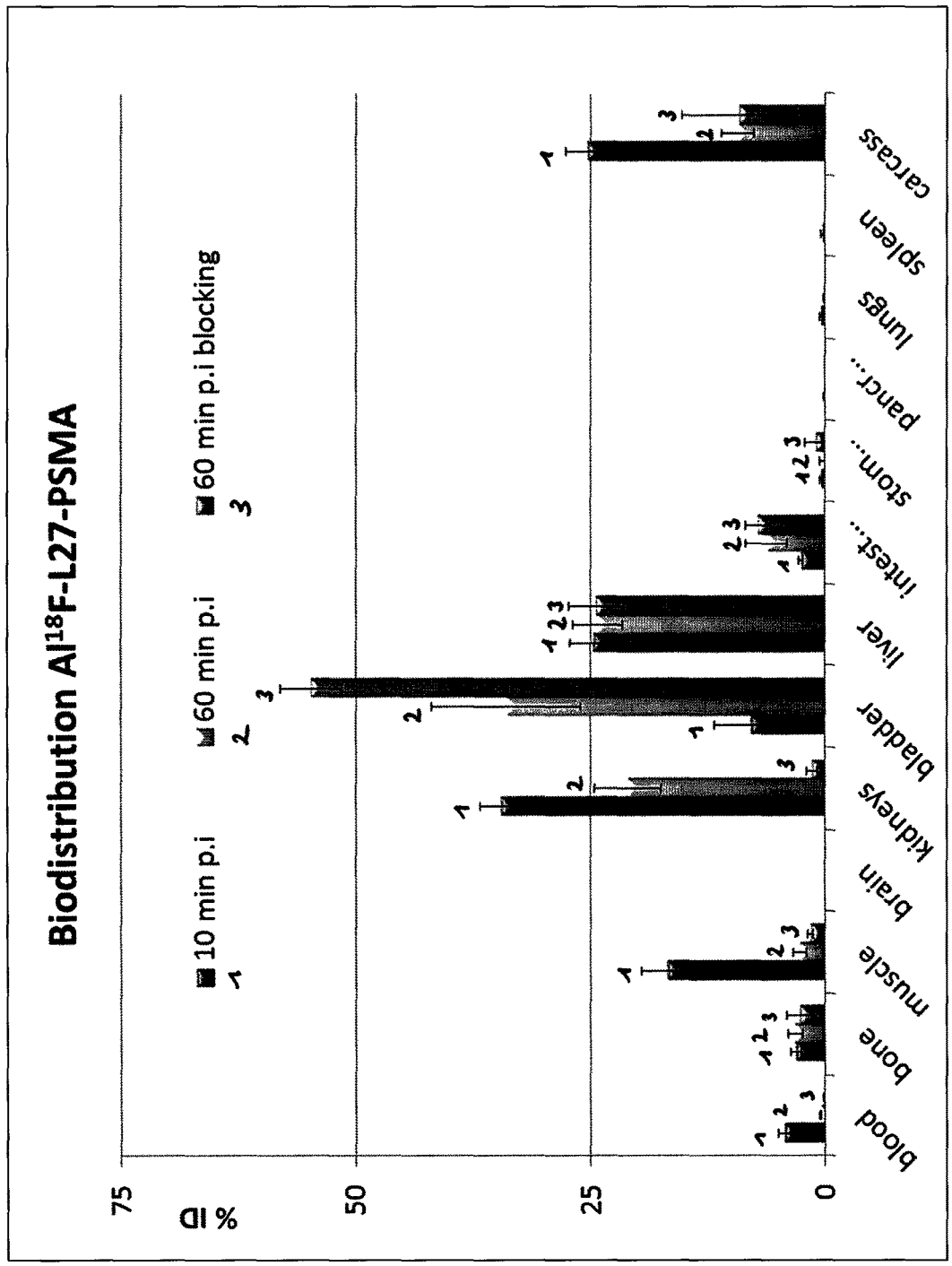
FIG. 20. provides a graphic that shows the results of biodistribution (% ID) of Al$^{18}$F-L27-MPAA-PSMA with or without coadministration of 2 mg/kg 2-PMPA at 10 min or 60 min p.i. In Y-axis, values represent % of injected dose (ID) and error bars represent SD while X-axis displays the organs studied.
Figure 21:
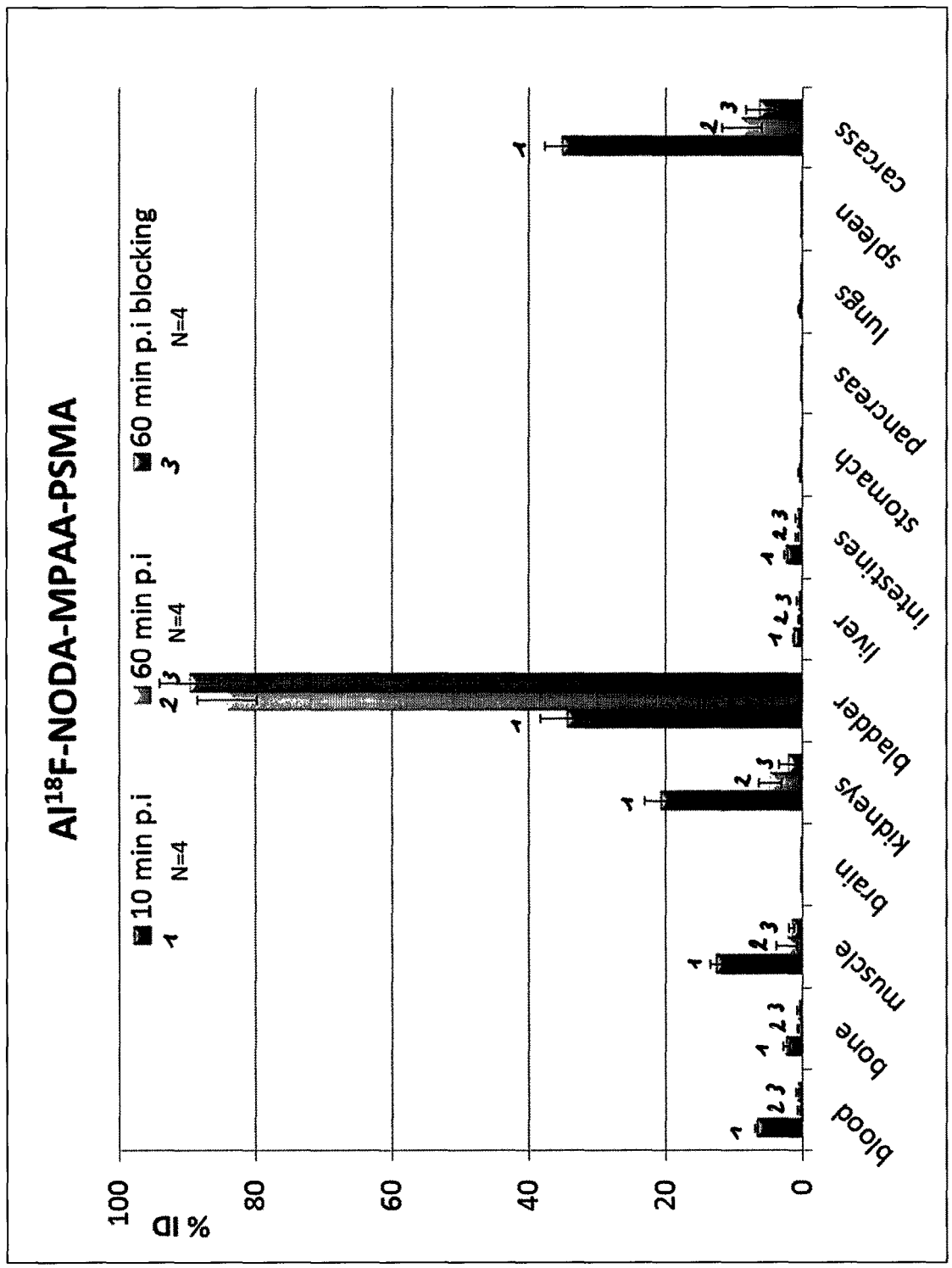
FIG. 21. provides a graphic that shows the results of biodistribution (% ID) of Al$^{18}$F-NODA-MPAA-PSMA with or without coadministration of 2 mg/kg 2-PMPA at 10 min or 60 min p.i. In Y-axis, values represent % of injected dose (ID) and error bars represent SD while X-axis displays the organs studied.
Figure 22:
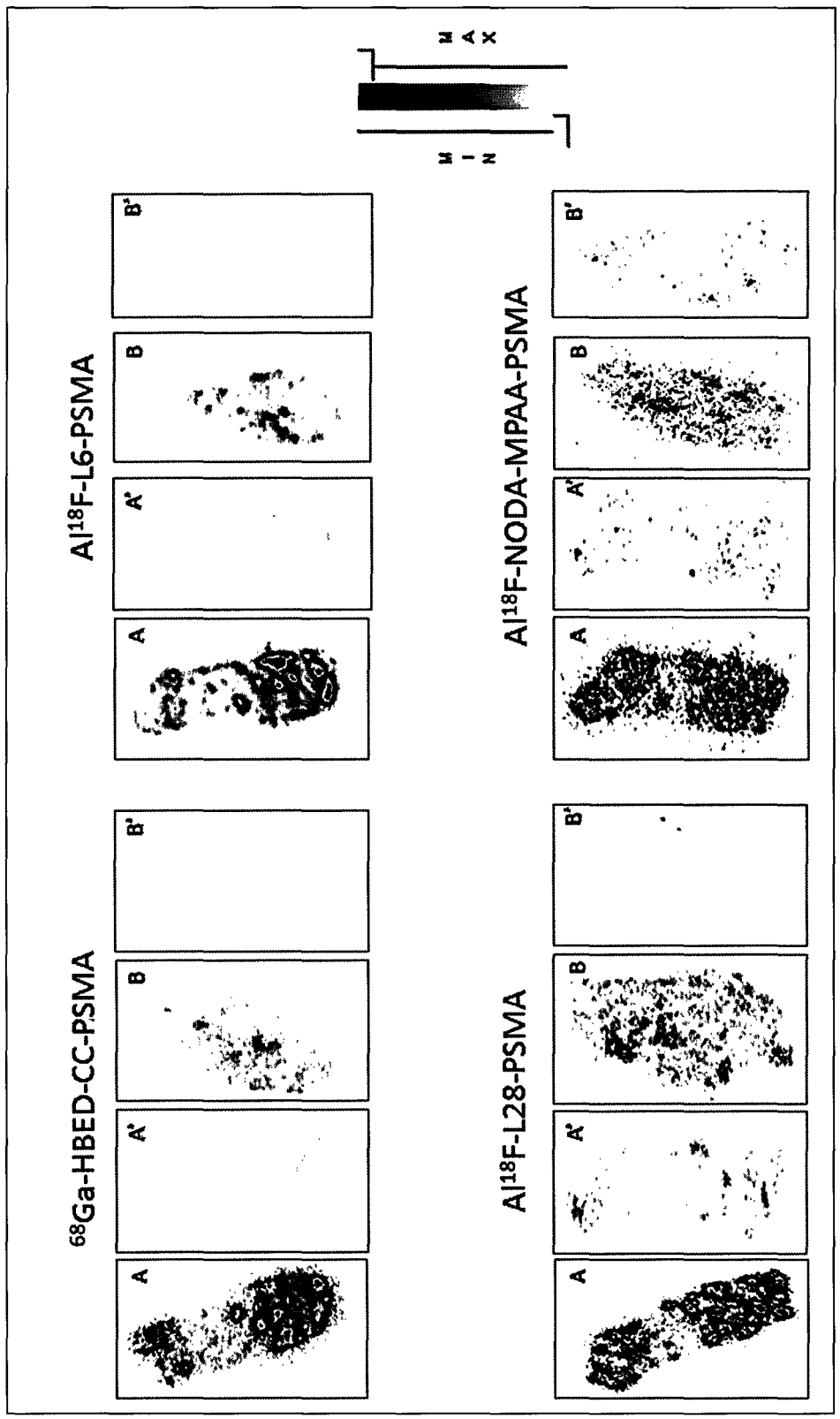
FIG. 22. In vitro autoradiography on (A) human prostate tumor tissue and (B) healthy human prostate tissue with $^{68}$Ga-HBED-CC-PSMA, Al$^{18}$F-L6-PSMA, Al$^{18}$F-L27-PSMA and Al$^{18}$F-NODA-MPAA-PSMA with (') or without blocking with 2-PMPA (100 μM)
Figure 23:
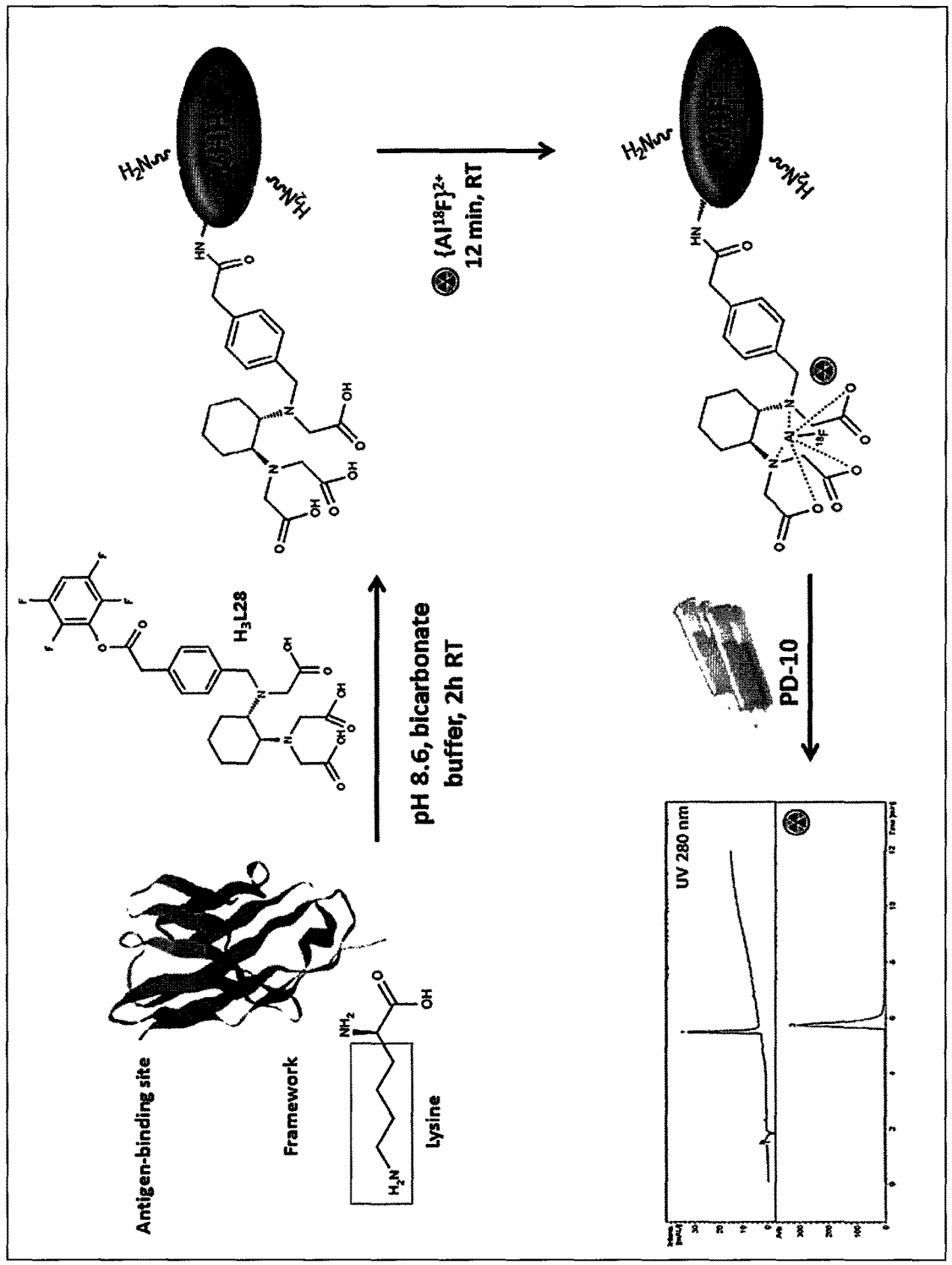
FIG. 23. provides a schematic overview of the nanobody-labelling procedure via the Al$^{18}$F-method FIG. 24. provides in a graphic the radiochemical yields of the {Al$^{18}$F}-complexation with H$_3$L26, H$_3$L29, H$_3$L30, H$_3$L31 and H$_3$L32 at different temperatures. X-axis displays the reaction temperature, while the Y-axis displays the radiochemical yield in percent.
Figure 24:
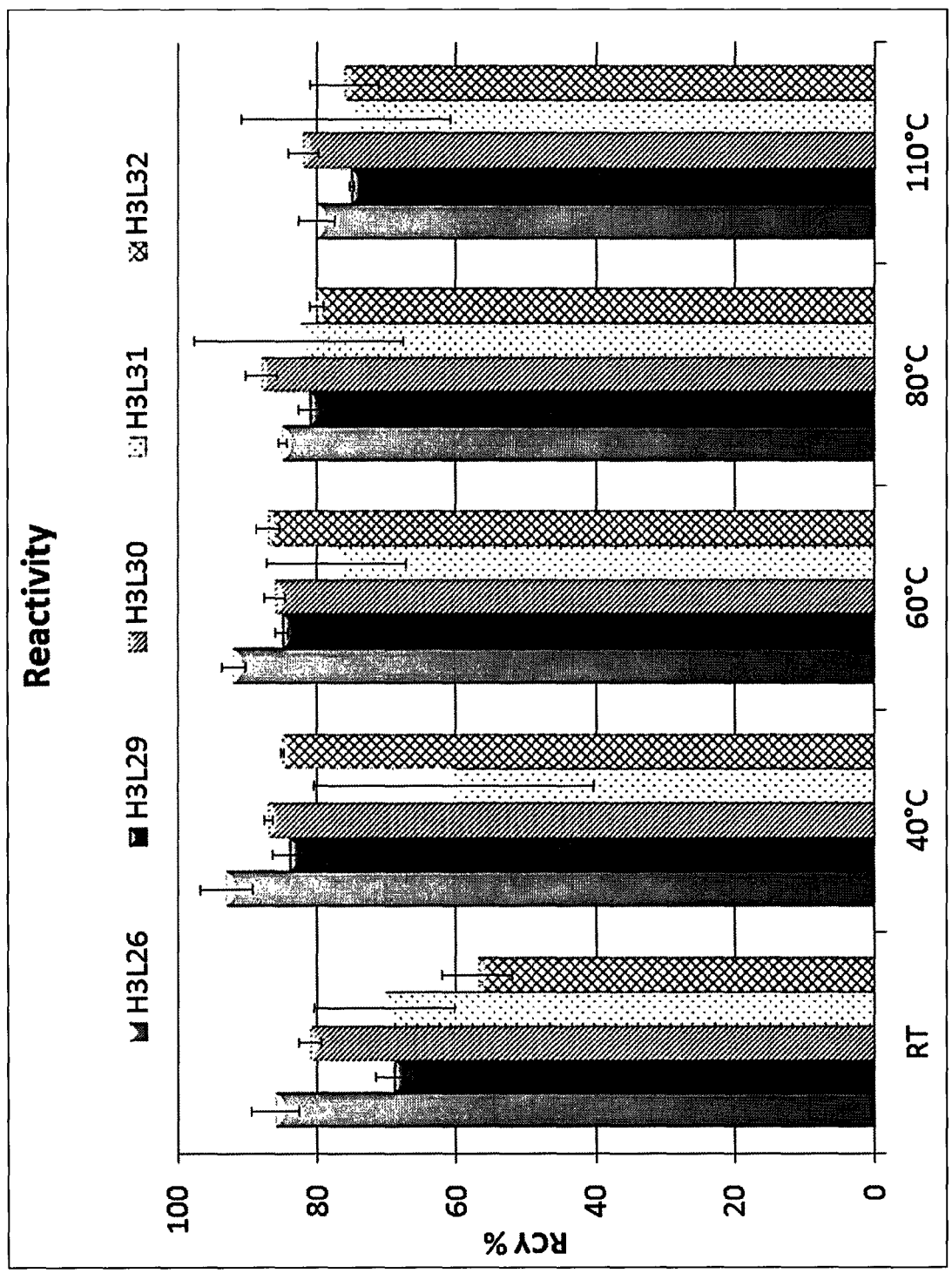
Figure 25:
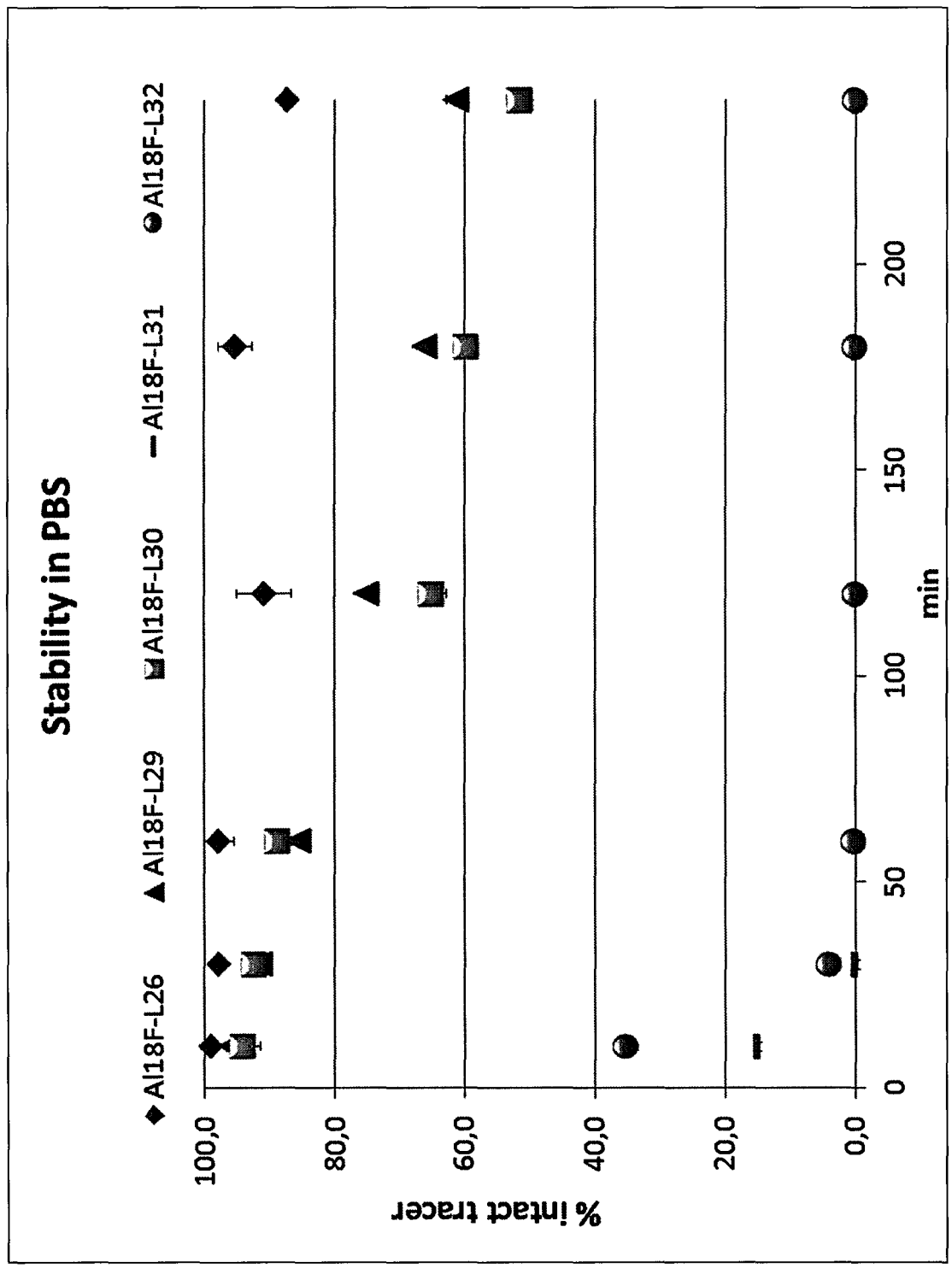
FIG. 25. provides a graphic that shows the stability results of the aluminum fluoride complexes Al$^{18}$F-L26, Al$^{18}$F-L29, Al$^{18}$F-L30, Al$^{18}$F-L31 and Al$^{18}$F-L32 in PBS over time. The percentage intact tracer is represented as a function of time.
Figure 26:
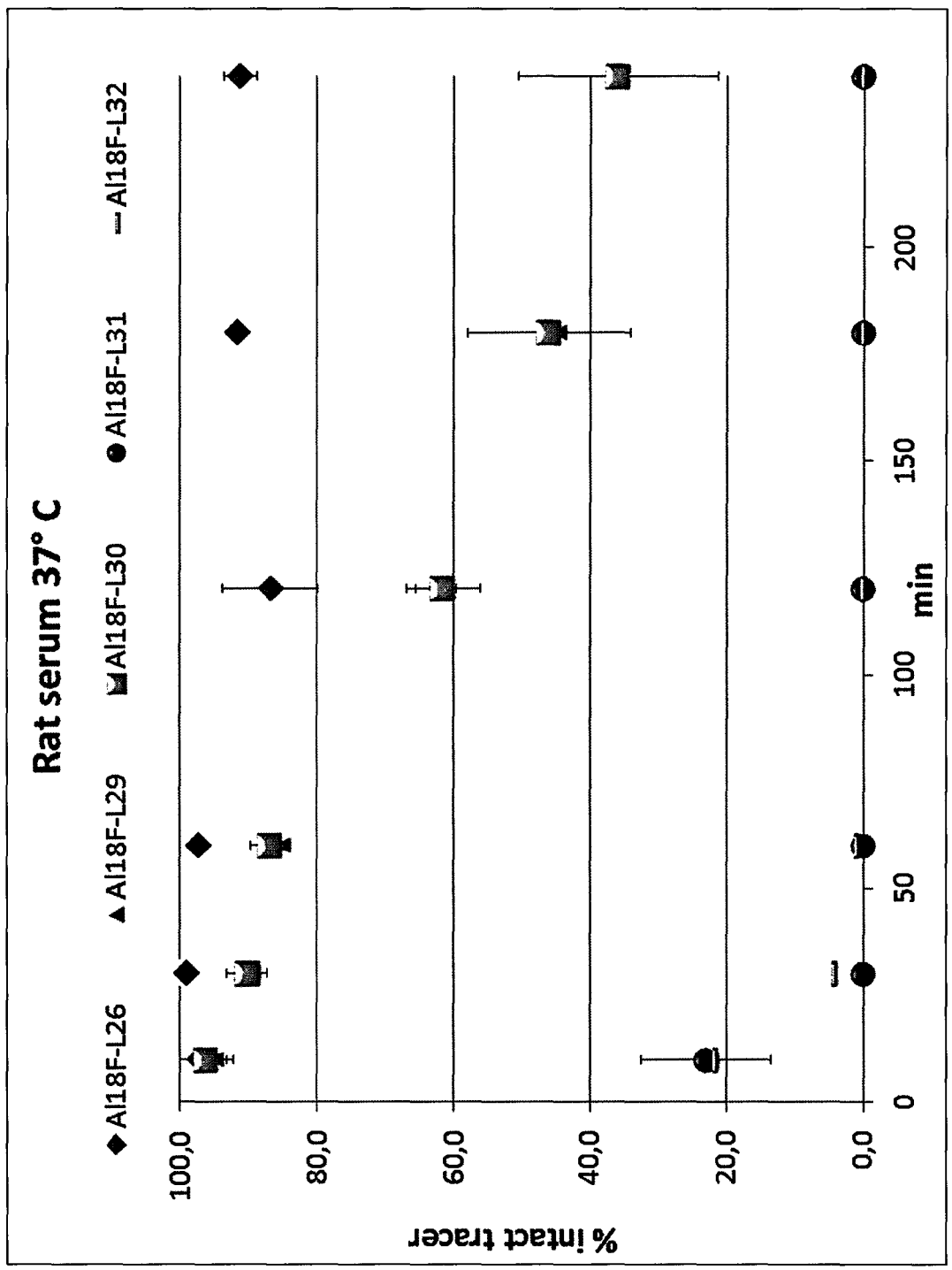
FIG. 26. provides a graphic that shows the percentage intact tracer of the aluminum fluoride complexes Al$^{18}$F-L26, Al$^{18}$F-L29, Al$^{18}$F-L30, Al$^{18}$F-L31 and Al$^{18}$F-L32 in rat serum over time. The percentage intact tracer is represented as a function of time.
Figure 27:
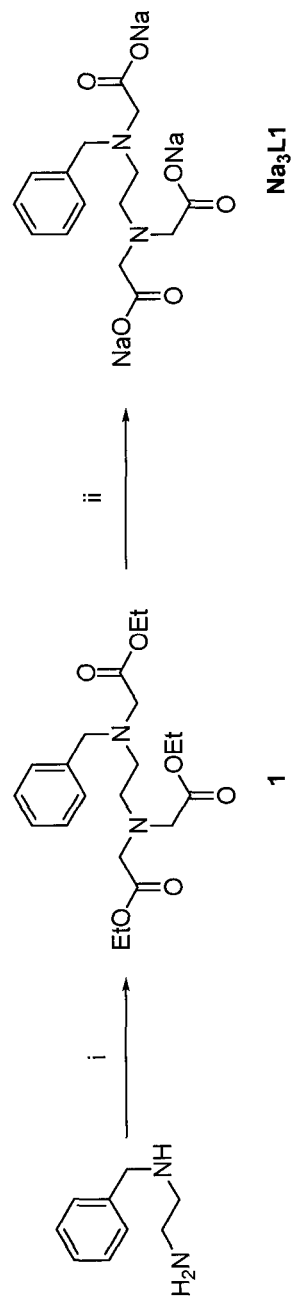
FIG. 27 displays synthesis Schemes 1-23.
Figure 27:
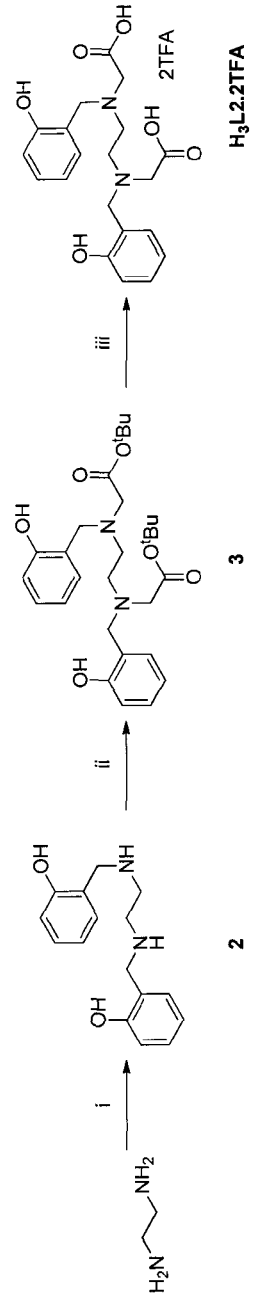
Figure 27:
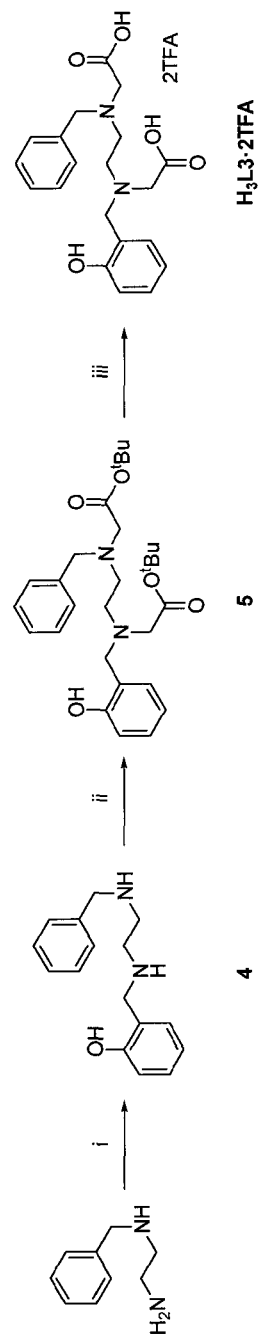
Figure 27:
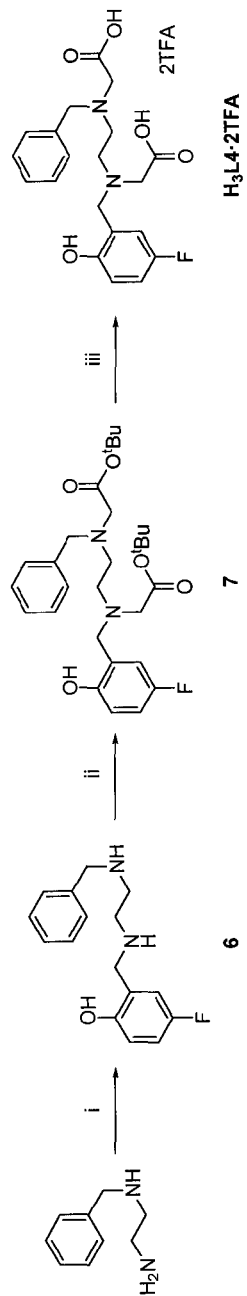
Figure 27:
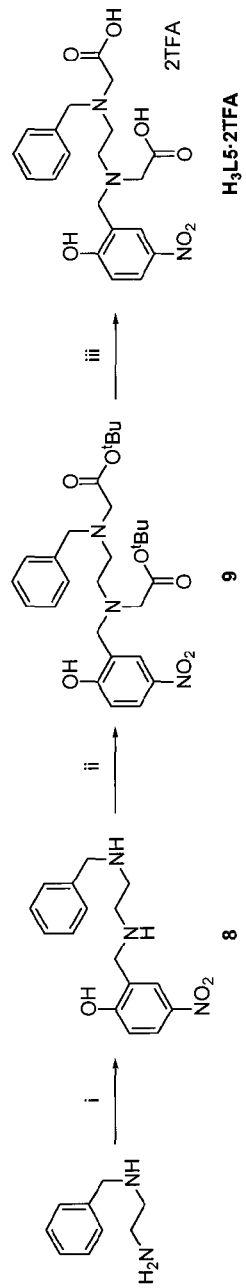
Figure 27:
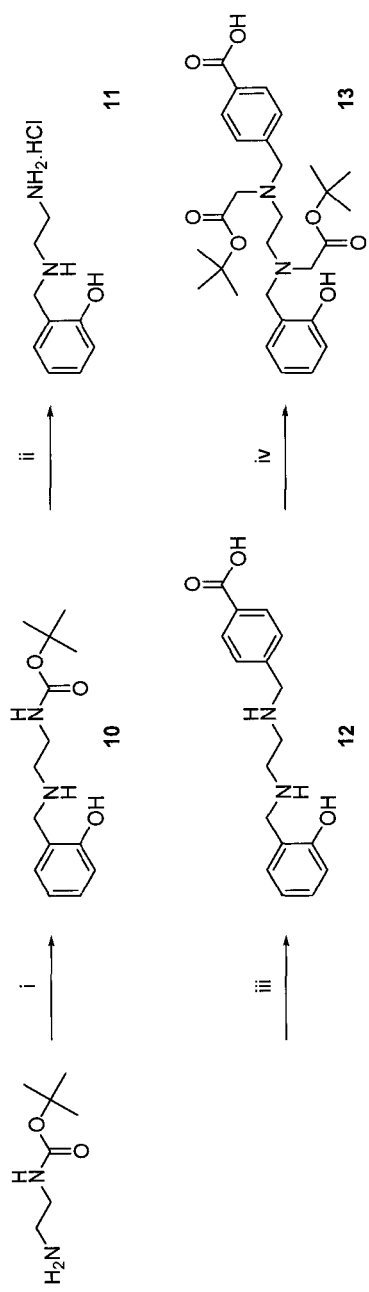
Figure 27:
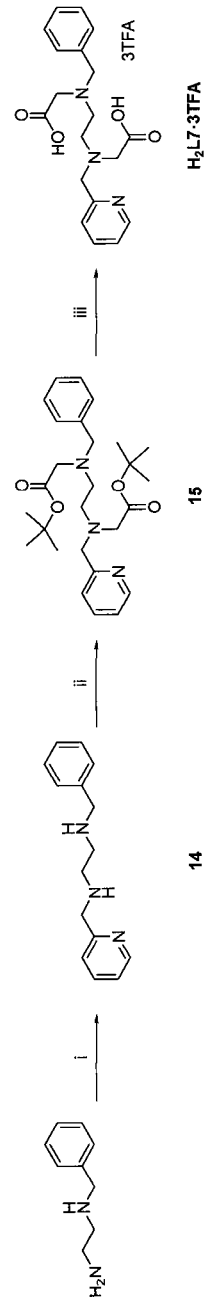
Figure 27:
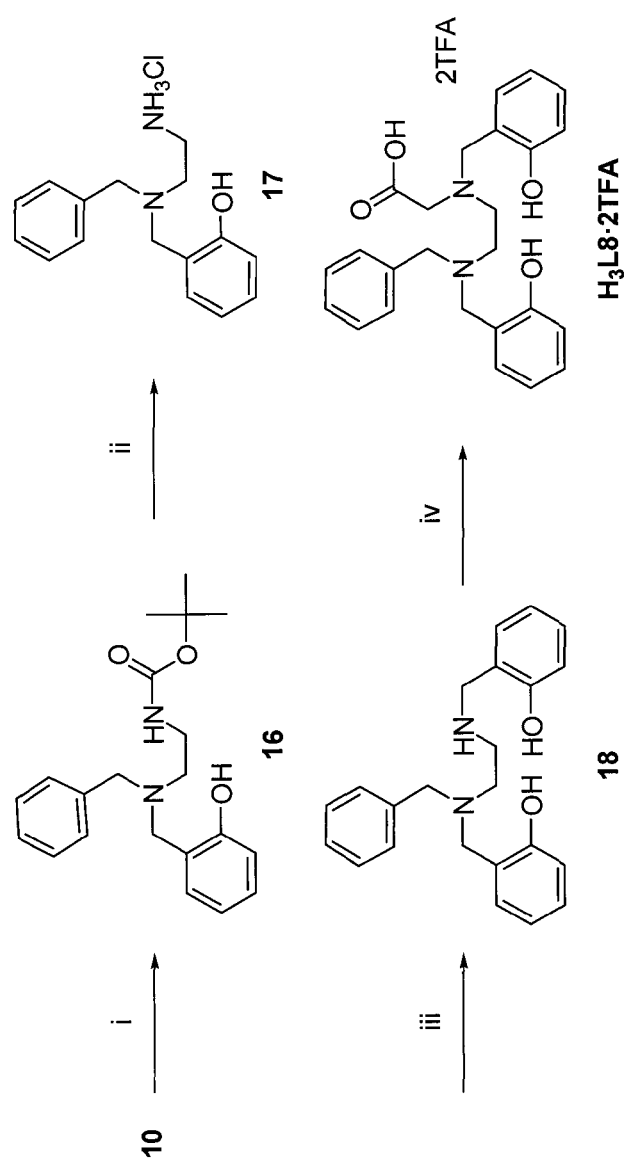
Figure 27:
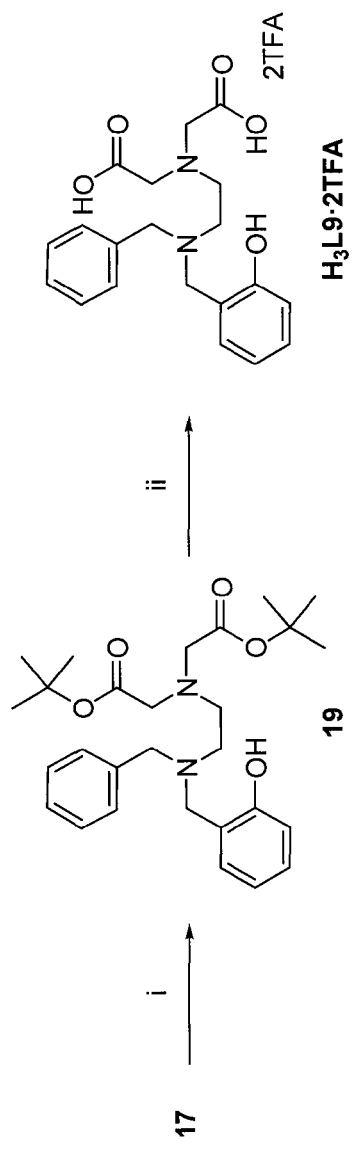
Figure 27:
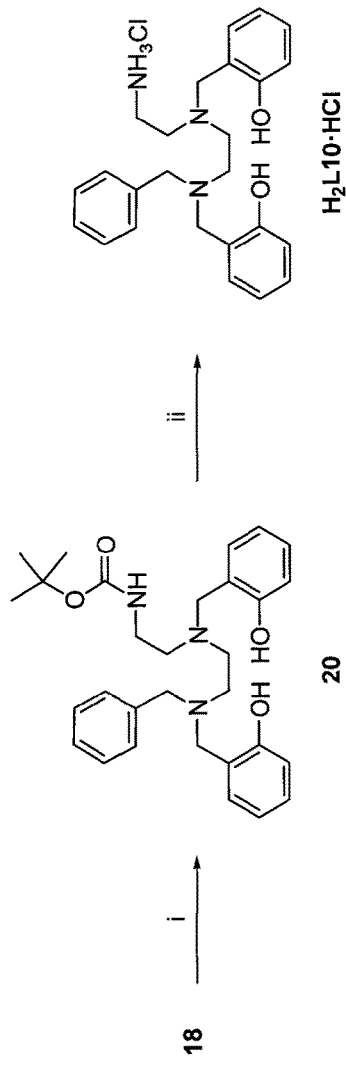
Figure 27:
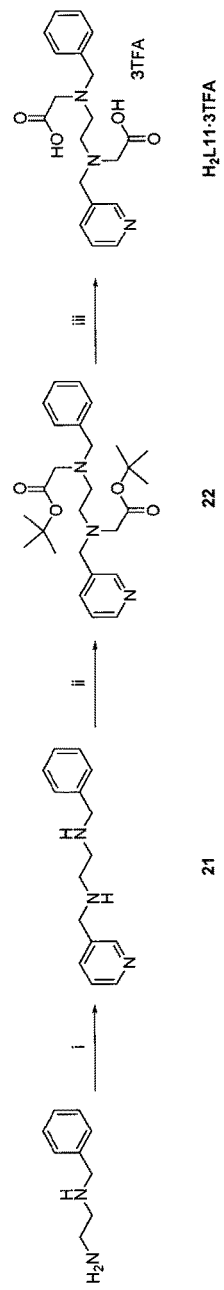
Figure 27:
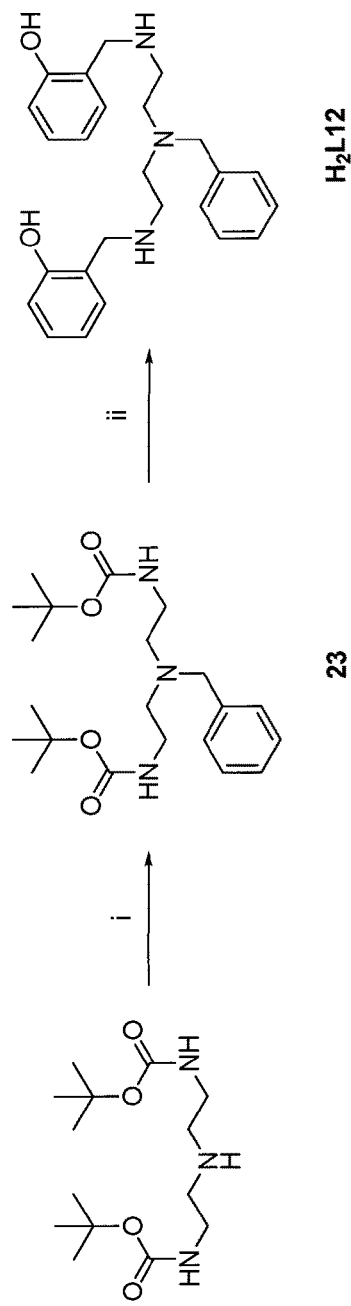
Figure 27:
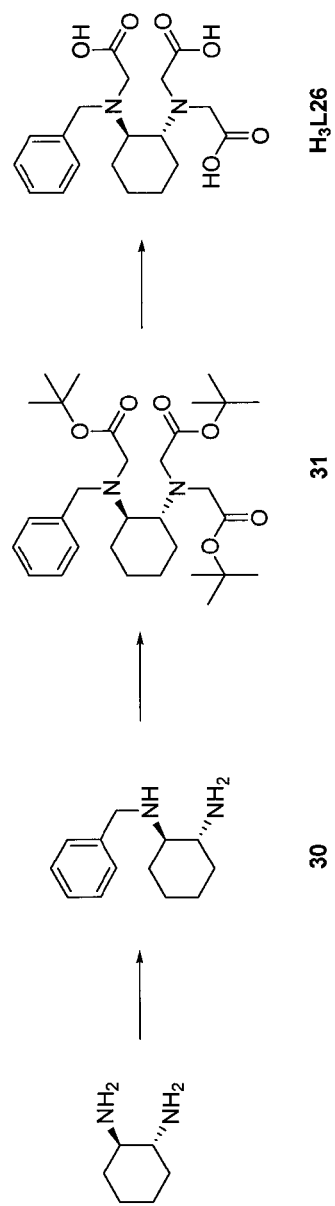
Figure 27:
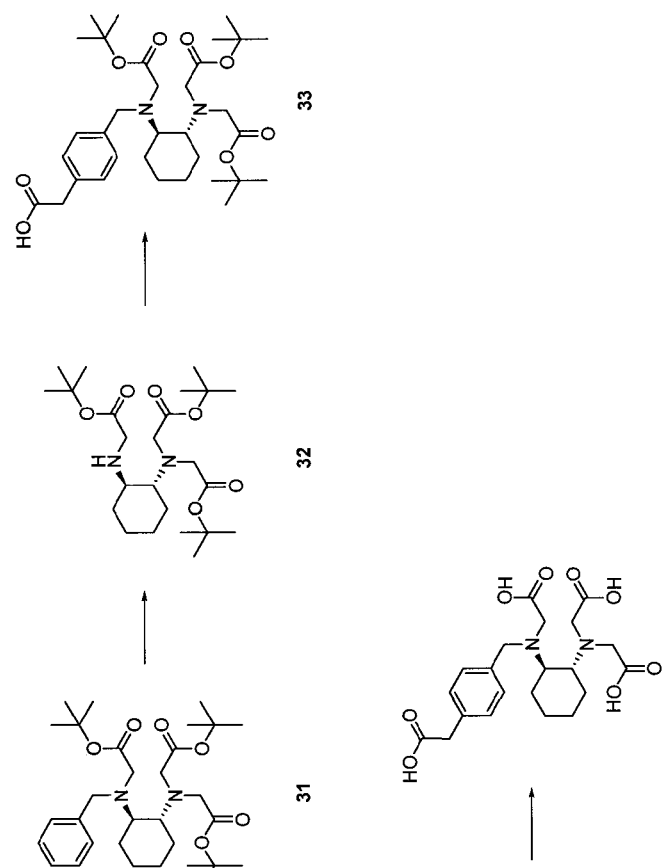
Figure 27:
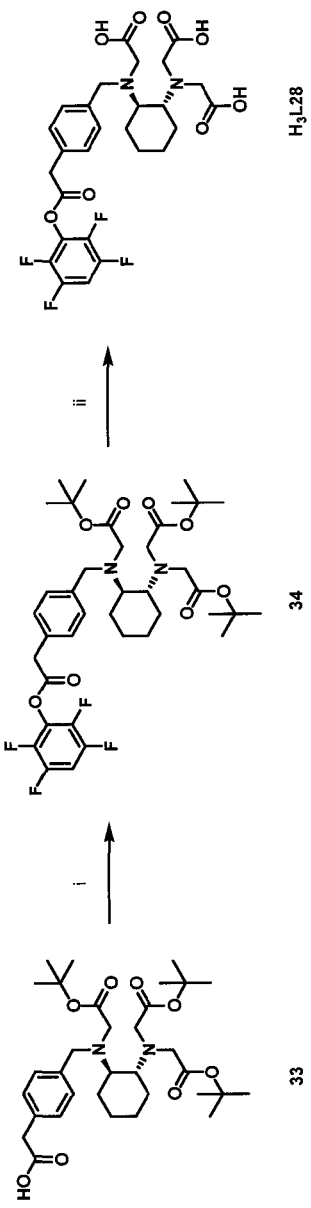
Figure 27:
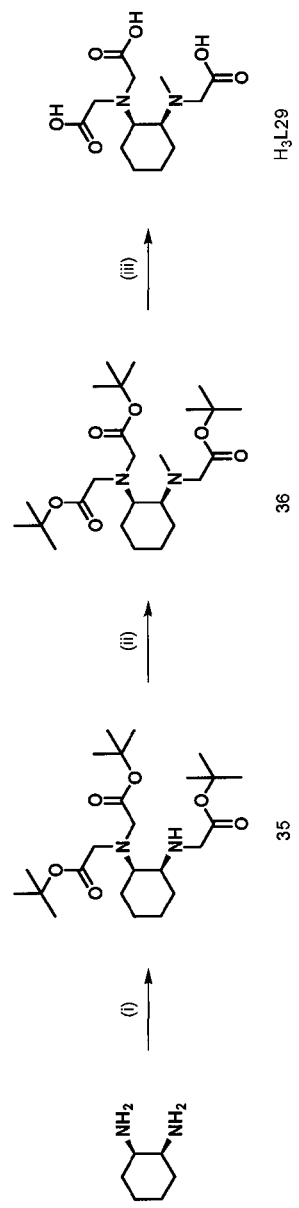
Figure 27:
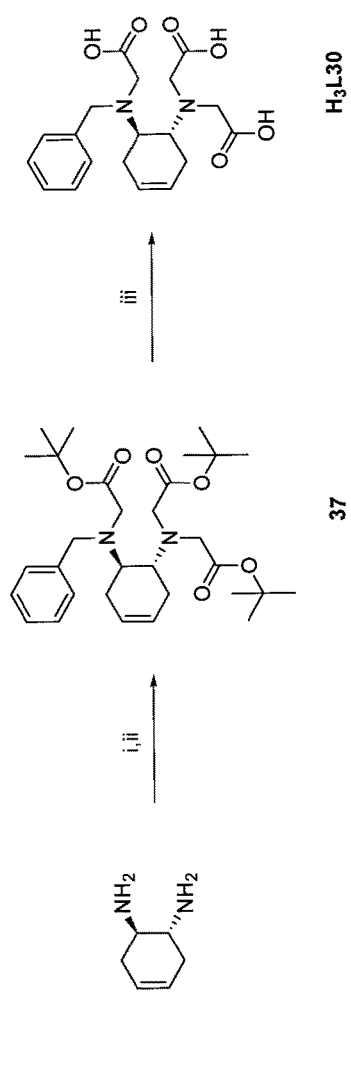
Figure 27:
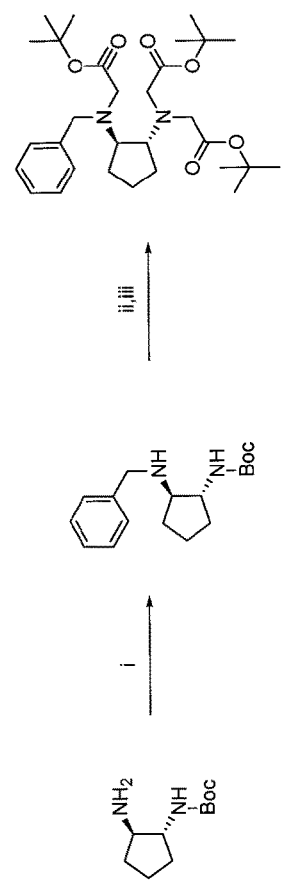
Figure 27:
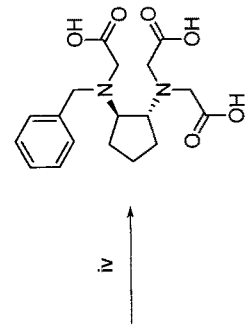
Figure 27:
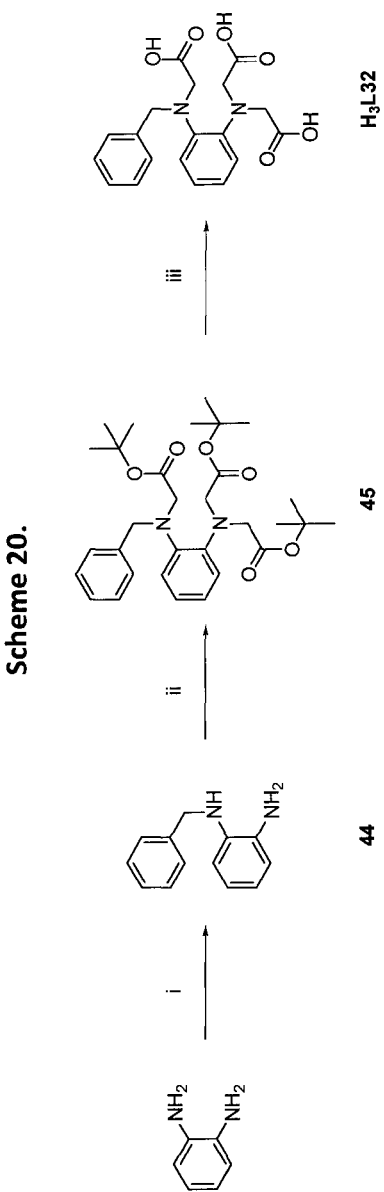
Figure 27:
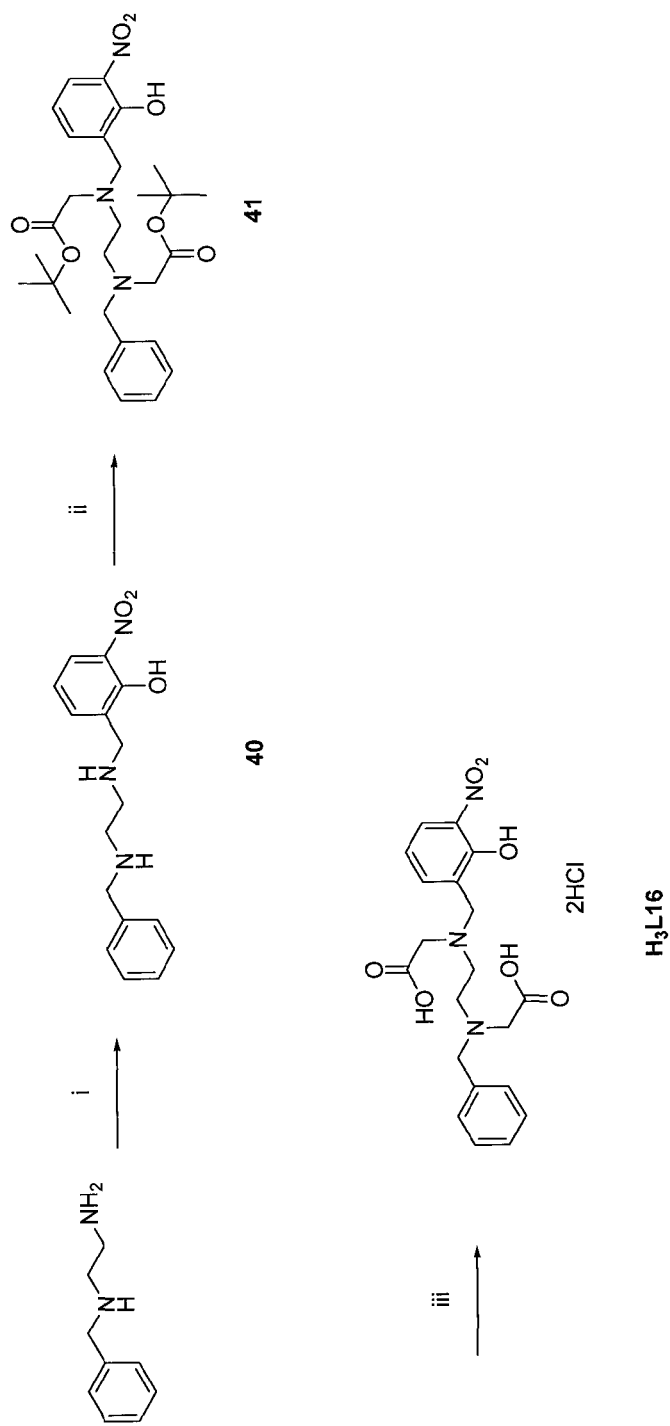
Figure 27:
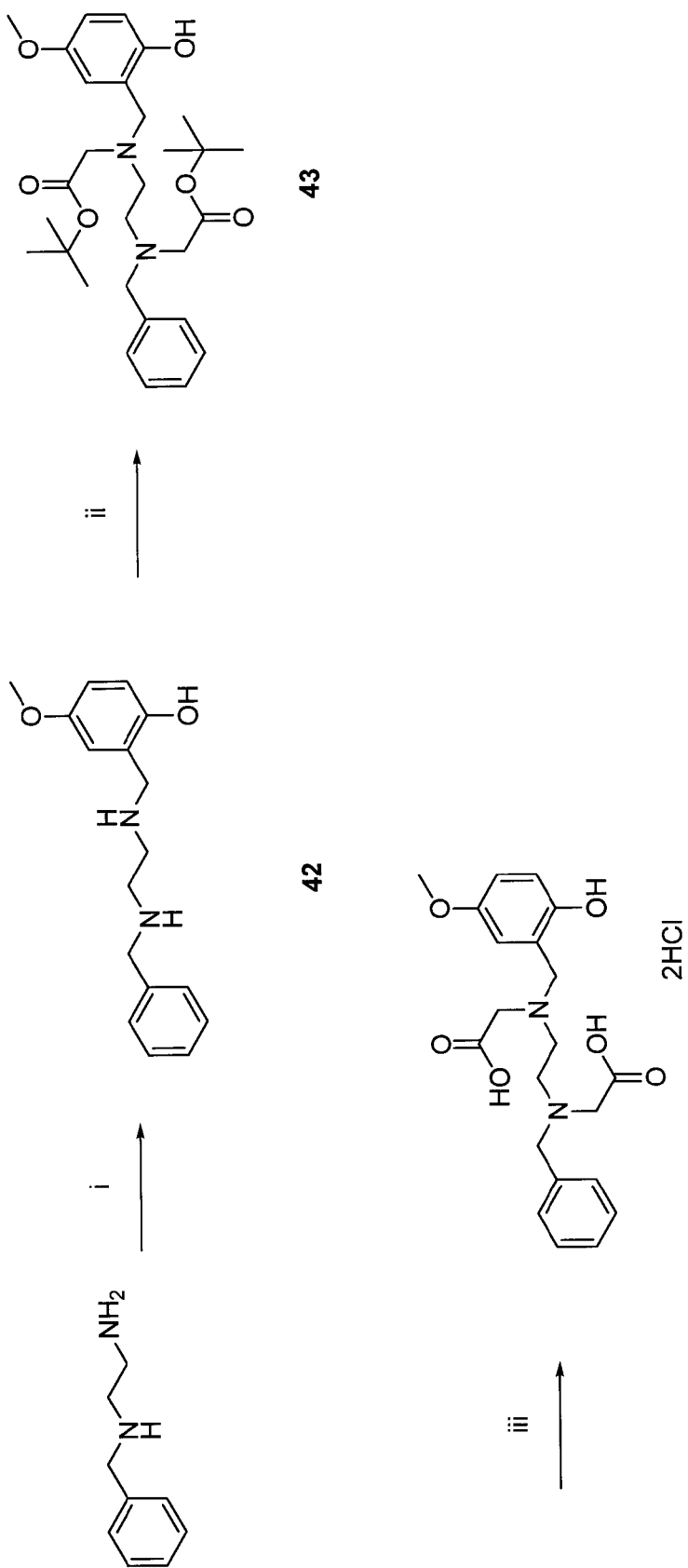

Scheme 1. displays the synthesis of H$_3$L1 i) Ethyl bromoacetate, K$_2$CO$_3$, THF, rt ii) NaOH, MeOH, rt Scheme 2. displays the synthesis of H$_3$L2 i) Salicylaldehyde, 50° C. MeOH, NaBH$_4$. ii) tert-butyl bromoacetate, Na$_2$HPO$_4$, THF iii) TFA, rt Scheme 3. displays the synthesis of H$_3$L3 i) Salicylaldehyde, 50° C. MeOH, NaBH$_4$ EtOH, rt ii) tert-butyl bromoacetate, DIPEA, THF iii) TFA, rt Scheme 4. displays the synthesis of H$_3$L4 i) 5-fluoro-2-hydroxybenzaldehyde, 50° C. MeOH, NaBH$_4$, EtOH, rt ii) tert-butyl bromoacetate, DIPEA, THF iii) TFA, rt Scheme 5. displays the synthesis of H$_3$L5 i) 5-nitro-2-hydroxybenzaldehyde, 50° C. MeOH, NaBH$_4$, EtOH, rt ii) tert-butyl bromoacetate, DIPEA, THF iii) TFA, rt Scheme 6. displays the synthesis of compound 13 i) Salicylaldehyde, MeOH, 65° C., 1 h, then NaBH$_4$, rt, 4 h; ii) HCl 1N, rt, 16 h; iii) 4-carboxybenzaldehyde, DIPEA, MeOH, 70° C., 1 h, then NaBH$_4$, rt, 4 h; iv) tert-butyl bromoacetate, DIPEA, MeOH, rt, 16 h.

Scheme 7. displays the synthesis of H$_2$L7 i) 2-pyridinecarboxaldehyde, MeOH, rt, 24 h, then NaBH$_4$, rt, 16 h; ii) tert-butyl bromoacetate, DIPEA, MeOH, rt, 16 h; iii) TFA, rt, 16 h.

Scheme 8. displays the synthesis of H$_3$L8 i) benzyl bromide, K$_2$CO$_3$, THF, rt, 7 d; ii) HCl 1N, rt, 16 h; iii) Salicylaldehyde, DIPEA, MeOH, 70° C., 1 h, then NaBH$_4$, rt, 4 h; iv) bromoacetic acid, DIPEA, EtOH, reflux, 16 h.

Scheme 9. displays the synthesis of H$_3$L9 i) tert-butyl bromoacetate, DIPEA, MeOH, rt, 24 h; ii) TFA, rt, 16 h.

Scheme 10. displays the synthesis of H$_2$L10 i) 2-(Boc-amino)ethyl bromide, DIPEA, THF, rt, 5 d then 50° C., 15 d, ii) HCl 1 N, rt, 16 h.

Scheme 11. displays the synthesis of H$_2$L11 i) 3-pyridinecarboxaldehyde, MeOH, rt, 24 h, then NaBH$_4$, rt, 16 h; ii) tert-butyl bromoacetate, DIPEA, MeOH, rt, 16 h; iii) TFA, rt, 16 h.

Scheme 12. displays the synthesis of H$_2$L12 i) Benzylbromide, K$_2$CO$_3$, THF rt. ii) TFA rt, Salicylaldehyde, MeOH 50° C., NaBH$_4$ rt.

Scheme 13. displays the synthesis of H$_3$L13 i) Toluene-4-sulfonyl Et$_2$O, NaOH rt ii) MeONa, EtOH, reflux, 30 min, 1,3-dibromopropan-2-ol, 6 h reflux iii) Acetic anhydride, 30% HBr in Acetic acid, phenol 60° C. 6 h iv) tert-butyl bromoacetate, K$_2$CO$_3$, ACN, rt v) TFA, rt, 12 h vi) H$_2$O, reflux, 12 h Scheme 14. displays the synthesis of H$_3$L24 and H$_3$L25 i) methyl bromoacetate, K$_2$CO$_3$, THF, RT ii) hydroxylamine 50% aq., NaOH, MeOH, THF, 0° C. 1 h, RT 2 h Scheme 15. displays the synthesis of H$_3$L26 i) benzaldehyde, 65° C. MeOH, NaBH$_4$, MeOH, 0° C. ii) tert-butyl bromoacetate, DIPEA, DCM, rt iii) TFA, rt, 12 h Scheme 16. displays the synthesis of H$_3$L27 i) benzaldehyde, 65° C. MeOH, NaBH$_4$, MeOH, 0° C. ii) tert-butyl bromoacetate, DIPEA, DCM, rt, iii) NH4HCO2, Pd/C, _ MeOH 65° C. 4 h. iv) 4-(bromomethyl)-phenylacetic, DIPEA, DCM, rt, v) TFA, rt, 12 h Scheme 17. displays the synthesis of H$_3$L28 i) DCC, TFP, dioxane 12 h rt ii) TFA 4 h rt Scheme 18. displays the synthesis of H$_3$L29 i) tert-butyl bromoacetate, DIPEA, DCM, rt; ii) paraformaldehyde, MeOH, 65° C., NaBH$_3$CN, MeOH, rt; iii) TFA, rt Scheme 19. displays the synthesis of H$_3$L30 i) benzaldehyde, 65° C. MeOH, NaBH4, MeOH, 0° C. ii) tert-butyl bromoacetate, DIPEA, DCM, rt, iii) TFA, rt, 12 h Scheme 20. displays the synthesis of H$_3$L31 i)benzaldehyde, 65° C. MeOH, NaBH4, MeOH, 0° C. ii) tert-butyl bromoacetate, DIPEA, DCM, rt, iii) TFA, rt, 12 h Scheme 21. displays the synthesis of H$_3$L32 i)benzyl bromide, 40° C. ACN, 24 h ii) tert-butyl bromoacetate, DIPEA, ACN, reflux, 12 h iii) TFA, rt, 12 h Scheme 22. displays the synthesis of H$_3$L16 i) 3-nitro-2-hydroxybenzaldehyde, 50° C. MeOH, NaBH$_4$, EtOH, rt ii) tert-butyl bromoacetate, DIPEA, THF, rt iii) HCl (4M) in dioxane, rt Scheme 23. displays the synthesis of H$_3$L17 i) 5-methoxy-2-hydroxybenzaldehyde, 50° C. MeOH, NaBH$_4$, EtOH, rt ii) tert-butyl bromoacetate, DIPEA, THF, rt iii) HCl (4M) in dioxane, rt

REFERENCES TO THIS APPLICATION

1. Radiopharmaceuticals in Nuclear Pharmacy and Nuclear Medicine, Richard J. Kowalsky, Steven W. Falen-2$^{nd}$ ed.
2. Textbook of Radiopharmacy: theory and practice, Sampson, Charles B-3rd ed.
3. Munich molecular imaging handbook series, Hans J. Wester
4. Nuclear medicine: Fusing the ideas of Democritus and Hippocrates, 25 years of the EANM, E. Bombardieri, S. Frangos
5. Molecular imaging with PET, S. M. Ametamey, M. Honer and P. A. Schubiger, *Chem. Rev.* 2008, 108, 1501-1516. (10.1021/cr0782426)
6. Positron emission tomography provides molecular imaging of biological processes, M. E. Phelps, *Proc. Natl. Acad. Sci. U.S.A*. 2000, 97, 9226-9233. (10.1073/pnas.97.16.9226)
7. Emission Tomography: The fundamentals of PET and SPECT, M. N. Wernick and J. N. Asrsvold, Elsevier Academic Press 2004
8. Eder, M. et al. Tetrafluorophenolate of HBED-CC: a versatile conjugation agent for 68Ga-labelled small recombinant antibodies. *Eur. J. Nucl. Med. Mol. Imaging* 35, 1878-1886 (2008).
9. Smith, G. E., Sladen, H. L., Biagini, S. C. G. & Blower, P. J. Inorganic approaches for radiolabelling biomolecules with fluorine-18 for imaging with positron emission tomography. Dalton Trans. 40, 6196-6205 (2011).
10. McBride, W. J., Sharkey, R. M. & Goldenberg, D. M. Radiofluorination using aluminum-fluoride (Al18F). EJNMMI Res. 3, 36 (2013).
11. McBride, W. J., D' Souza, C. A., Sharkey, R. M. & Goldenberg, D. M. The radiolabeling of proteins by the [18F]AlF method. *Appl. Radiat. Isot*. 70, 200-204 (2012)
12. Shetty, D. et al. Stable aluminium fluoride chelates with triazacyclononane derivatives proved by X-ray crystallography and (18)F-labeling study. *Chem. Commun. (Camb)*. 47, 9732-9734 (2011).
13. Laverman P, McBride W J, Sharkey R M, Eek A, Joosten L, Oyen W J, Goldenberg D M, Boerman O C. A novel facile method of labeling octreotide with (18)F-fluorine. *J Nucl Med*. 51(3):454-61. (2010)
14. Varasteh Z, Aberg O, Velikyan I, Lindeberg G, Sörensen J, Larhed M, Antoni G, Sandström M, Tolmachev V, Orlova A. In vitro and in vivo evaluation of a (18)F-labeled high affinity NOTA conjugated bombesin antagonist as a PET ligand for GRPR-targeted tumor imaging. *PLoS One*. 3; 8(12):e81932 (2013)
15. Yokel, R. A. Aluminum chelation principles and recent advances. *Coord. Chem. Rev.* 228, 97-113 (2002).
16. McBride W J, Sharkey R M, Karacay H, D'Souza C A, Rossi E A, Laverman P, Chang C H, Boerman O C, Goldenberg D M. A novel method of 18F radiolabeling for PET. *J Nucl Med*. 50(6):991-8. (2009)
17. Lütje S, Franssen G M, Sharkey R M, Laverman P, Rossi E A, Goldenberg D M, Oyen W J, Boerman O C, McBride W J. Anti-CEA antibody fragments labeled with [(18)F] AlF for PET imaging of CEA-expressing tumors. *Bioconjug Chem*. 19; 25(2):335-41 (2014)
18. Balsells J, J. Carroll P, J. Walsh P. Achiral Tetrahydrosalen Ligands for the Synthesis of C 2 Symmetric Titanium Complexes: A Structure and Diastereoselectivity Study. *Inorg. Chem*. 2001, 40, 5568-5574
19. Serratrice G, Galey J B, Saint Aman E, Dumats J. Iron(III) Complexation by New Aminocarboxylate Chelators: Thermodynamic and Kinetic Studies *Eur. J. Inorg. Chem*. 2001, 4712479
20. Mitterhauser M, Toegel S, Wadsak W, Lanzenberger R R, Mien L K, Kuntner C, Wanek T, Eidherr H, Ettlinger D E, Viernstein H, Kluger R, Dudczak R, Kletter K. Pre vivo, ex vivo and in vivo evaluations of [$^{68}$Ga]-EDTMP. *Nucl. Med. Biol*. 2007, 34, 391-397
21. Fritzberg A R, Whitney W P, Kuni C C, Klingensmith W. Biodistribution and renal excretion of 99mTc-N—N'-bis(mercaptoacetamido)ethylenediamine. *Int. J. Nucl. Med. Biol*. 1982, 9, 79-82

The invention claimed is:

1. A chelate of $\{Al^{18}F\}^{2+}$ with a compound selected from the group consisting of:
a compound having the formula (I):

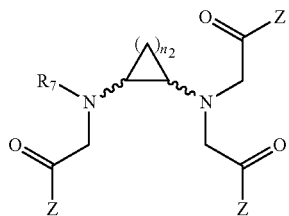

wherein:
n2 is 4, wherein the 6-membered ring is cyclic without additional substituents, or includes a double bond, or is aromatic;
Z is OH;
$R_7$ is a —$CH_2$-Ph-R' group with R' in ortho, meta or para position, wherein R' is selected from the group consisting of a hydrogen atom, —COOH, —$NH_2$, —N=C=S, —SH, an activated ester and a group bearing a maleimide adapted to couple with compounds bearing a suitable chemical function,
the asymmetric carbon atoms are in (R) or (S) configuration,
or a pharmaceutically acceptable salt thereof.

2. A kit for radiolabeling of a molecule with $^{18}F$, including a heat sensitive molecule, whereby the kit comprises an $\{Al^{18}F\}^{2+}$ chelate according to claim 1, wherein the heat sensitive molecule is a peptide or a protein.

3. The kit according to claim 2, whereby the kit further comprises reagents or media.

4. The chelate of claim 1, wherein the chelate is obtained at a temperature <40° C.

* * * * *